(12) United States Patent
Stamford et al.

(10) Patent No.: US 6,982,267 B2
(45) Date of Patent: Jan. 3, 2006

(54) HETEROARYL UREA NEUROPEPTIDE Y Y5 RECEPTOR ANTAGONISTS

(75) Inventors: Andrew Stamford, Chatham, NJ (US); Youhao Dong, Keasbey, NJ (US); Stuart W. McCombie, Caldwell, NJ (US); Yusheng Wu, New York, NY (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/026,651

(22) Filed: Dec. 18, 2001

(65) Prior Publication Data

US 2003/0055062 A1 Mar. 20, 2003

Related U.S. Application Data

(60) Provisional application No. 60/257,308, filed on Dec. 21, 2000.

(51) Int. Cl.
| | |
|---|---|
| C07D 241/26 | (2006.01) |
| C07D 409/04 | (2006.01) |
| A61K 31/4965 | (2006.01) |
| A61K 31/497 | (2006.01) |
| A61K 3/04 | (2006.01) |

(52) U.S. Cl. .................. 514/255.05; 514/255.06; 544/405; 544/336

(58) Field of Classification Search .............. 544/405, 544/336; 514/255.05, 255.06, 252.1, 256, 514/252.14

See application file for complete search history.

(56) References Cited

U.S. PATENT DOCUMENTS

| | | | |
|---|---|---|---|
| 4,405,644 A | 9/1983 | Kabbe | 424/322 |
| 4,623,662 A | 11/1986 | De Vries | 514/580 |

FOREIGN PATENT DOCUMENTS

| | | |
|---|---|---|
| EP | 1 249 233 A1 | 10/2002 |
| WO | WO 96/16542 | 6/1996 |
| WO | WO 99/09024 | 2/1999 |
| WO | WO 00/27845 | 5/2000 |
| WO | WO 01/14376 A1 | 3/2001 |
| WO | WO 01/37826 A1 | 5/2001 |

OTHER PUBLICATIONS

Betancur et al., TIPS vol. 18, 372–386, 1997.*
Wieland et al., Expert Opin. Investig. Drugs 9(6): 1327–1346,2000.*
West, Anthony R. Solid state chemistry and its application, pp. 358, 365, 1988.*
Stanley, et al. "Neuropeptide Y injected in the paraventricular hypothalamus: A powerful stimulant of feeding behavior" *Proc. Natl. Acad. Sci.* 82:3940–3943(1985).
Billington, et al. "Effects of intracerebroventricular injection of neuropeptide Y on energy metabolism" *Am. J. Physiol.* 260:R321–R327 (1991).
Wahlestedt, et al. "Neuropeptide Y–related peptides and their receptors—are the receptors potential therapeutic drug targets?" *Ann. Rev. Pharmacol. Toxicol.* 32:309–352 (1993).
Gerald, et al. "A receptor subtype involved in neuropeptide–Y–induced food intake" *Nature* 382:168–171 (1996).
Gehlert, D., "Minireview—Multiple Receptors for the Pancreatic Polypeptide (PP–Fold) Family: Physiological Implications" *Proc. Soc. Exp. Biol. Med.* 218:7–22(1998).
Michel, et al., "XVI. International Union of Pharmacology Recommendations for the Nomenclature of Neuropeptide Y, Peptide YY, and Pancreatic Polypeptide Receptors" *Pharmacol. Rev.* 50(1):143–150(1998).
Hwa, et al. "Activation of the NPY Y5 receptor regulates both feeding and energy expenditure" *American J. Physiological* 277(46):R1428–R1434(1999).

* cited by examiner

*Primary Examiner*—Venkataraman Balasubramanian
(74) *Attorney, Agent, or Firm*—William Y. Lee

(57) ABSTRACT

The present invention relates to compounds represented by the structural Formula I:

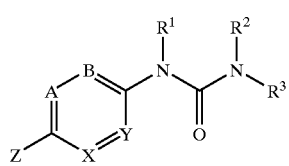

or a pharmaceutically acceptable salt thereof, which are useful for the treatment of metabolic and eating disorders such as obesity and hyperphagia, and for the treatment of diabetes and associated disorders.

16 Claims, No Drawings

HETEROARYL UREA NEUROPEPTIDE Y Y5 RECEPTOR ANTAGONISTS

This application claims benefit of U.S. Provisional Application Ser. No. 60/257,308 filed on Nov. 21, 2000.

This invention relates to heteroaryl urea neuropeptide Y Y5 receptor antagonists useful in the treatment of eating disorders, pharmaceutical compositions containing the compounds, and methods of treatment using the compounds.

Neuropeptide Y (NPY) is a 36 amino acid neuropeptide that is widely distributed in the central and peripheral nervous systems. NPY is a member of the pancreatic polypeptide family that also includes peptide YY and pancreatic polypeptide (Wahlestedt, C., and Reis, D., Ann. Rev. Toxicol., 32, 309, 1993). NPY elicits its physiological effects by activation of at least six receptor subtypes designated Y1, Y2, Y3, Y4, Y5 and Y6 (Gehlert, D., Proc. Soc. Exp. Biol. Med., 218, 7, 1998; Michel, M. et al., Pharmacol. Rev, 50, 143, 1998). Central administration of NPY to animals causes dramatically increased food intake and decreased energy expenditure (Stanley, B. and Leibowitz, S., Proc. Natl. Acad. Sci. USA 82: 3940, 1985; Billington et al., Am J. Physiol., 260, R321, 1991). These effects are believed to be mediated at least in part by activation of the NPY Y5 receptor subtype. The isolation and characterization of the NPY Y5 receptor subtype has been reported (Gerald, C. et al., Nature, 1996, 382, 168; Gerald, C. et al. WO 96/16542). Additionally, it has been reported that activation of the NPY Y5 receptor by administration of the Y5—selective agonist [D-Trp$^{32}$]NPY to rats stimulates feeding and decreases energy expenditure (Gerald, C. et al., Nature, 1996, 382, 168; Hwa, J. et al., Am. J. Physiol., 277 (46), R1428, 1999). Hence, compounds that block binding of NPY to the NPY Y5 receptor subtype should have utility in the treatment of eating disorders such as obesity, bulimia nervosa, anorexia nervosa, and in the treatment of disorders associated with obesity such as type 11 diabetes, insulin resistance, hyperlipidemia, and hypertension.

Published PCT patent application WO 00/27845 describes a class of compounds, characterized therein as spiro-indolines, said to be selective neuropeptide Y Y5 receptor antagonists and useful for the treatment of obesity and the complications associated therewith. Known urea derivatives indicated as possessing therapeutic activity are described in U.S. Pat. Nos. 4,623,662 (antiatherosclerotic agents) and 4,405,644 (treatment of lipometabolism).

Provisional application, U.S. Ser. No. 60/232,255 describes a class of substituted urea neuropeptide Y Y5 receptor antagonists.

SUMMARY OF THE INVENTION

This invention relates to compounds of Formula I:

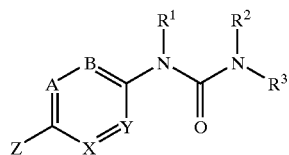

I a prodrug thereof, or a pharmaceutically acceptable salt and/or hydrate of said compound or of said prodrug, or where applicable, a geometric or optical isomer or racemic mixture thereof, wherein =A-B= is =C(R$^4$)—C(R$^5$)= and —X=Y— is —C(R))=N—, —N=C(R$^7$)—, —N=N— or —S—, or =A-B= is =N—C(R$^5$)= and —X=Y— is —N=C(R$^7$)—, —C(R$^6$)=N—, —S— or —O—, or =A-B= is =C(R$^4$)—N= and —X=Y— is —C(R$^6$)=N—, —S— or —O—, or =A-B= is =N—N= and —X=Y— is —S— or —O—, or =A-B= is =C(R$^4$)— and —X=Y— is —S—N=, —N(R$^{10}$)—N=, or =A-B= is —C(R$^4$)= and —X=Y— is =N—S—, or =N—N(R$^{10}$)—;

Z is

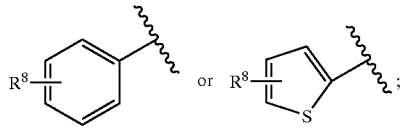

$R^1$ is H or —(C$_1$-C$_6$)alkyl;
$R^2$ is H, —(C$_1$-C$_6$)alkyl, —(C$_3$-C$_7$)cycloalkyl or —(C$_1$-C$_6$)alkyl(C$_3$-C$_7$)cycloalkyl;
$R^3$ is

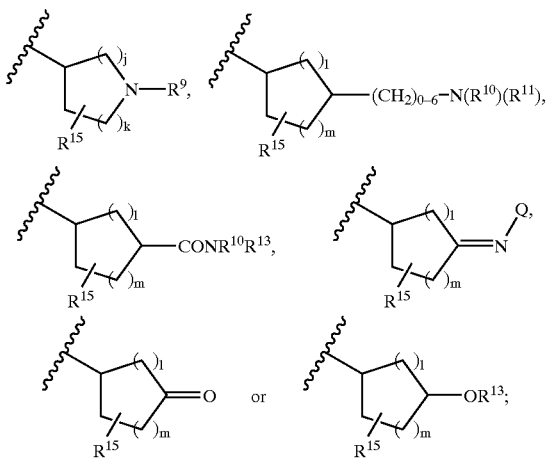

Q is —OR$^{13}$, or —NR$^{13}$R$^{14}$;
j is 1 or 2;
k is 0, 1 or 2;
l is 0, 1 or 2;
m is 1 or 2;
$R^4$, $R^5$, $R^6$ and $R^7$ may be the same or different, and are independently selected from the group consisting of H, —OH, halogen, polyhaloalkyl, —(C$_1$-C$_6$)alkyl, —(C$_3$-C$_7$)cycloalkyl, —(C$_1$-C$_6$)alkyl(C$_3$-C$_7$)cycloalkyl, —CN, NR$^{10}$R$^{11}$, NR$^{13}$R$^{14}$, —O(C$_1$-C$_6$)alkyl, —O(C$_3$-C$_7$)cycloalkyl, —O(C$_1$-C$_6$)alkyl(C$_3$-C$_7$)cycloalkyl, —S(C$_1$-C$_6$)alkyl, —S(C$_3$-C$_7$)cycloalkyl or —S(C$_1$-C$_6$)alkyl(C$_3$-C$_7$)cycloalkyl;
$R^8$ is 1 to 3 substituents, which may be the same or different, and are independently selected from the group consisting of H, halogen, —OH, polyhaloalkyl, polyhaloalkoxy, —CN, —NO$_2$, —(C$_1$-C$_6$)alkyl, —(C$_3$-C$_7$)cycloalkyl, —(C$_1$-C$_6$)alkyl(C$_3$-C$_7$)cycloalkyl, NR$^{10}$R$^{11}$, NR$^{13}$ R$^{14}$, —O(C$_1$-C$_6$)alkyl, —O(C$_3$-C$_7$)cycloalkyl, —O(C$_1$-C$_6$)alkyl(C$_3$-C$_7$)cycloalkyl or —CONR$^{13}$R$^{14}$;
$R^9$ is —SO$_2$(C$_1$-C$_6$)alkyl, —SO$_2$(C$_3$-C$_7$)cycloalkyl, —SO$_2$(C$_1$-C$_6$)alkyl(C$_3$-C$_7$)cycloalkyl, —SO$_2$(C$_1$-C$_6$)

polyhaloalkyl, —SO$_2$[hydroxy(C$_2$-C$_6$)alkyl], —SO$_2$[amino(C$_2$-C$_6$)alkyl], —SO$_2$[alkoxy(C$_2$-C$_6$)alkyl], —SO$_2$[alkylamino(C$_2$-C$_6$)alkyl], —SO$_2$[dialkylamino (C$_2$-C$_6$)alkyl], —SO$_2$(aryl), —SO$_2$(heteroaryl), —SO$_2$[aryl(C$_1$-C$_6$) alkyl], —SO$_2$NR$^{13}$R$^{14}$, —CO(C$_1$-C$_6$) alkyl, —CO(C$_3$-C$_7$)cycloalkyl, —CO(C$_1$-C$_6$)alkyl (C$_3$-C$_7$)cycloalkyl, CO(C$_1$-C$_6$)polyhaloalkyl, —C(O)aryl, —C(O)heteroaryl, —CONR$^{13}$R$^{14}$, —C(S)NR$^{13}$R$^{14}$, aryl, heteroaryl, —(CH$_2$)CONR$^{13}$R$^{14}$, —C(=NCN)alkylthio, —C(=NCN)NR$^{13}$R$^{14}$, —(C$_1$-C$_6$)alkyl, —(C$_3$-C$_7$)cycloalkyl, —(C$_1$-C$_6$)alkyl (C$_3$-C$_7$)cycloalkyl, —(C$_1$-C$_6$)alkylaryl, —(C$_1$-C$_6$)alkylheteroaryl or —COOR$^{12}$;

R$^{10}$ is H or alkyl;

R$^{11}$ is H, —(C$_1$-C$_6$)alkyl, —(C$_3$-C$_7$)cycloalkyl, —(C$_1$-C$_6$)alkyl(C$_3$-C$_7$)cycloalkyl, aryl, heteroaryl, —SO$_2$(C$_1$-C$_6$)alkyl, —SO$_2$(C$_3$-C$_7$)cycloalkyl, —SO$_2$(C$_1$-C$_6$)alkyl(C$_3$-C$_7$)cycloalkyl, —SO$_2$(C$_1$-C$_6$)polyhaloalkyl, —SO$_2$(aryl), —SO$_2$(heteroaryl), —CO(C$_1$-C$_6$)alkyl, —CO(C$_3$-C$_7$)cycloalkyl, —CO(C$_1$-C$_6$)alkyl(C$_3$-C$_7$)cycloalkyl, —C(O)aryl, —C(O)heteroaryl, —CONR$^{13}$R$^{14}$ or —COOR$^{12}$;

R$^{12}$ is (C$_1$-C$_6$)alkyl, (C$_3$-C$_7$)cycloalkyl, (C$_1$-C$_6$)alkyl(C$_3$-C$_7$)cycloalkyl, —(C$_1$-C$_6$)alkylaryl, —(C$_1$-C$_6$)alkylheteroaryl, aryl or heteroaryl;

R$^{13}$ and R$^{14}$ may be the same or different and are independently selected from H, —(C$_1$-C$_6$)alkyl, —(C$_3$-C$_7$)cycloalkyl, —(C$_1$-C$_6$)alkyl(C$_3$-C$_7$)cycloalkyl, —(C$_1$-C$_6$)alkylaryl, aryl or heteroaryl; and, R$^{15}$ is one or two substituents which may be the same or different and are independently selected from H, —(C$_1$-C$_6$)alkyl, —(C$_3$-C$_7$)cycloalkyl, —(C$_1$-C$_6$)alkyl (C$_3$-C$_7$)cycloalkyl, aryl, heteroaryl, —CN, —CONR$^{13}$R$^4$, —COOR$^{13}$, —OH, —O(C$_1$-C$_6$)alkyl, —O(C$_3$-C$_7$)cycloalkyl, —O(C$_1$-C$_6$)alkyl(C$_3$-C$_7$)cycloalkyl, —NR$^{10}$R$^{11}$, —NR$^{13}$R$^{14}$, or a —(C$_1$-C$_6$)alkyl group substituted by an aryl, heteroaryl, hydroxy, alkoxy, —NR$^{10}$R$^{11}$, —NR$^{13}$R$^{14}$, —CONR$^{13}$R$^{14}$, or —COOR$^{13}$ group, provided that a chemically stable compound results from substitution by R$^{15}$.

The invention also relates to pharmaceutical compositions containing the compounds of the invention, as well as methods of using the compounds alone or in combination with other therapeutic agents.

DETAILED DESCRIPTION OF THE INVENTION

The present invention relates to compounds of Formula I:

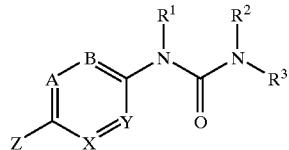

a prodrug thereof, or a pharmaceutically acceptable salt and/or hydrate of said compound or of said prodrug, or where applicable, a geometric or optical isomer or racemic mixture thereof, wherein =A-B= is =C(R$^4$)—C(R$^5$)= and —X=Y— is —C(R$^6$)=N—, —N=C(R$^7$)—, —N=N— or —S—, or =A-B= is =N—C(R$^5$)= and —X=Y— is —N=C(R$^7$)—, —C(R$^6$)=N—, —S— or —O—, or =A-B= is =C(R$^4$)—N= and —X=Y— is —C(R$^6$)=N—, —S— or —O—, or =A-B= is =N—N= and —X=Y— is —S— or —O—, or =A-B= is —C(R$^4$)— and —X=Y— is —S—N=, —N(R$^{10}$)—N=, or =A-B= is =C(R$^4$)= and —X=Y— is =N—S—, or =N—N(R$^{10}$)—;

Z is

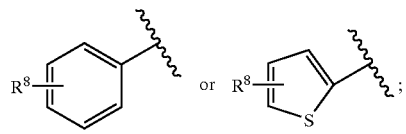

R$^1$ is H or —(C$_1$-C$_6$)alkyl;

R$^2$ is H, —(C$_1$-C$_6$)alkyl, —(C$_3$-C$_7$)cycloalkyl or —(C$_1$-C$_6$)alkyl(C$_3$-C$_7$)cycloalkyl;

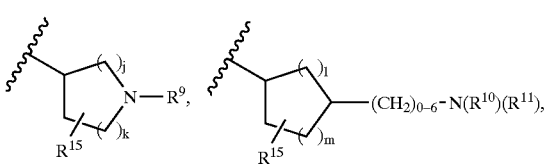

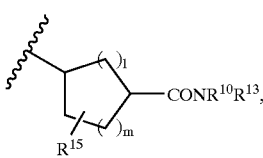

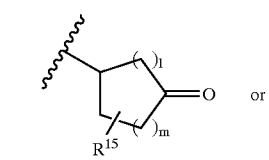

Q is —OR$^{13}$, or —NR$^{13}$R$^{14}$;

j is 1 or 2;

k is 0, 1 or 2;

i is 0, 1 or 2;

m is 0, 1 or 2;

R$^4$, R$^5$, R$^6$ and R$^7$ may be the same or different, and are independently selected from the group consisting of H, —OH, halogen, polyhaloalkyl, —(C$_1$-C$_6$)alkyl, —(C$_3$-C$_7$)cycloalkyl, —(C$_1$-C$_6$)alkyl(C$_3$-C$_7$)cycloalkyl, —CN, NR$^{10}$R$^{11}$, NR$^{13}$R$^{14}$, —O(C$_1$-C$_6$)alkyl, —O(C$_3$-C$_7$)cycloalkyl, —O(C$_1$-C$_6$)alkyl(C$_3$-C$_7$)cycolalkyl, —S(C$_1$-C$_6$)alkyl, —S(C$_3$-C$_7$)cycloalkyl or —S(C$_1$-C$_6$)alkyl(C$_3$-C$_7$)cycloalkyl;

R$^8$ is 1 to 3 substituents, which may be the same or different, and are independently selected from the group consisting of H, halogen, —OH, polyhaloalkyl, polyhaloalkoxy, —CN, —NO$_2$, —(C$_1$-C$_6$)alkyl, —(C$_3$-C$_7$)cycloalkyl, —(C$_1$-C$_6$)alkyl(C$_3$-C$_7$)cycloalkyl, NR$^{10}$R$^{11}$, NR$^{13}$R$^{14}$, —O(C$_1$-C$_6$)alkyl, —O($C_3$–$C_7$)cycloalkyl, —O($C_1$–$C_6$)alkyl($C_3$–$C_7$) cycloalkyl or —CONR$^{13}$R$^{14}$;

R$^9$ is —SO$_2$($C_1$–$C_6$)alkyl, —SO$_2$($C_3$–$C_7$)cycloalkyl, —SO$_2$($C_1$–$C_6$)alkyl($C_3$–$C_7$)cycloalkyl, —SO$_2$($C_1$–$C_6$) polyhaloalkyl, —SO$_2$[hydroxy($C_2$–$C_6$)alkyl], —SO$_2$ [amino($C_2$–$C_6$)alkyl], —SO$_2$[alkoxy($C_2$–$C_6$)alkyl], —SO$_2$[alkylamino($C_2$–$C_6$)alkyl], —SO$_2$[dialkylamino ($C_2$–$C_6$)alkyl], —SO$_2$(aryl), —SO$_2$(heteroaryl), —SO$_2$ [aryl($C_1$–$C_6$) alkyl], —SO$_2$NR$^{13}$R$^{14}$, —CO($C_1$–$C_6$) alkyl, —CO($C_3$–$C_7$)cycloalkyl, —CO($C_1$–$C_6$)alkyl ($C_3$–$C_7$)cycloalkyl, CO($C_1$–$C_6$)polyhaloalkyl, —C(O) aryl, —C(O)heteroaryl, —CONR$^{13}$R$^{14}$, —C(S) NR$^{13}$R$^{14}$, aryl, heteroaryl, —(CH$_2$)CONR$^{13}$R$^{14}$, —C(=NCN)alkylthio, —C(=NCN)NR$^{13}$R$^{14}$, —($C_1$–$C_6$)alkyl, —($C_3$–$C_7$)cycloalkyl, —($C_1$–$C_6$)alkyl ($C_3$–$C_7$)cycloalkyl, —($C_1$–$C_6$)alkylaryl, —($C_1$–$C_6$) alkylheteroaryl or —COOR$^{12}$;

R$^{10}$ is H or alkyl;

R$^{11}$ is H, —($C_1$–$C_6$)alkyl, —($C_3$–$C_7$)cycloalkyl, —($C_1$–$C_6$)alkyl($C_3$–$C_7$)cycloalkyl, aryl, heteroaryl, —SO$_2$($C_1$–$C_6$)alkyl, —SO$_2$($C_3$–$C_7$)cycloalkyl, —SO$_2$ ($C_1$–$C_6$)alkyl ($C_3$–$C_7$)cycloalkyl, —SO$_2$($C_1$–$C_6$) polyhaloalkyl, —SO$_2$(aryl), —SO$_2$(heteroaryl), —CO ($C_1$–$C_6$)alkyl, —CO($C_3$–$C_7$)cycloalkyl, —CO($C_1$–$C_6$) alkyl($C_3$–$C_7$)cycloalkyl, —C(O)aryl, —C(O) heteroaryl, —CONR$^{13}$R$^{14}$ or —COOR$^{12}$;

R$^{12}$ is —($C_1$–$C_6$)alkyl, ($C_3$–$C_7$)cycloalkyl, ($C_1$–$C_6$)alkyl ($C_3$–$C_7$)cycloalkyl, —($C_1$–$C_6$)alkylaryl, —($C_1$–$C_6$) alkylheteroaryl, aryl or heteroaryl;

R$^{13}$ and R$^{14}$ may be the same or different and are independently selected from H, —($C_1$–$C_6$)alkyl, —($C_3$–$C_7$)cycloalkyl, —($C_1$–$C_6$)alkyl($C_3$–$C_7$) cycloalkyl, —($C_1$–$C_6$)alkylaryl, aryl or heteroaryl; and, R$^{15}$ is one or two substituents which may be the same or different and are independently selected from H, —($C_1$–$C_6$)alkyl, —($C_3$–$C_7$)cycloalkyl, —($C_1$–$C_6$)alkyl ($C_3$–$C_7$)cycloalkyl, aryl, heteroaryl, —CN, —CONR$^{13}$R$^{14}$, —COOR$^{13}$, —OH, —O($C_1$–$C_6$)alkyl, —O($C_3$–$C_7$)cycloalkyl, —O($C_1$–$C_6$)alkyl($C_3$–$C_7$) cycloalkyl, —NR$^{10}$R$^{11}$, —NR$^{13}$R$^{14}$, or a —($C_1$–$C_6$) alkyl group substituted by an aryl, heteroaryl, hydroxy, alkoxy, —NR$^{10}$OR$^{11}$, —NR$^{13}$R$^{14}$, —CONR$^{13}$R$^{14}$, or —COOR$^{13}$ group, provided that a chemically stable compound results from substitution by R$^{15}$.

Except where stated otherwise, the following definitions apply throughout the present specification and claims. Additionally, all technical and scientific terms used herein have the same meaning as is commonly understood by one of skill in the art to which this invention belongs. These definitions apply regardless of whether a term is used by itself or in combination with other terms. Hence the definition of "alkyl" applies to "alkyl" as well as to the "alkyl" portions of "alkoxy", etc.

Alkyl represents a straight or branched saturated hydrocarbon chain having the designated number of carbon atoms. Where the number of carbon atoms is not specified, 1 to 6 carbons are intended.

Halo represents fluoro, chloro, bromo or iodo.

Aryl refers to a mono- or bicyclic ring system having one or two aromatic rings including, but not limited to, phenyl, naphthyl, tetrahydronaphthyl, indanyl, and the like. The aryl group can be unsubstituted or substituted with one, two, or three substituents independently selected from lower alkyl, halo, cyano, nitro, haloalkyl, hydroxy, alkoxy, carboxy, carboxamide, mercapto, sulfhydryl, amino, alkylamino and dialkylamino.

Heteroaryl refers to 5- to 10-membered single or benzo-fused aromatic rings consisting of 1 to 3 heteroatoms independently selected from the group consisting of —O—, —S—, and —N=, provided that the rings do not possess adjacent oxygen and sulfur atoms. The heteroaryl group can be unsubstituted or substituted with one, two, or three substituents independently selected from lower alkyl, halo, cyano, nitro, haloalkyl, hydroxy, alkoxy, carboxy, carboxamide, mercapto, sulfhydryl, amino, alkylamino, dialkylamino.

When a variable appears more than once in the structural formula, the identity of each variable appearing more than once may be independently selected from the definition for that variable.

N-oxides can form on a tertiary nitrogen present in an R substituent, or on =N— in a heteroaryl ring substituent and are included in the compounds of Formula I.

The expression "prodrug" refers to compounds that are drug precursors which following administration, release the drug in vivo via some chemical or physiological process (e.g., a prodrug on being brought to the physiological pH or through enzyme action is converted to the desired drug form).

The term "chemically stable compound" is defined as a compound that can be isolated, characterized, and tested for biological activity.

For compounds of the invention having at least one asymmetrical carbon atom, all isomers, including diastereomers, enantiomers and rotational isomers are contemplated as being part of this invention. The invention includes d and l isomers in both pure form and in admixture, including racemic mixtures. Isomers can be prepared using conventional techniques, either by reacting optically enriched or optically pure starting materials or by separating isomers of a compound of Formula I.

Compounds of Formula I can exist in unsolvated and solvated forms, including hydrated forms. In general, the solvated forms, with pharmaceutically acceptable solvents such as water, ethanol and the like, are equivalent to the unsolvated forms for purposes of this invention.

A compound of Formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution, such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

In a preferred group of compounds of Formula I, the heterocyclic group attached to Z is

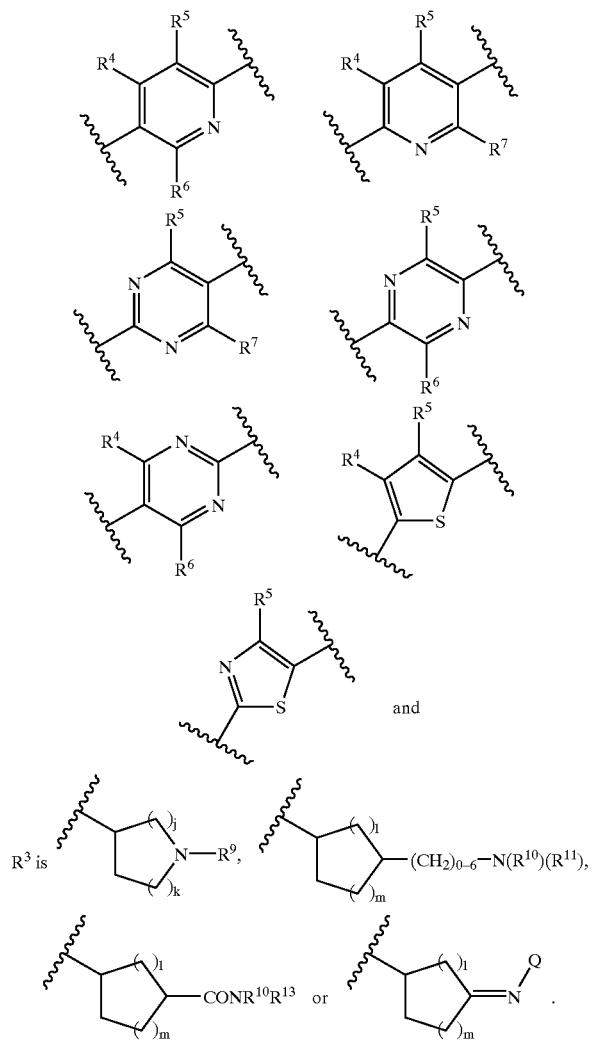

In particular, the preferred group includes the above compounds wherein $R^1$ is hydrogen, $R^2$ is hydrogen or —$(C_1-C_6)$alkyl, $R^4$, $R^5$, $R^6$ and $R^7$ are independently hydrogen or halogen, $R^8$ is 1–3 substitutents independently selected from the group consisting of H, halogen, —$O(C_1-C_6)$alkyl, —OH, polyhaloalkyl and polyhaloalkoxy, $R^9$ is —$SO_2(C_1-C_6)$alkyl, —$SO_2(C_3-C_7)$cycloalkyl, —$SO_2(C_1-C_6)$alkyl$(C_3-C_7)$cycloalkyl, —$SO_2$aryl, $SO_2$heteroaryl, —$SO_2NR^{13}R^{14}$, —$CO(C_1-C_6)$alkyl, —$CO(C_3-C_7)$cycloalkyl, —$CO(C_1-C_6)$alkyl$(C_3-C_7)$cycloalkyl, —$C(O)$aryl, —$C(O)$heteroaryl, aryl or heteroaryl, $R^{10}$ is H or alkyl, $R^{11}$ is —$SO_2(C_1-C_6)$alkyl, Q is —$OR^{13}$ or —$NR^{13}R^{14}$, $R^{13}$ and $R^{14}$ are independently selected from H or
—$(C_1-C_6)$alkyl, the sum of j and k is 2 or 3 and the sum of l and m is 2 or 3.

Another aspect of this invention is a method of treating a patient having a disease or condition mediated by NPY by administering a therapeutically effective amount of a compound of Formula I, a prodrug thereof, or a pharmaceutically acceptable salt of said compound or of said prodrug to the mammal. It is preferred that the receptor is the NPY-5 receptor.

Another aspect of this invention is directed to a method of treating obesity comprising administering to a patient in need of such treatment a therapeutically effective amount of a compound of Formula I or a prodrug thereof, or a pharmaceutically acceptable salt of said compound or of said prodrug.

Another aspect of this invention is directed to a method for treating eating and metabolic disorders such as bulimia and anorexia comprising administering to a patient a therapeutically effective amount of a compound of Formula I, a prodrug thereof, or a pharmaceutically acceptable salt of said compound or of said prodrug.

Another aspect of this invention is directed to a method for treating hyperlipidemia comprising administering to a patient a therapeutically effective amount of a compound of Formula I, a prodrug thereof, or a pharmaceutically acceptable salt of said compound or of said prodrug.

Another aspect of this invention is directed to a method for treating cellulite and fat accumulation comprising administering to a patient a therapeutically effective amount of a compound of Formula I, a prodrug thereof, or a pharmaceutically acceptable salt of said compound or of said prodrug.

Another aspect of this invention is directed to a method for treating type II diabetes comprising administering to a patient a therapeutically effective amount of a compound of Formula I, a prodrug thereof, or a pharmaceutically acceptable salt of said compound or of said prodrug.

In addition to the "direct" effect of the compounds of this invention on the NPY5 subtype, there are diseases and conditions that will benefit from the weight loss such as insulin resistance, impaired glucose tolerance, Type II Diabetes, hypertension, hyperlipidemia, cardiovascular disease, gall stones, certain cancers, and sleep apnea.

The compounds of the invention may also have utility in the treatment of central nervous system disorders such as seizures, depression, anxiety, alcoholism, pain; metabolic disorders such as hormone abnormalities; bone diseases such as osteoporosis, osteopenia, and Paget's disease; cardiovascular and renal disorders such hypertension, cardiac hypertrophy, vasopspasm and nephropathy; sexual and reproductive disorders; gastrointestinal disorders such as Crohn's disease; and respiratory diseases such as asthma.

This invention is also directed to pharmaceutical compositions which comprise an amount of a compound of Formula I, a prodrug thereof, or a pharmaceutically acceptable salt of said compound or of said prodrug and a pharmaceutically acceptable carrier therefor.

This invention is also directed to pharmaceutical compositions for the treatment of obesity which comprise an obesity treating amount of a compound of Formula, I, a prodrug thereof, or a pharmaceutically acceptable salt of said compound or of said prodrug and a pharmaceutically acceptable carrier therefor.

Compounds of Formula I may be produced by processes known to those skilled in the art and as shown in the following reaction schemes and in the preparations and examples below.

Scheme 1

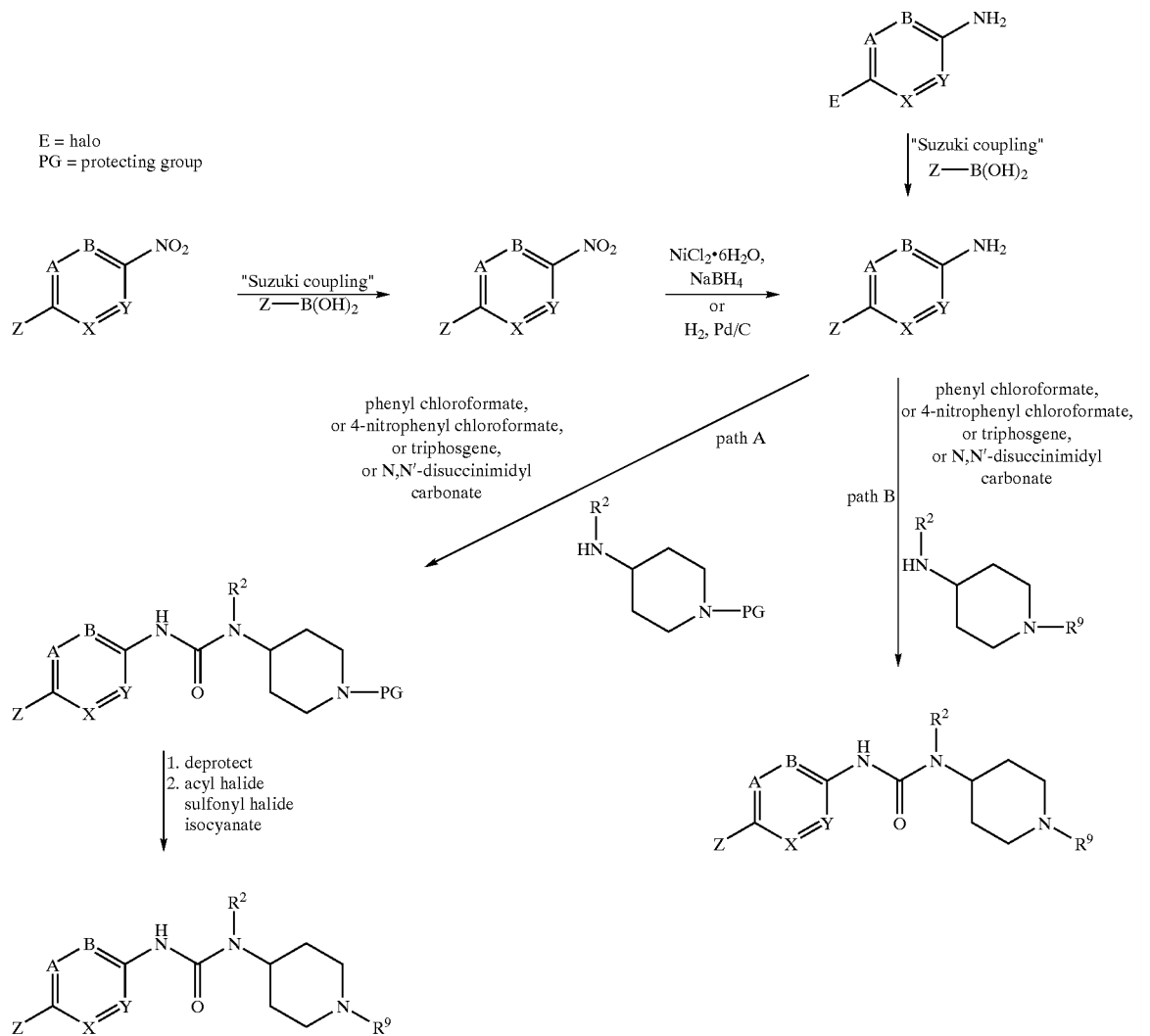

In Scheme 1, a nitro heteroaryl halide is coupled to an aryl boronic acid to give a nitro-substituted biaryl derivative. Reduction of the nitro group gives a biaryl amine derivative. Alternatively, an amino heteroaryl halide derivative is coupled to an aryl boronic acid derivative to directly give an amino biaryl derivative. Treatment of the biaryl amine with a reagent such as phenyl chloroformate, 4-nitrophenyl chloroformate, triphosgene, or N,N'-disuccinimidyl carbonate and an organic base, followed by an amino substituted cyclic amine derivative with the ring nitrogen protected, gives a urea derivative (path A). Cleavage of the protecting group provides an amine that can be derivatized by treatment with, for example, acyl chlorides, sulfonyl chlorides, and isocyanates. Alternatively, in the urea-forming step an amino substituted cyclic amine derivative wherein the ring nitrogen is derivatized with an $R^9$ substituent can be used (path B). Path B is the preferred method when $R^9$ is aryl or heteroaryl. Compounds of Formula I where

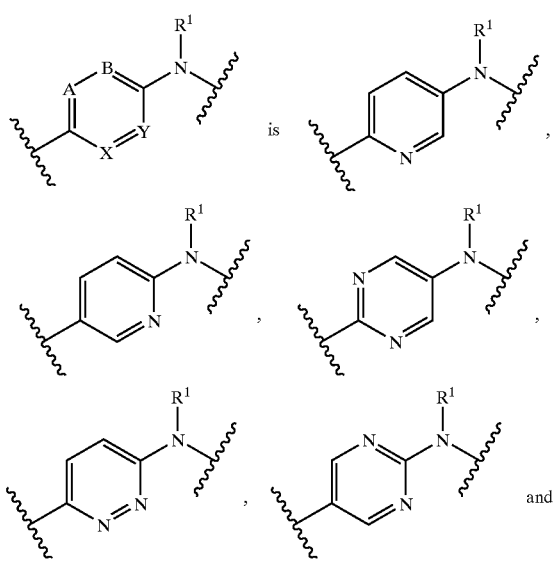

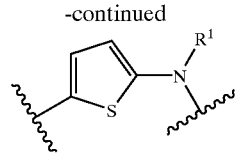

can be prepared by the methods outlined in Scheme 1.

Scheme 2

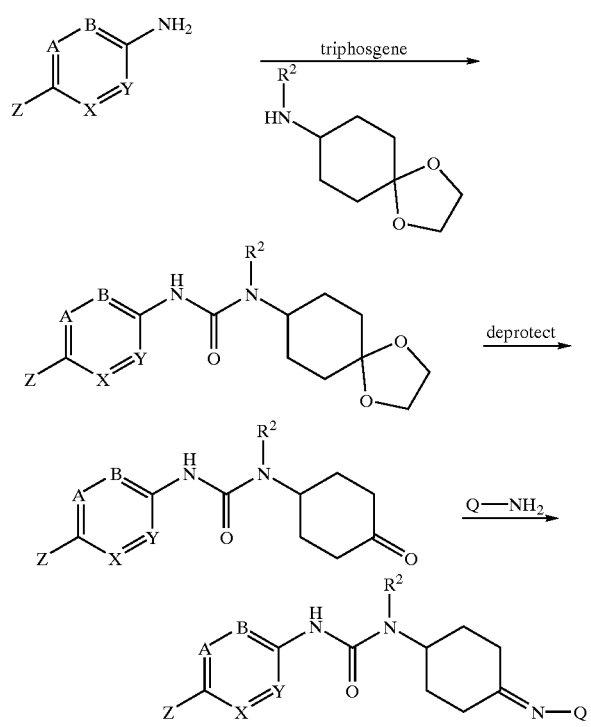

In Scheme 2, a biaryl amine derivative is treated with triphosgene and a base followed by treatment with 4-(methylamino)cyclohexanone ethylene ketal to give a urea derivative. Deprotection of the ketal, for example, by treatment with a strong acid, gives a ketone derivative. The ketone can then be derivatized by treatment with QNH$_2$.

Scheme 3

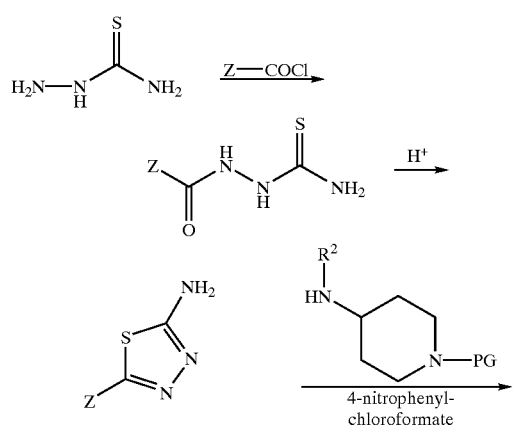

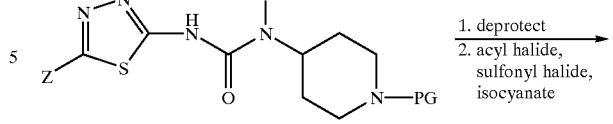

In Scheme 3, an acid chloride is condensed with thiosemicarbazide to give an N-acyl thiosemicarbazide derivative. Treatment of the N-acyl thiosemicarbazide with a strong acid results in the formation of an aminothiadiazole derivative. The aminothiadiazole is converted to a substituted urea derivative as described earlier.

Scheme 4

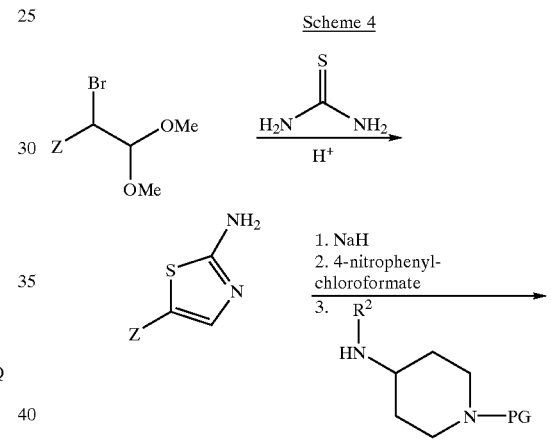

In Scheme 4 an alpha bromo acetal is condensed with thiourea to form a 5-substituted 2-aminothiazole derivative. The 2-aminothiazole derivative is converted to a substituted urea derivative as described in earlier schemes.

Scheme 5

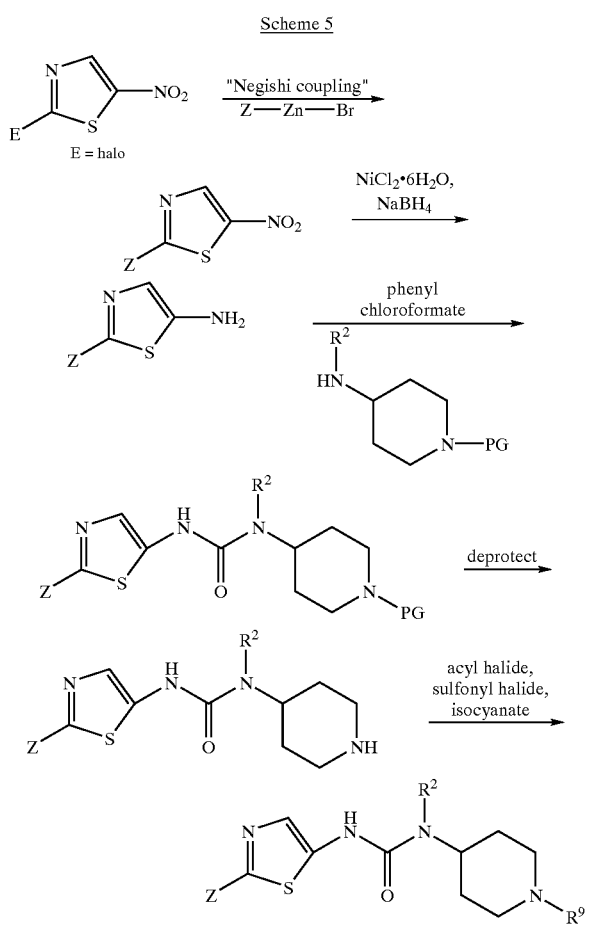

In Scheme 5, a 5-halo-2-nitrothiazole derivative is coupled to an arylzinc halide under palladium catalysis to give a 2-aryl-5-nitrothiazole derivative. The 5-nitrothiazole derivative is then converted to a substituted urea derivative as described in earlier Schemes.

The compounds of Formula I exhibit selective neuropeptide Y Y5 receptor antagonizing activity, which has been correlated with pharmaceutical activity for treating eating disorders, such as obesity and hyperphagia, and diabetes.

The compounds of Formula I display pharmacological activity in test procedures designed to demonstrate neuropeptide Y Y5 receptor antagonist activity. The compounds are non-toxic at pharmaceutically therapeutic doses. Following are descriptions of the test procedures.

cAMP Assay

HEK-293 cells expressing the Y5 receptor subtype were maintained in Dulbecco's modified Eagles' media (Gico-BRL) supplemented with 10% FCS (ICN), 1% penicillin-streptomycin and 200 μg/ml Geneticin®(GibcoBRL #11811-031) under a humidified 5% $CO_2$ atmosphere. Two days prior to assay, cells were released from T-175 tissue culture flasks using cell dissociation solution (1X; non-enzymatic [Sigma #C-5914]) and seeded into 96-well, flat-bottom tissue culture plates at a density of 15,000 to 20,000 cells per well. After approximately 48 hours, the cell monolayers were rinsed with Hank's balanced salt solution (HBSS) then preincubated with approximately 150 μl/well of assay buffer (HBSS supplemented with 4 mM $MgCl_2$, 10 mM HEPES, 0.2% BSA [HH]) containing 1 mM 3-isobutyl-1-methylxanthine ([IBMX] Sigma #I-587) with or without the antagonist compound of interest at 37° C. After 20 minutes the 1 mM IBMX-HH assay buffer (±antagonist compound) was removed and replaced with assay buffer containing 1.5 μM (CHO cells) or 5 μM (HEK-293 cells) forskolin (Sigma #F-6886) and various concentrations of NPY in the presence or absence of one concentration of the antagonist compound of interest. At the end of 10 minutes, the media were removed and the cell monolayers treated with 75 μl ethanol. The tissue culture plates were agitated on a platform shaker for 15 minutes, after which the plates were transferred to a warm bath in order to evaporate the ethanol. Upon bringing all wells to dryness, the cell residues were resolubilized with 250 I FlashPlate® assay buffer. The amount of cAMP in each well was quantified using the [$^{125}$I]-cAMP FlashPlate® kit (NEN #SMP-001) and according to the protocol provided by the manufacturer. Data were expressed as either pmol cAMP/ml or as percent of control. All data points were determined in triplicate and $EC_{50}$'s (nM) were calculated using a nonlinear (sigmoidal) regression equation (GraphPad Prism™). The $K_B$ of the antagonist compound was estimated using the following formula:

$$K_B=[B]/(1-\{[A']/[A]\})$$

where [A] is the $EC_{50}$ of the agonist (NPY) in the absence of antagonist,

[A'] is the $EC_{50}$ of the agonist (NPY) in the presence of antagonist, and [B] is the concentration of the antagonist.

NPY Receptor Binding Assay

Human NPY Y5 receptors were expressed in CHO cells. Binding assays were performed in 50 mM HEPES, pH 7.2, 2.5 mM $CaCl_2$, 1 mM $MgCl_2$ and 0.1% BSA containing 5–10 μg of membrane protein and 0.1 nM $^{125}$L-peptide YY in a total volume of 200 μl. Non-specific binding was determined in the presence of 1 μM NPY. The reaction mixtures were incubated for 90 minutes at room temperature then filtered through Millipore MAFC glass fiber filter plates which had been pre-soaked in 0.5% polyethleneimine. The filters were washed with phosphate-buffered saline, and radioactivity was measured in a Packard TopCount scintillation counter.

For the compounds of this invention, a range of neuropeptide Y5 receptor binding activity of from about 0.3 nM to about 1000 nM was observed. Compounds of this invention preferably have a binding activity in the range of from about 0.3 nM to about 500 nM, more preferably from about 0.3 nM to about 100 nM, and most preferably from about 0.3 nM to about 10 nM.

Yet another aspect of this invention is combinations of a compound of Formula I, a prodrug thereof, or a pharmaceutically acceptable salt of said compound or of said prodrug and other compounds as described below.

Accordingly, another aspect of this invention is a method for treating obesity comprising administering to a patient a. an amount of a first compound, said first compound being a Formula I compound, a prodrug thereof, or a pharmaceutically acceptable salt of said compound or of said prodrug; and b. an amount of a second compound, said second compound being a $\beta_3$ agonist, a thyromimetic agent, an eating behavior modifying agent, or an NPY antagonist wherein the amounts of the first and second compounds result in a therapeutic effect.

This invention is also directed to a pharmaceutical combination composition comprising: a therapeutically effective amount of a composition comprising a first compound, said first compound being a Formula I compound, a prodrug thereof, or a pharmaceutically acceptable salt of said compound or of said prodrug a second compound, said second compound being a $\beta_3$ agonist, a thyromimetic agent, an eating behavior modifying agent, or an NPY antagonist; and/or optionally a pharmaceutical carrier, vehicle or diluent.

Another aspect of this invention is a kit comprising:

a. an amount of a Formula I compound, a prodrug thereof, or a pharmaceutically acceptable salt of said compound or of said prodrug and a pharmaceutically acceptable carrier, vehicle or diluent in a first unit dosage form;

b. an amount of a $\beta_3$ agonist, a thyromimetic agent, an eating behavior modifying agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred antiobesity agents (taken singly or in any combination thereof) in the above combination methods, combination compositions and combination kits are described below.

The following are anorectic and/or antiobesity agents: phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotoninergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glycagon-like peptide-1 receptor and ciliary neurotrophic factors such as Axokine.

Another aspect of this invention is a method treating diabetes comprising administering to a patient a. an amount of a first compound, said first compound being a Formula I compound, a prodrug thereof, or a pharmaceutically acceptable salt of said compound or of said prodrug; and b. an amount of a second compound, said second compound being an aldose reductase inhibitor, a glycogen phosphorylase inhibitor, a sorbitol dehydrogenase inhibitor, insulin, metformin, acarbose, a thiazolidinedione such as troglitazone or rezulin, a glitazone such as rosaglitazone or pioglitazone, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a Formula I compound, a prodrug thereof, or a pharmaceutically acceptable salt of said compound or of said prodrug;

a second compound, said second compound being an aldose reductase inhibitor, a glycogen phosphorylase inhibitor, a sorbitol dehydrogenase inhibitor, insulin, metformin, acarbose, a thiazolidinedione such as troglitazone, rezulin, a glitazone such as rosaglitazone or pioglitazone, a sulfonyluree, glipazide, glyburide, or chlorpropamide; and optionally a pharmaceutical carrier, vehicle or diluent.

Another aspect of this invention is a kit comprising:

a. an amount of a Formula I compound, a prodrug thereof, or a pharmaceutically acceptable salt of said compound or of said prodrug and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, insulin, metformin, acarbose, a thiazolidinedione such as troglitazone, rezulin, a glitazone such as rosaglitazone or pioglitazone, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for controlled release.

Formulations for oral use may also be presented as hard gelatin capsules wherein the active ingredients is mixed with an inert solid diluent, for example, calcium carbonate, calcium phosphate or kaolin, or a soft gelatin capsules wherein the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate.

The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, may also be present.

The pharmaceutical compositions of the invention may also be in the form of an oil-in-water emulsions. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of the invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethyleme glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural The invention useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy.

The invention disclosed herein is exemplified by the following preparations and examples which should not be construed to limit the scope of the disclosure. Alternative mechanistic pathways and analogous structures may be apparent to those skilled in the art.

In the preparations and examples, the following abbreviations are used: room temperature (R.T.), phenyl (Ph), -t-butyloxycarbonyl (-Boc), methylamine (MeNH$_2$), sodium triacetoxyborohydride (NaBH(OAc)$_3$), ethyl acetate (EtOAc), methanol (MeOH), triethylamine (Et$_3$N), ether (Et$_2$O), tetrahydrofuran (THF), diisopropylethylamine (iPr$_2$NEt), 1,2 dimethoxyethane (DME), ethanol (EtOH),

Preparation 1

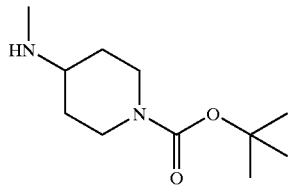

To a mixture of N-t-butoxycarbonyl-4-piperidone (10 g, 50 mmol) and aqueous methylamine (40% w/w, 10 ml) in 1,2-dichloroethane (125 ml) was added NaBH(OAc)$_3$ (16.0 g, 75 mmol). The reaction mixture was stirred overnight, then 1M NaOH (250 ml) was added and the whole was extracted with ether (700 ml). The organic layer was washed with sat'd NaCl, dried (MgSO$_4$), filtered, and concentrated to give the product (10.5 g, 97%) as an oil. $^1$H NMR (CDCl$_3$, 400 MHz) δ 4.09 (2H, m), 2.86 (2H, m), 2.55 (1H, m), 2.50 (3H, s), 1.90 (2H, m), 1.51 (9H, s), 1.30 (2H, m).

Preparation 2

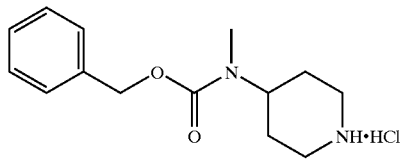

To a stirred solution of Preparation 1 (21.0 g, 83.7 mmol) and Et$_3$N (35 ml, 252 mmol) in CH$_2$Cl$_2$ (300 ml) was added benzyl chloroformate (18 ml, 126 mmol) dropwise. After 5 hr, sat'd NH$_4$Cl (200 ml) was added, and the organic layer was washed with H$_2$O (150 ml) and sat'd NaCl (150 ml), dried (MgSO$_4$), filtered and concentrated. To the residue (32 g) was added 4N HCl in 1,4-dioxane (300 ml), and the mixture was stirred for 4 hr. The reaction mixture was concentrated, acetone was added, and the reaction mixture was again concentrated. The solid residue was dissolved in MeOH (40 ml) and Et$_2$O was added. The resultant precipitate was collected, washed with Et$_2$O, and dried to give the product as a solid (20.2 g, 85%). MS m/e 249 (M+H$^+$, free base).

Preparation 3

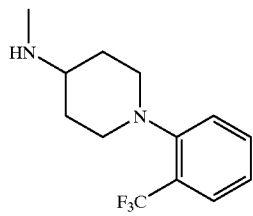

Step 1

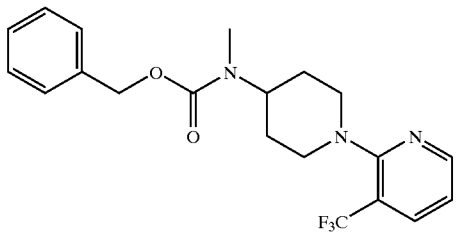

An N$_2$-purged mixture of Preparation 2 (1.03 g, 3.68 mmol), 2-bromo-3-trifluoromethylpyridine (1.60 g, 7.08 mmol), Pd(OAc)$_2$ (48 mg, 0.21 mmol), 1,3-bis-(diphenylphosphino)propane (0.82 g, 0.20 mmol), and sodium-t-butoxide (1.42 g, 14.8 mmol,) in toluene (10 ml) was heated at 100° C. for 3 hr. The reaction mixture was allowed to cool and filtered through celite. The filter pad was washed with CH$_2$Cl$_2$/water, and the organic layer was washed with sat'd NaCl, dried (MgSO$_4$), filtered and concentrated. The residue was subjected to flash chromatography (gradient; CH$_2$Cl$_2$ to 1:99 MeOH/CH$_2$Cl$_2$)to give the product (1.15 g, 80%). MS m/e 394 (M+H)$^+$.

Step 2

A mixture of the product of Step 1 (1.08 g, 2.75 mmol) in EtOH was stirred with 10% Pd/C (0.13 g) under an H$_2$ atmosphere. After one day, the catalyst was removed by filtration through Celite and the volatiles were evaporated to give the product (0.67 g, 94%). MS m/e 260 (M+H)$^+$.

The following compounds were made using essentially the same procedure and the appropriate starting materials:

Preparation 4

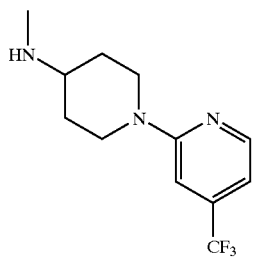

$^1$H NMR (CDCl$_3$, 400 MHz) δ 8.24 (1H, m), 6.8 (1H, s), 6.7 (1H, d), 4.3 (2H, m), 3.0 (2H, m), 2.7 (1H, m), 2.5 (3H, s), 2.0 (2H, m), 1.6 (1H, b), 1.4 (2H, m).

Preparation 5

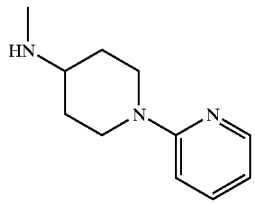

$^1$H NMR (CDCl$_3$, 400 MHz) δ 8.16 (1H, m), 7.43 (1H, m), 6.64 (1H, d, J=8.6 Hz), 6.56 (1H, m), 4.24 (2H, m), 2.90 (2H, m), 2.63 (1H, m), 2.47 (3H, s), 2.39 (1H, b), 2.00 (2H, m), 1.41 (1H, m). MS m/e 192 (M+H)$^+$.

Preparation 6

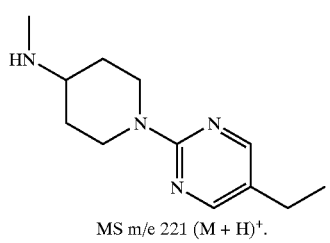

MS m/e 221 (M + H)⁺.

Preparation 7

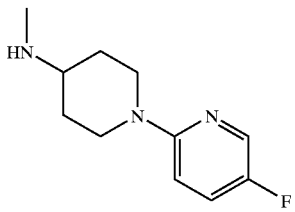

Step 1

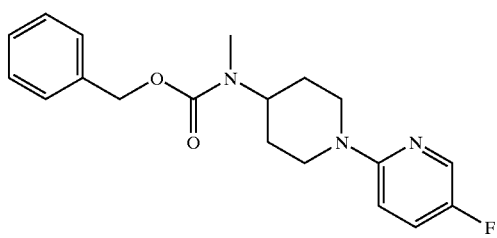

An N₂-purged mixture of Preparation 2 (0.94 g, 11 mmol), 2-Chloro-5-fluoropyridine (0.94 g, 7.2 mmol; Synthesis, 1989, 905–908), Pd(OAc)₂ (64 mg, 0.29 mmol), (di-t-butylphosphino)biphenyl (0.16 mmol 49 mg), sodium-t-butoxide (22.2 mmol, 2.13 g) and toluene (40 ml) was heated at 100° C. for 3 hr. The reaction mixture was allowed to cool then filtered through celite, and the filter pad was washed with EtOAc. The combined filtrate and washings were washed with sat'd NaHCO₃, water and sat'd NaCl, then dried (MgSO₄), filtered and concentrated. The residue was subjected to flash chromatography (gradient; CH₂Cl₂ to 0.5:99.5 MeOH/CH₂Cl₂) to give the product (0.69 g, 28%). MS m/e 344 (M+H)⁺.

Step 2

A mixture of the product of Step 1 (0.69 g, 2.0 mmol) and 10% Pd/C (80 mg) in EtOH (20 ml) was stirred under H₂ for 3 days. The reaction mixture was filtered through celite and the volatiles evaporated to yield the product (0.49 g, 100%) as a solid. ¹H NMR (CDCl₃, 400 MHz) δ 8.0 (1H, m), 7.2 (1H, m), 6.6 (1H, m), 4.2 (2H, m), 2.9 (2H, m), 2.6 (1H, m), 2.5 (3H, s), 2.0 (2H, m), 1.4 (2H, m).

The following compounds were prepared using the appropriate starting materials and essentially the same procedure.

Preparation 8

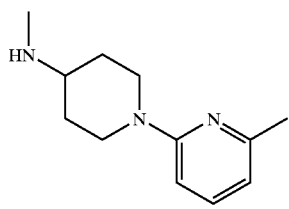

¹H NMR (CDCl₃, 400 MHz) δ 8.2 (1H, m), 7.35 (1H, m), 7.15 (1H, m), 4.25 (2H, m), 2.85 (2H, m), 2.65 (3H, s), 2.6 (1H, m), 2.5 (3H, s), 2.0 (2H, m), 1.9 (1H, b), 1.4 (2H, m).

Preparation 9

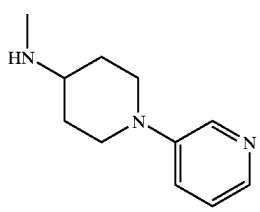

¹H NMR (CDCl₃, 400 MHz) δ 8.29 (1H, s), 8.07 (1H, b), 7.17 (2H, m), 4.2 (1H, b), 3.74 (2H, m), 2.82 (2H, m), 2.74 (3H, s), 1.70 (4H, m). MS m/e 192 (M+H)⁺.

Preparation 10

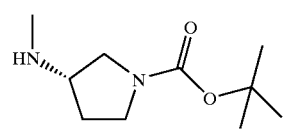

Step 1

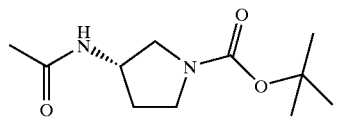

A mixture of (3S)-(–)-3-acetamidopyrrolidine (3.04 g, 23.7 mmol), anhydrous CH₂Cl₂ (50 ml), di-tert-butyl dicarbonate (5.17 g, 23.7 mmol) and Et₃N (0.66 ml, 4.74 mmol) was stirred for 40 min., then partitioned between CH₂Cl₂ (200 ml) and H₂O. The organic layer was dried (Na₂SO₄), filtered and concentrated to give the product (5.17 g, 96%). ¹HNMR (CDCl₃) δ 6.10–5.90 (d, b, 1H), 4.41 (m, 1H), 3.57 (s, b, 1H), 3.38 (m, b., 2H), 3.18 (m, b., 1H), 2.10 (m, 1H), 1.96 (s, 3H), 1.92 (s, b., 1H), 1.44 (s, 9H).

Step 2

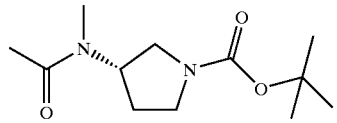

To a solution of the product of Step 1 (5.01 g, 21.9 mmol) in anhydrous THF (100 ml) was added NaH (95%, 0.665 g, 26.3 mmol) and CH₃I (4.1 ml, 66 mmol). The reaction mixture was stirred at R.T. for 16 hr. Additional NaH (60% in mineral oil, 0.263 g, 6.58 mmol) and CH₃I (4.1 ml, 65.8 mmol) were added. The reaction mixture was stirred for an additional 8 hr, quenched with CH₃OH (5 ml) and poured into H₂O (100 ml). The whole was extracted with CH₂Cl₂ (3×200 ml) and the combined organic layers were dried (Na₂SO₄), filtered and evaporated. Subjection of the residue to flash chromatography (1:1 then 2:1 EtOAc/hexane, then 2:98 CH₃OH/CH₂Cl₂) gave the product (5.15 g, 97%). ¹HNMR (CDCl₃) (mixture of rotamers) δ 5.10 (s, b., C-3H), 4.40 (s, b., C-3H), 3.60–3.00 (m, b., 4H), 2.89 (s) & 2.83 (s) (CH₃CO, 3H), 2.14 (s) & 2.09 (s) (CH₃N, 3H), 2.10–2.80 (m, b., 2H), 1.42 (d, 9H). MS m/e 243 (M+H)⁺.

Step 3.

A mixture of the product of Step 2 (2.00 g, 8.26 mmol), CH₃OH (50 ml) and aq. 5N NaOH (6.7 ml) was refluxed for 2.5 days. The reaction mixture was allowed to cool then poured into H₂O (50 ml). The whole was extracted with CH₂CO₂ (5×50 ml), and the combined organic layers were dried (Na₂SO₄), filtered and evaporated to give the product (1.40 g, 85%). ¹HNMR (CDCl₃) a 3.60–3.00 (m, 6H), 2.43 (s, 3H), 2.04 (m, 1H), 1.71 (m, 1H), 1.45 (d, 9H). MS m/e 201 (M+H)⁺.

Preparation 11

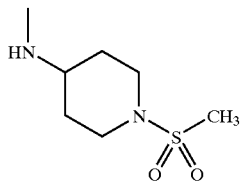

Step 1

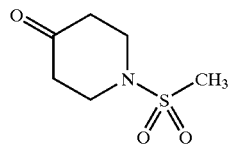

To a stirred solution of 4-piperidone hydrate hydrochloride (40.00 g, 0.260 mol) in THF (320 ml) was added CH₃SO₂Cl (31.0 ml, 0.402 mol) and 15% aq. NaOH (156 ml) such that the reaction temperature was maintained between 26–32° C. After the addition was complete, the reaction was stirred at R.T. for 2 hr and transferred to a separatory funnel. The organic layer was collected and the aqueous layer was extracted with THF (2×250 ml). The combined organic layers were dried (Na₂SO₄). After filtration, the concentrated residue was washed with hexane to give the product (46.00 g, 100%) as a solid. ¹H NMR (CDCl₃) δ 3.59 (t, J=6.00Hz, 4H), 2.89 (s, 3H), 2.59 (t, J=5.6Hz, 4H).

Step 2

A mixture of the product of Step 1 (40.00 g, 0.226 mol), CH₃CN (240 ml), and 40% CH₃NH₂ (20.4 ml, 0.263 mol) was stirred at R.T. for 1 hr. The mixture was slowly added to a –10° C. solution of NaBH(OAC)₃ (60.00 g, 0.283 mol) in CH₃CN (120 ml). After the addition was complete, the reaction was allowed to aftain R.T. After 16 hr the reaction mixture was evaporated to a small volume, and 1N aq. NaOH (282 ml) was added. The resulting solution was extracted with CH₂Cl₂ (3×500 ml), then with toluene. The combined organic layers were dried (Na₂SO₄), filtered and evaporated to give the product (29.00 g, 63%) as a solid. ¹H NMR (CDCl₃) δ 3.66 (m, 2H), 2.84 (m, 2H), 2.76 (s, 3H), 2.52 (m, 1H), 2.42 (s, 3H), 1.96 (m, 2H), 1.45 (m, 2H). MS m/e 193 (M+H)⁺

Preparation 12

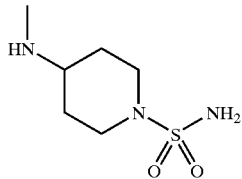

-continued

Step 1

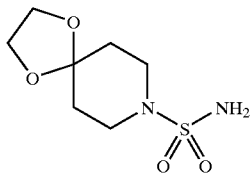

A mixture of 4-piperidone ethylene ketal (0.64 ml, 5.0 mmol) and sulfamide (0.53 g, 5.5 mmol) in DME (20 ml) was refluxed for 16 hr. The mixture was concentrated to ca. 3 ml, dissolved in EtOAc (175 ml), washed with sat'd NH₄Cl (2×25 ml), water (2×25 ml), and brine (25 ml). The organic portion was dried, filtered, and evaporated to give the product (0.58 g, 52%). MS (ES) m/e 223 (M+H)⁺.

Step 2

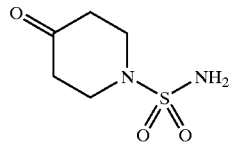

A mixture of the product of Step 1 (560 mg, 2.52 mmol) and pyridinium 4-toluenesulfonate (190 mg, 0.756 mmol) in acetone (25 ml) and water (0.5 ml) was refluxed for 64 hr. The mixture was evaporated to dryness and the residue was partitioned between CH₂Cl₂ (75 ml) and aq. NaHCO₃ (2×20 ml). The aqueous layer was extracted with CH₂Cl₂ and EtOAc sequentially. The EtOAc layer was evaporated to give the product (140 mg). ¹H NMR (CD₃OD, 400 MHz) δ 3.47 (1H, t, J=6.4Hz), 3.15 (3H, m), 2.54 (1H, t, J=6.4Hz), 1.81 (3H, m).

Step 3

A mixture of the product of Step 2 (135 mg, 0.757 mmol), 40% aqueous methylamine (0.3 ml, 2.4 mmol), and NaBH (OAc)₃ (375 mg, 1.77 mmol) in 1,2-dichloroethane (5 ml) was stirred at R.T. for 19 hr. The mixture was partitioned between 3N NaOH (5 ml) and EtOAc (3×50 ml). The organic layer was concentrated to give the crude product (40 mg). The aqueous layer was evaporated to dryness and the residue was suspended in EtOAC. The suspension was filtered and the filtrate concentrated to give another batch of the product (70 mg). MS (FAB) m/e 194 (M+H)⁺.

Preparation 13

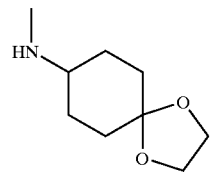

To a stirred mixture of 1,4-Cyclohexanedione monoethylene ketal (4.68 g, 30 mmol) and 40% aq. methylamine (6.0 ml) in 1,2-dichloroethane (75 ml), was added NaBH(OAc)₃ (9.6 g, 45 mmol) in portions. The reaction mixture was vigorously stirred for 16 hr, then 1 N NaOH (75 ml) was added. The organic layer was washed with sat'd NaCl, dried (MgSO₄), filtered, and evaporated to give an oil (4.60 g, 90%) that was used without further purification. ¹H NMR (CDCl₃, 400 MHz) δ 3.97 (4H, s), 2.47 (1H, m), 2.46 (3H, s), 1.91 (2H, m), 1.80 (2H, m), 1.59 (2H, m), 1.45 (2H, m).

EXAMPLE 1

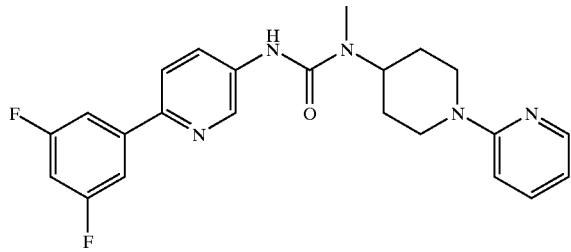

1

Step 1

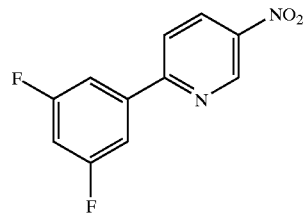

1-1

An N$_2$-purged mixture of 3,5-difluorophenylboronic acid (7.76 g, 24 mmol), 2bromo-5-nitropyridine (2.46 g, 12 mmol), Pd(dppf)Cl$_2$·CH$_2$Cl$_2$ (0.40 g, 0.48 mmol), potassium phosphate (5.06 g, 23.9 mmol) and 1,2-dimethoxyethane (40 ml) was heated in a sealed tube at 80° C. for 5 hr. The reaction mixture was allowed to cool, filtered through celite, and the filtrate was concentrated. The residue was partitioned between sat'd Na$_2$CO$_3$ and EtOAc, and the organic layer was washed with water and sat'd NaCl, dried (MgSO$_4$), filtered and concentrated. Flash chromatography of the residue (1:99 EtOAc/hexane) to gave the product (2.16 g, 76%). MS m/e 237 (M+H)$^+$.

Step 2

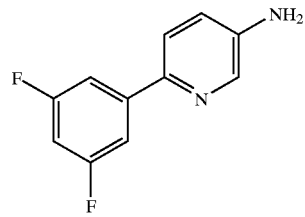

1-2

The product of Step 1 (240 mg, 1.0 mmol), 10% Pd/C (38 mg), and EtOH (25 ml) were stirred under an H$_2$ atmosphere for 3 days. The reaction mixture was filtered through celite and the volatiles were evaporated to give the product (171 mg, 83%). MS m/e 207 (M+H)$^+$.

Step 3

A mixture of the product of Step 2 (145 mg, 0.70 mmol), triphosgene (70 mg, 0.24 mmol), and iPr$_2$NEt (0.61 ml, 3.5 mmol) in toluene (5 ml) was heated at 110° C. for 2 hr. The reaction mixture was allowed to cool and Preparation 5 (140 mg, 0.73 mmol) was added. After 16 hr, the reaction mixture was concentrated, and partitioned between CH$_2$Cl$_2$ (40 ml) and H$_2$O (20 ml). The organic layer was dried (MgSO$_4$), filtered and evaporated. The residue was subjected to PTLC (5:95 MeOH/CH$_2$Cl$_2$) to give the product (148 mg, 50%). $^1$H NMR (CDCl$_3$, 400 MHz) δ 8.51 (1H, d, J=2.8Hz), 8.18 (2H, m), 7.64 (1H, d, J=8.8Hz), 7.50 (3H, m), 6.80 (1H, m), 6.70 (1H, d, J=8.8 Hz), 6.63 (1H, dd, J=7.1, 4.9Hz), 6.54 (1H, s), 4.54 (1H, m), 4.45 (2H, m), 2.94 (2H, m), 2.93 (3H, s), 1.80–1.73 (4H, m). MS (m/e) 424 (M+H)$^+$.

EXAMPLE 2

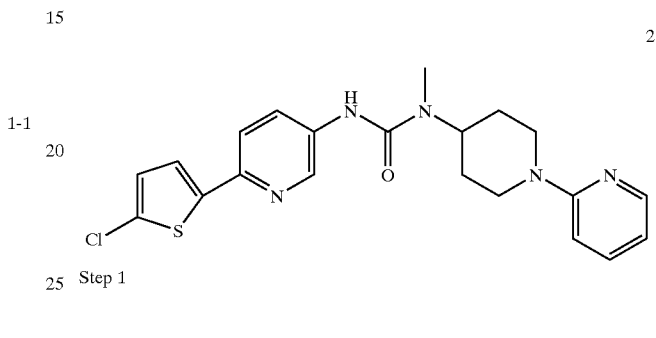

2

Step 1

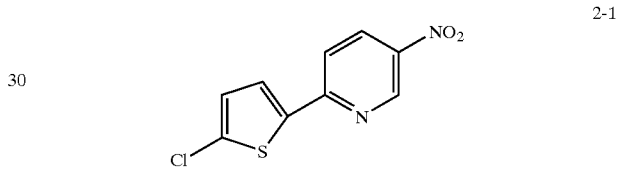

2-1

Reaction of 5-Chlorothiophene-2-boronic acid with 2-Chloro-5-nitropyridine by essentially the procedure of Example 1, Step 1 gave the product. MS m/e 241 (M+H)$^+$.

Step 2

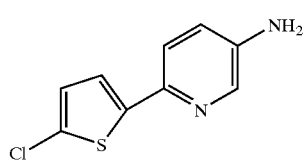

2-2

To an ice-cold suspension of the product of Step 1 (400 mg, 1.66 mmol) and NiCl$_2$·6H$_2$O (790 mg, 3.3 mmol) in MeOH (20 ml) was added NaBH$_4$ (252 mg, 6.67 mmol) in portions. After 20 min., H$_2$O (10 ml) and CH$_2$Cl$_2$ (20 ml) were added, and the whole was filtered through celite. The organic layer was dried (Na$_2$SO$_4$), filtered and concentrated to give a solid (286 mg, 82%). $^1$H NMR (CDCl$_3$, 400 MHz) δ 8.02 (1H, d, J=2.9Hz), 7.38 (1H, d, J=8.4Hz), 7.12 (1H, dd, J=3.8, 0.4Hz), 6.98 (1H, dd, J=8.7, 2.7Hz), 6.85 (1H, dd, J=3.8, 0.4Hz), 3.76 (2H, b).

Step 3

To an ice-cold solution of the product of Step 2 (50 mg, 0.24 mmol) and pyridine (0.06 ml, 0.7 mmol) in THF (5 ml) was added N,N'-disuccinimidyl carbonate (60 mg, 0.24 mmol) and the reaction mixture was allowed to warm to R.T.

After 1 hr, Preparation 5 (52 mg, 0.26 mmol) was added and the reaction mixture was stirred for 2 hr. The reaction mixture was poured into H₂O (20 ml) and extracted with CH₂Cl₂. The organic layer was dried (MgSO₄), filtered and evaporated. The residue was subjected to PTLC (5:95 MeOH/CH₂Cl₂) to give the product (84 mg, 82%). $^1$H NMR (CDCl₃, 400 MHz) δ 8.32 (1H, d, J=2.6Hz), 8.16 (1H, m), 8.03 (1H, dd, J=8.6, 2.1 Hz), 7.46 (1H, d, J=8.6Hz), 7.19 (1H, dd, J=4.0, 0.6Hz), 6.91 (1H, s), 6.86 (1H, dd, J=8.7, 2.7Hz), 6.85 (1H, dd, J=4.0, 0.6Hz), 6.65 (1H, d, J=8.1Hz), 6.60 (1H, m), 4.45 (1H, m), 4.38 (2H, m), 2.87 (2H, m), 2.84 (3H, s), 1.74–1.66 (4H, m).

EXAMPLE 3

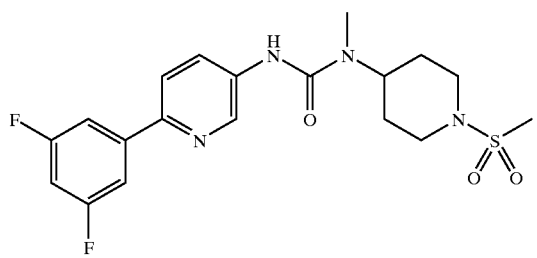

3

Step 1

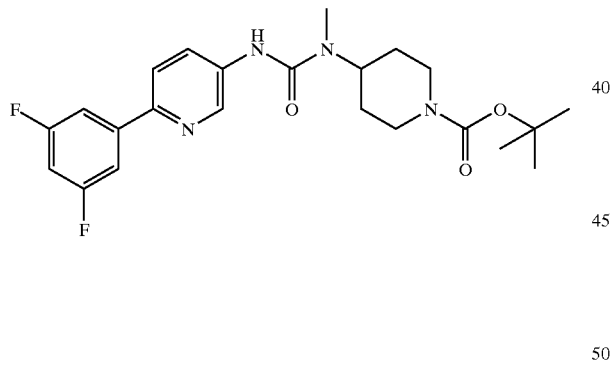

3-1

A mixture of the product from Example 1, Step 2 (1–2) (500 mg, 2.43 mmol), triphosgene (240 mg, 0.81 mmol) and iPr₂NEt (2.1 ml, 12 mmol) in toluene (15 ml) was heated at reflux for 2 hr. The reaction mixture was allowed to cool to R.T. and Preparation 1 (880 mg, 4.1 mmol) was added. The reaction mixture was stirred for 24 hr, diluted with CH₂Cl₂, and washed with sat'd NaHCO₃, H₂O, and sat'd NaCl. The organic layer was dried (Na₂SO₄), filtered and concentrated. Flash chromatography of the residue (gradient; CH₂Cl₂ to 1.5:98.5 MeOH/CH₂Cl₂) gave the product (650 mg, 60%). $^1$H NMR (CDCl₃) δ 8.49 (d, J=2.5Hz, 1H), 8.12 (m, 1H), 7.60 (d, J=8.8Hz, 1H), 7.46 (m, 2H), 6.78 (m, 1H), 6.74 (s, 1H), 4.40 (m, 1H), 4.20 (m, 2H), 2.90 (s, 3H), 2.78 (m, 2H), 1.67–1.55 (m, 4H), 1.45 (s, 9H). MS m/e 447 (M+H)⁺.

Step 2

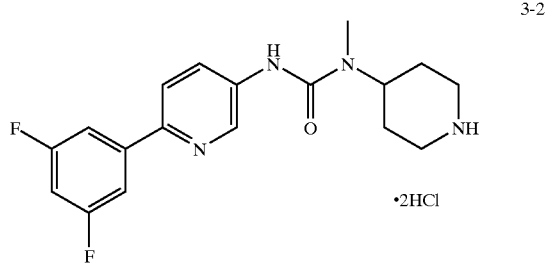

3-2

To a solution of the product of Step 1, 3-1, (510 mg, 1.14 mmol) in THF (15 ml) was added 2N HCl (10 ml). After 6 hr, the volatiles were evaporated and the residue was washed with ether (3×10 ml) to give the product (480 mg, 100%). $^1$H NMR (CD₃OD) δ 9.28 (s, 1H), 8.69 (d, J=8.8Hz, 1H), 8.29 (d, J=8.6Hz, 1H), 7.60 (d, J=5.8Hz, 2H), 7.30 (t, 1H), 4.49 (m, 1H), 3.52 (d, 2H), 3.18 (t, 2H), 3.04 (s, 3H), 2.12 (m, 2H), 1.97 (m, 2H). MS m/e 347 (M+H)⁺.

Step 3

To the product from Step 2 (0.19 mmol, 80mg) in CH₂Cl₂ (2 ml) was added Et₃N (0.7 mmol, 0.1 ml) and methanesulfonyl chloride (0.44 mmol, 50 mg). The reaction was stirred at R.T. for 1 hr, concentrated, and the residue was subjected to PTLC (5:95 MeOH/CH₂Cl₂) to give the product (70 mg, 87%). 1H NMR (CDCl₃, 400 MHz) δ 8.50 (1H, d), 8.15 (1H, m), 7.7 (1H, d), 7.5 (2H, m), 6.8 (1H, m), 6.65 (1H, b), 4.5 (1H, m), 3.95 (2H, m), 3.0 (3H, s), 2.8 (5H, m), 1.8 (4H, m). MS m/e 425 (M+H)⁺.

EXAMPLE 4

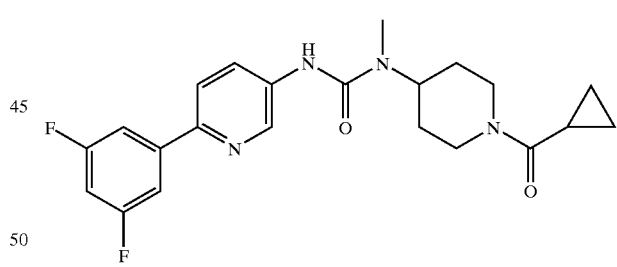

4

To a solution of the amine 3-2 (51 mg, 0.12 mmol) in CH₂Cl₂ (2 ml) was added Et₃N (0.1 ml, 0.7 mmol) and cyclopropylcarbonyl chloride (0.02 ml, 0.2 mmol). The reaction mixture was stirred at R.T. for 40 min. then subjected directly to PTLC (5:95 MeOH/CH₂Cl₂) to give the product (49 mg, 99%). $^1$H NMR (CDCl₃, 400 MHz) δ 8.50 (1H, m), 8.16 (1H, m), 7.65 (1H, m), 7.49 (2H, m), 6.82 (1H, m), 6.57 (1H, b), 4.75 (1H, m), 4.56 (1H, m), 4.32 (1H, b), 3.21 (1H, m), 2.93 (3H, s), 2.66 (1H, m), 1.80 (5H, m), 0.99 (2H, m), 0.77 (2H, m). MS m/e 415 (M+H)⁺.

Using the appropriate reagents and Preparations the following Examples were prepared by essentially the same procedures:

| STRUCTURE | ¹H NMR | MS (M + H)⁺ |
|---|---|---|
| 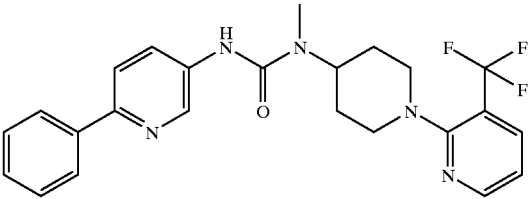<br>1A | (CDCl₃) δ 8.52(d, J=2.5Hz, 1H), 8.43 (m, 1H), 8.17(m, 1H), 7.94(m, 2H), 7.86 (m, 1H), 7.69(d, J=8.6Hz, 1H), 7.45(t, 2H), 7.39(t, 1H), 7.01(m, 1H), 6.60(s, 1H), 4.47(m, 1H), 3.68(d, b, 2H), 3.04(t, 2H), 2.98(s, 3H), 1.87(m, 2H), 1.78(m, 2H). | 456 |
| 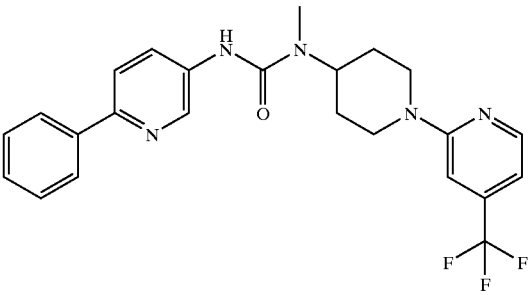<br>1B | (CDCl₃) δ 8.57(d, J=2.5Hz, 1H), 8.30 (m, 1H), 8.18(m, 1H), 7.93(d, 2H), 7.70 (d, 1H), 7.43(t, 2H), 7.39(m, 1H), 6.82(s, 1H), 6.77(m, 1H), 6.58(s, 1H), 4.59(m, 1H), 4.48(m, 2H), 3.01(m, 2H), 2.96(s, 3H), 1.83(m, 2H), 1.70(m, 2H). | 456 |
| 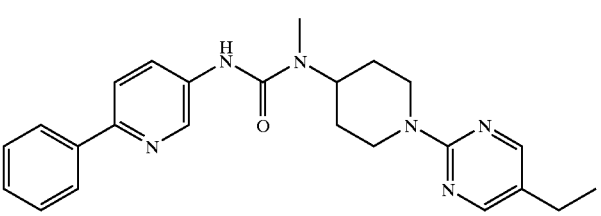<br>1C | (CDCl₃) δ 8.50(d, J=2.6Hz, 1H), 8.17(s, 2H), 8.14(m, 1H), 7.94(m, 2H), 7.68(d, J= 8.8Hz, 1H), 7.44(t, 2H), 7.38(m, 1H), 6.59(s, 1H), 4.86(m, 2H), 4.54(m, 1H), 2.93(m, 2H), 2.89(s, 3H), 2.45(q, 2H), 1.76(m, 2H), 1.64(m, 2H), 1.19(t, 3H). | 417 |
| 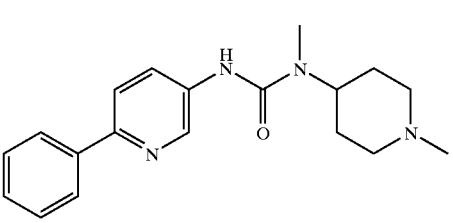<br>1D | (CDCl₃) δ 8.50(d, J=2.7Hz, 1H), 8.10 (m, 1H), 7.91(d, J=7.3Hz, 2H), 7.65(d, J=8.6Hz, 1H), 7.43(t, 2H), 7.37(m, 1H), 6.63(s, 1H), 4.24(m, 1H), 2.94–2.90(m, 5H), 2.28(s, 3H), 2.05(m, 2H), 1.82–1.64 (m, 4H). | 325 |
| 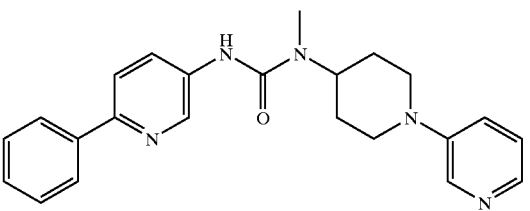<br>1E | (CDCl₃) δ 8.51(d, J=2.7Hz, 1H), 8.32(d, J=1.8Hz, 1H), 8.11(m, 2H), 7.93(d, J= 8.4Hz, 2H), 7.64(d, J=8.8Hz, 1H), 7.45 (t, 2H), 7.38(m, 1H), 7.18(m, 2H), 6.72(s, 1H), 4.46(m, 1H), 3.77(m, 2H), 2.94(s, 3H), 2.89(m, 2H), 1.81(m, 4H). | 388 |
| 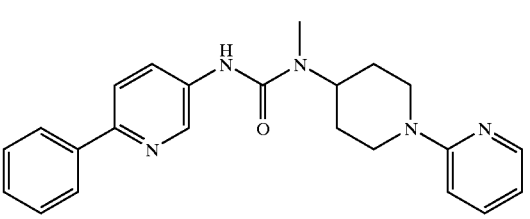<br>1F | (CDCl₃) δ 8.51(d, J=2.2Hz, 1H), 8.19 (m, 1H), 8.15(m, 1H), 7.95(d, J=8.4Hz, 2H), 7.69(d, J=8.4Hz, 1H), 7.50–7.37 (m, 4H), 6.70–6.56(m, 3H), 4.53(m, 1H), 4.43(m, 2H), 2.98–2.90(m, 5H), 1.78–1.71 (m, 4H). | 388 |

| STRUCTURE | ¹H NMR | MS (M + H)⁺ |
|---|---|---|
| 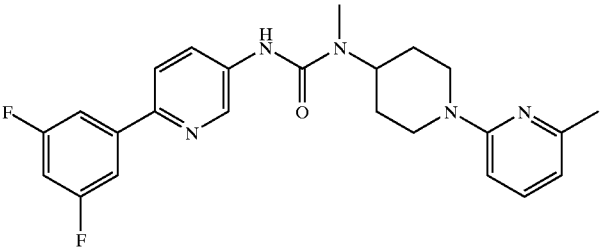<br>1G | (CDCl₃) δ 8.51(m, 1H), 8.17(m, 1H), 7.66 (d, 1H), 7.50(m, 2H), 7.38(t, 1H), 6.80 (m, 1H), 6.49(m, 3H), 4.45(m, 3H), 2.91 (m, 5H), 2.40(s, 3H), 1.83–1.70(m, 4H). | 438 |
| 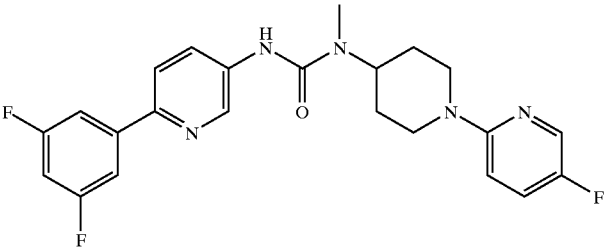<br>1H | (CDCl₃) δ 8.53(m, 1H), 8.18(m, 1H), 8.04 (d, 1H), 7.66(d, 1H), 7.50(m, 2H), 7.26 (m, 1H), 6.80(m, 1H), 6.65(m, 1H), 6.53 (s, 1H), 4.50(m, 1H), 4.29(m, 2H), 2.91 (m, 5H), 1.83–1.67(m, 4H). | 442 |
| 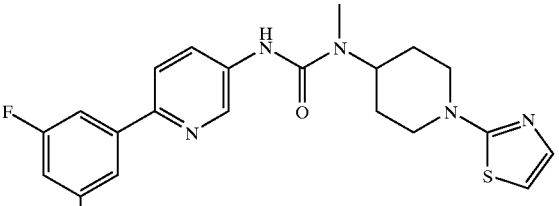<br>1I | (CDCl₃) δ 8.51(m, 1H), 8.14(m, 1H), 7.64 (m, 1H), 7.48(m, 2H), 7.19(m, 1H), 6.80 (m, 1H), 6.58(m, 1H), 6.53(s, 1H), 4.54 (m, 1H), 4.13(m, 2H), 3.13(m, 2H), 2.94 (s, 3H), 1.82(m, 4H). | 430 |
| 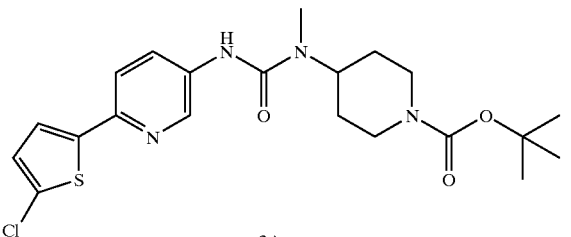<br>2A | (CDCl₃) δ 8.32(d, J=2.2Hz, 1H), 8.08 (m, 1H), 7.50(d, J=8.7Hz, 1H), 7.23(d, J=4.1Hz, 1H), 6.88(d, J=4.0Hz, 1H), 6.58(s, 1H), 4.40(m, 1H), 4.32(m, 2H), 2.90(s, 3H), 2.78(m, 2H), 1.68–1.50(m, 4H), 1.46(s, 9H). | 451 |
| 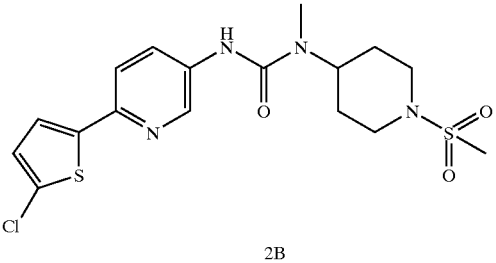<br>2B | (CDCl₃) δ 8.39(d, J=2.4Hz, 1H), 8.07 (m, 1H), 7.52(d, J=8.8Hz, 1H), 7.26(m, 1H), 6.90(d, J=4.0Hz 1H), 6.60(s, 1H), 4.42(m, 1H), 3.92(m, 2H), 2.94(s, 3H), 2.80(m, 5H), 1.84–1.79(m, 4H). | 429 |

-continued

| STRUCTURE | ¹H NMR | MS (M + H)⁺ |
|---|---|---|
| 2C | (CDCl₃) δ 8.38(s, 1H), 8.08(m, 1H), 7.52 (d, J=8.8Hz, 1H), 7.27(m, 1H), 6.90(d, J=3.8Hz, 1H), 6.55(bs, 1H), 4.45(m, 1H), 3.92(m, 2H), 2.94(m, 7H), 1.84–1.76 (m, 4H), 1.37(t, 3H). | 443 |
| 3A | (CDCl₃) δ 8.58(s, b, 1H), 8.10(m, 1H), 7.95(m, 2H), 7.70(m, 1H), 7.43(t, 2H), 7.39(m, 1H), 6.57(s, 1H), 4.42(m, 1H), 3.83(m, 2H), 2.94(s, 3H), 2.82(m, 5H), 1.82(m, 4H). | 389 |
| 3B | (CDCl₃) δ 8.60(s, 1H), 8.15(m, 1H), 7.93 (m, 2H), 7.70(d, J=8.8Hz, 1H), 7.46(t, 2H), 7.39(m, 1H), 6.64(s, b, 1H), 4.47(m, 1H), 3.93(m, 2H), 2.96(m, 7H), 1.80(m, 4H), 1.37(t, 3H). | 403 |
| 3C | (CDCl₃) δ 8.52(d, J=2.6Hz, 1H), 8.10 (m, 1H), 7.93(m, 2H), 7.68(d, J=8.8Hz, 1H), 7.49–7.35(m, 3H), 6.58(s, 1H), 4.46 (m, 1H), 3.95(m, 2H), 3.18(m, 1H), 3.03–2.85(m, 5H), 1.76(m, 4H), 1.33(d, 6H). | 417 |
| 3D | (CDCl₃) δ 8.55(d, J=2.4Hz, 1H), 8.10 (m, 1H), 7.93(m, 2H), 7.68(d, J=8.8Hz, 1H), 7.46–7.36(m, 3H), 6.64(s, 1H), 4.44 (m, 1H), 3.91(m, 2H), 2.93–2.82(m, 7H), 1.86–1.76(m, 6H), 1.06(t, 3H). | 417 |

-continued
| STRUCTURE | ¹H NMR | MS (M + H)⁺ |
|---|---|---|
| 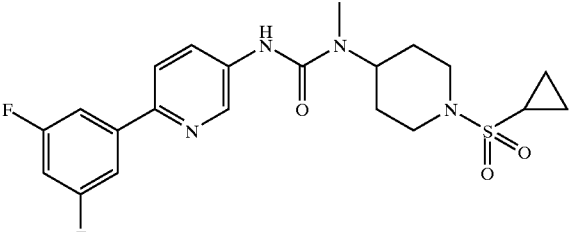<br>3E | (CD₃OD) δ 9.20(d, J=2.4Hz, 1H), 8.53 (m, 1H), 8.25(d, J=9.2Hz, 1H), 7.58(m, 2H), 7.29(m, 1H), 4.30(m, 1H), 3.86(m, 2H), 3.00(m, 5H), 2.50(m, 1H), 1.95–1.78 (m, 4H), 1.05(m, 4H). | 451 |
| 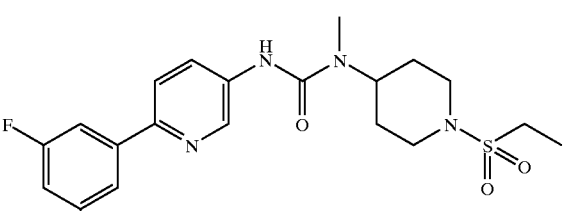<br>3F | (CDCl₃) δ 8.52(d, J=2.4Hz, 1H), 8.12 (m, 1H), 7.63(d, J=8.8Hz, 1H), 7.49(m, 2H), 6.80(m, 1H), 6.59(s, 1H), 4.45(m, 1H), 3.93(m, 2H), 2.93(m, 7H), 1.79(m, 4H), 1.36(t, 3H). | 439 |
| 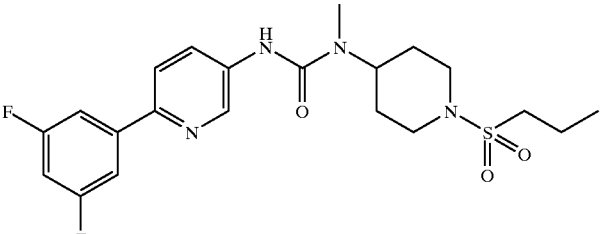<br>3G | (CD₃OD) δ 9.21(d, J=2.4Hz, 1H), 8.55 (m, 1H), 8.25(d, J=9.2Hz, 1H), 7.59(m, 2H), 7.28(m, 1H), 4.30(m, 1H), 3.85(m, 2H), 2.95(m, 7H), 1.81(m, 6H), 1.07(t, 3H). | 453 |
| 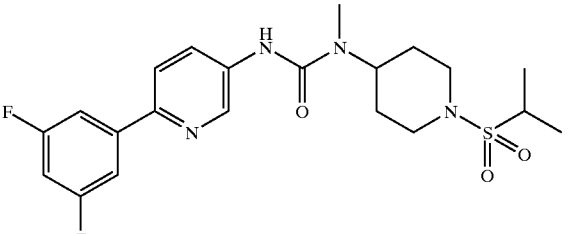<br>3H | (CDCl₃) δ 8.52(d, J=2.4Hz, 1H), 8.13 (m, 1H), 7.63(d, J=8.8Hz, 1H), 7.49(m, 2H), 6.81(m, 1H), 6.57(s, 1H), 4.47(m, 1H), 3.93(m, 2H), 3.18(m, 1H), 2.99(m, 2H), 2.95(s, 3H), 1.78(m, 4H), 1.33(d, 6H). | 453 |
| 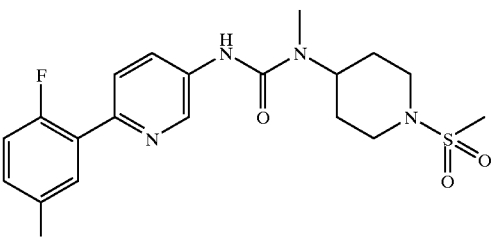<br>3I | (CDCl₃) δ 8.59(d, J=2.4Hz, 1H), 8.07 (m, 1H), 7.78(m, 1H), 7.71(m, 1H), 7.28 (m, 2H), 6.53(s, 1H), 4.44(m, 1H), 3.91 (m, 2H), 2.96(s, 3H), 2.79(m, 5H), 1.82 (m, 4H). | 425 |

-continued
| STRUCTURE | ¹H NMR | MS (M + H)⁺ |
|---|---|---|
| 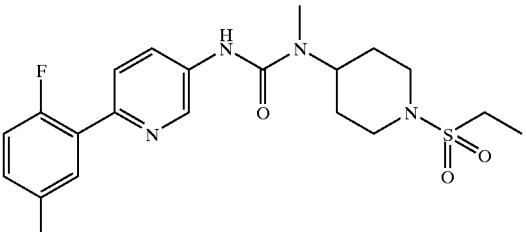<br>3J | (CDCl₃) δ 8.59(d, J=2.4Hz, 1H), 8.06 (m, 1H), 7.78(m, 1H), 7.71(m, 1H), 7.07 (m, 1H), 7.02(m, 1H), 6.54(s, 1H), 4.46 (m, 1H), 3.93(d, J=11.2Hz, 2H), 2.94 (m, 7H), 1.80(m, 4H), 1.37(t, 3H). | 439 |
| 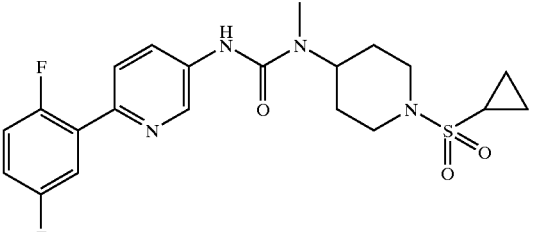<br>3K | (CDCl₃) δ 8.60(s, 1H), 8.06(m, 1H), 7.77 (d, J=7.2Hz, 1H), 7.68(m, 1H), 7.07(m, 1H), 7.01(m, 1H), 6.66(s, 1H), 4.43(s, 1H), 3.90(d, 2H), 2.91(m, 5H), 2.60(m, 1H), 1.78(m, 4H), 1.15(m, 2H), 1.00(m, 2H). | 451 |
| 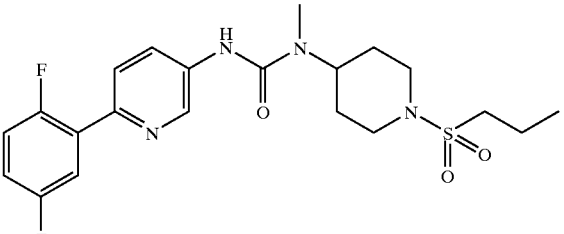<br>3L | (CDCl₃) δ 8.61(s, 1H), 8.06(m, 1H), 7.78 (d, J=6.8Hz, 1H), 7.71(m, 1H), 7.07(m, 1H), 7.01(m, 1H), 6.64(s, 1H), 4.44(m, 1H), 3.91(d, J=12.4Hz, 2H), 2.93(s, 3H), 2.86(m, 4H), 1.82(m, 6H), 1.06(t, 3H). | 453 |
| 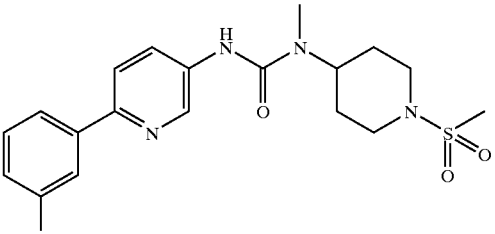<br>3N | (CD₃OD) δ 9.20(m, 1H), 8.55(m, 1H), 8.25(m, 1H), 7.71(m, 3H), 7.41(m, 1H), 4.29(m, 1H), 3.85(m, 2H), 3.01(s, 3H), 2.87(m, 5H), 1.94–1.76(m, 4H). | 407 |
| 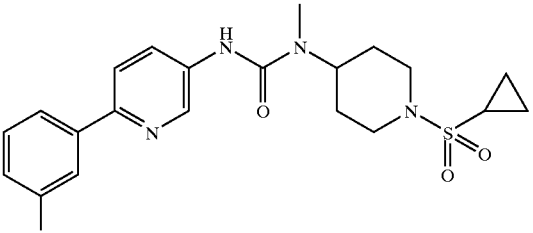<br>3O | (CDCl₃) δ 8.52(d, J=2.5Hz, 1H), 8.12 (m, 1H), 7.71(m, 3H), 7.38(m, 1H), 7.07 (m, 1H), 6.47(m, 1H), 4.43(s, 1H), 3.92 (d, 2H), 2.96(m, 5H), 2.28(m, 1H), 1.81 (m, 4H), 1.17(m, 2H), 1.00(m, 2H). | 433 |

| STRUCTURE | ¹H NMR | MS (M + H)⁺ |
|---|---|---|
| 4A | (CDCl₃) δ 8.51(d, J=2.6Hz, 1H), 8.13 (m, 1H), 7.93(d, J=7.3Hz, 2H), 7.68(d, J=8.6Hz, 1H), 7.45(t, 2H), 7.38(m, 1H), 6.61(s, 1H), 4.42(m, 1H), 4.20(m, 2H), 2.91(s, 3H), 2.79(m, 2H), 1.76–1.55(m, 4H), 1.45(s, 9H). | 411 |
| 4B | (CDCl₃) δ 8.69(d, J=5.3Hz, 2H), 8.55(d, J=2.7Hz, 1H), 8.14(m, 1H), 7.62(d, J=8.6Hz, 1H), 7.47(m, 2H), 7.28(m, 2H), 6.95(s, 1H), 6.79(m, 1H), 4.82(m, 1H), 4.56(m, 1H), 3.68(m, 1H), 3.17(m, 1H), 2.94(s, 3H), 2.85(m, 1H), 1.90–1.45(m, 4H). | 452 |
| 4C | (CDCl₃) δ 8.68(m, 2H), 8.55(m, 1H), 8.12 (m, 1H), 7.78(m, 1H), 7.64(d, J=8.6Hz, 1H), 7.47(m, 2H), 7.37(m, 1H), 6.82(m, 1H), 6.65(s, 1H), 4.86(m, 1H), 4.59(m, 1H), 3.82(m, 1H), 3.22(m, 1H), 2.96(s, 3H), 2.85(m, 1H), 1.90–1.45(m, 4H). | 452 |
| 4D | (CDCl₃) δ 8.50(d, J=2.8Hz, 1H), 8.12 (m, 1H), 7.62(d, J=8.8Hz, 1H), 7.45(m, 2H), 6.80(m, 2H), 4.75(m, 1H), 4.50(m, 1H), 3.90(m, 1H), 3.18(m, 1H), 2.90(s, 3H), 2.59(m, 1H), 2.11(s, 3H), 1.80–1.56 (m, 4H). | 389 |
| 4E | (CDCl₃) δ 8.50(d, J=2.0Hz, 1H), 8.13 (m, 1H), 7.62(d, J=8.8Hz, 1H), 7.46(m, 2H), 6.78(m, 2H), 4.76(m, 1H), 4.51(m, 1H), 3.92(m, 1H), 3.11(m, 1H), 2.90(s, 3H), 2.59(m, 1H), 2.35(q, 2H), 1.76–1.54 (m, 4H), 1.15(m, 3H). | 403 |

-continued
| STRUCTURE | $^1$H NMR | MS (M + H)$^+$ |
|---|---|---|
| 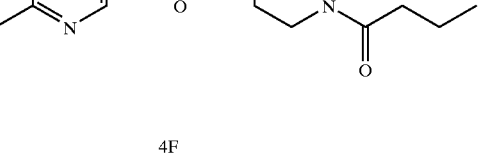<br>4F | (CD$_3$OD) δ 9.26(d, J=2.4Hz, 1H), 8.59 (m, 1H), 8.29(d, J=8.8Hz, 1H), 7.60(m, 2H), 7.32(m, 1H), 4.70(m, 1H), 4.39(m, 1H), 4.10(m, 1H), 3.21(m, 1H), 2.98(s, 3H), 2.71(m, 1H), 2.42(m, 2H), 1.79–1.62 (m, 6H), 0.99(m, 3H). | 417 |
| 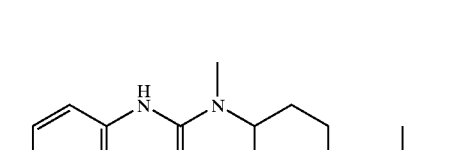<br>4G | (CDCl$_3$) δ 8.50(d, J=2.4Hz, 1H), 8.15 (m, 1H), 7.61(d, J=8.4Hz, 1H), 7.47(m, 2H), 6.87(s, 1H), 6.78(m, 1H), 4.76(m, 1H), 4.50(m, 1H), 4.05(m, 1H), 3.11(m, 1H), 2.90(s, 3H), 2.80(m, 1H), 2.59(m, 1H), 1.82–1.54(m, 4H), 1.13(m, 6H). | 417 |
| 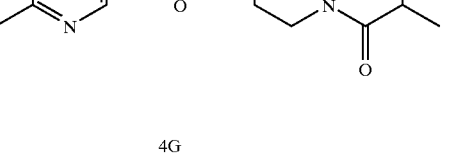<br>4H | (CDCl$_3$) δ 8.50(d, J=2.4Hz, 1H), 8.14 (m, 1H), 7.66(d, J=6.4Hz, 1H), 7.49(m, 2H), 6.81(m, 1H), 6.49(s, 1H), 4.76(m, 2H), 4.12(m, 1H), 3.25(m, 1H), 2.95(s, 3H), 2.86(m, 1H), 1.89–1.60(m, 4H). | 443 |
| 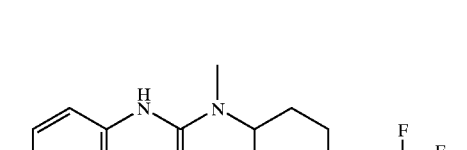<br>4I | (CDCl$_3$) δ 8.50(d, J=2.0Hz, 1H), 8.13 (m, 1H), 7.62(d, J=8.4Hz, 1H), 7.46(m, 2H), 6.80(m, 2H), 4.70(m, 1H), 4.52(m, 1H), 4.10(q, 2H), 3.94(m, 1H), 3.42(s, 3H), 3.10(m, 1H), 2.90(s, 3H), 2.64(m, 1H), 1.79–1.57(m, 4H). | 419 |
| 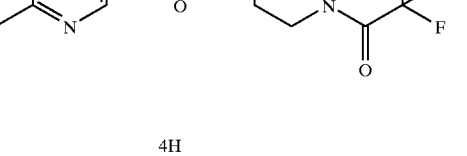<br>4J | (CDCl$_3$) δ 8.50(d, J=2.4Hz, 1H), 8.12 (m, 1H), 7.64(d, J=8.8Hz, 1H), 7.47(m, 2H), 6.80(m, 1H), 6.67(s, 1H), 4.79(m, 1H), 4.56(m, 1H), 3.86(m, 1H), 3.24(m, 3H), 2.96(s, 3H), 2.67(m, 1H), 1.85–1.59 (m, 4H). | 457 |

-continued
| STRUCTURE | ¹H NMR | MS (M + H)⁺ |
|---|---|---|
| 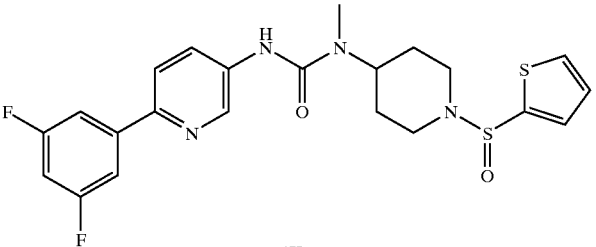<br>4K | (CDCl₃) δ 8.50(d, J=2.4Hz, 1H), 8.15 (m, 1H), 7.63(d, J=8.8Hz, 1H), 7.46(m, 3H), 7.30(d, 1H), 7.03(m, 1H), 6.80(m, 2H), 4.59(m, 3H), 3.06(m, 2H), 2.93(s, 3H), 1.81–1.64(m, 4H) | 457 |
| 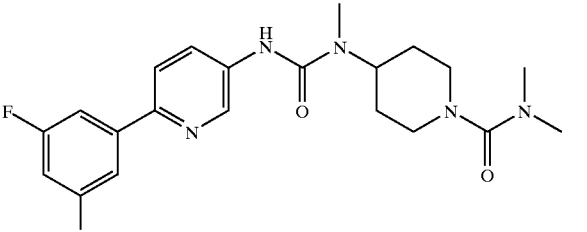<br>4L | (CDCl₃) δ 8.49(d, J=2.0Hz, 1H), 8.15 (m, 1H), 7.62(d, J=8.8Hz, 1H), 7.47(m, 2H), 6.80(m, 1H), 6.69(s, 1H), 4.42(m, 1H), 3.77(m, 2H), 2.92–2.83(m, 11H), 1.68(m, 4H). | 418 |
| 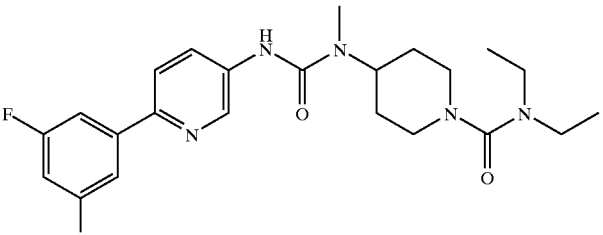<br>4M | (CDCl₃) δ 8.50(d, J=2.4Hz, 1H), 8.14 (m, 1H), 7.61(d, J=8.0Hz, 1H), 7.45(m, 2H), 6.80(m, 2H), 4.40(m, 1H), 3.72(m, 2H), 3.20(m, 4H), 2.90(s, 3H), 2.84(m, 2H), 1.70(m, 4H), 1.11(m, 6H). | 446 |
| 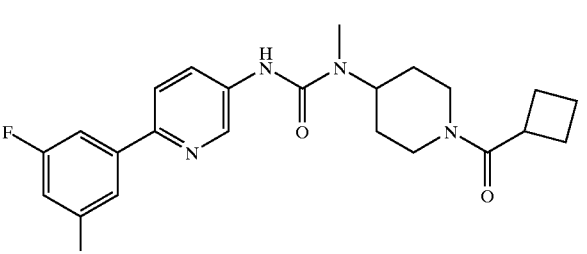<br>4N | (CDCl₃) δ 8.50(d, J=2.4Hz, 1H), 8.15 (m, 1H), 7.62(d, J=8.8Hz, 1H), 7.45(m, 2H), 6.79(m, 2H), 4.76(m, 1H), 4.50(m, 1H), 3.78(m, 1H), 3.26(m, 1H), 3.04(m, 1H), 2.90(s, 3H), 2.60(m, 1H), 2.35–2.13 (m, 4H), 1.99–1.42(m, 6H). | 429 |
| 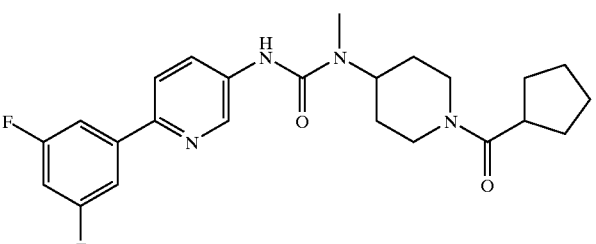<br>4O | (CDCl₃) δ 8.50(d, J=2.8Hz, 1H), 8.15 (m, 1H), 7.64(d, J=8.8Hz, 1H), 7.49(m, 2H), 6.80(m, 1H), 6.54(s, 1H), 4.80(m, 1H), 4.54(m, 1H), 4.06(m, 1H), 3.13(m, 1H), 2.90(m, 4H), 2.61(m, 1H), 1.82–1.55 (m, 12H). | 443 |

-continued

| STRUCTURE | ¹H NMR | MS (M + H)⁺ |
|---|---|---|
| 4P | (CDCl₃) δ 8.50(d, J=2.8Hz, 1H), 8.15 (m, 1H), 7.63(d, J=8.8Hz, 1H), 7.46(m, 2H), 6.79(m, 2H), 4.74(m, 1H), 4.52(m, 1H), 4.00(m, 1H), 3.11(m, 1H), 2.91(s, 3H), 2.52(m, 2H), 1.79–1.24(m, 14H). | 457 |
| 4Q | (CDCl₃) δ 8.50(m, 1H), 8.15(m, 1H), 7.64 (d, J=8.8Hz, 1H), 7.49(m, 3H), 7.33–7.19(m, 2H), 6.80(m, 1H), 6.50(s, 1H), 4.91(m, 1H), 4.58(m, 1H), 3.50(m, 1H), 3.21(m, 1H), 2.94(s, 3H), 2.86(m, 1H), 1.87–1.67(m, 4H). | 519 |
| 4R | (CDCl₃) δ 8.50(m, 1H), 8.15(m, 1H), 7.83 (m, 1H), 7.65(d, J=8.8Hz, 1H), 7.50(m, 2H), 7.41(m, 1H), 7.24(m, 1H), 7.10(m, 1H), 6.80(m, 1H), 6.48(s, 1H), 4.92(m, 1H), 4.60(m, 1H), 3.50(m, 1H), 3.21(m, 1H), 2.96(s, 3H), 2.85(m, 1H), 1.98–1.50 (m, 4H). | 577 |
| 4S | (CDCl₃) δ 8.74(d, J=2.4Hz, 1H), 8.58 (m, 1H), 8.50(d, J=2.0Hz, 1H), 8.15(m, 1H), 7.92(m, 1H), 7.66(d, J=8.4Hz, 1H), 7.50(m, 2H), 6.80(m, 1H), 6.50(s, 1H), 4.86(m, 1H), 4.62(m, 1H), 3.80(m, 1H), 3.21(m, 1H), 2.97(s, 3H), 2.88(m, 1H), 1.94–1.70(m, 4H). | 530 532 |
| 4T | (CDCl₃) δ 8.50(d, J=2.4Hz, 1H), 8.14 (m, 1H), 7.64(d, J=8.8Hz, 1H), 7.50(m, 2H), 7.35(d, 1H), 6.99(d, 1H), 6.80(m, 1H), 6.60(s, 1H), 4.80(m, 1H), 4.60(m, 1H), 3.80(m, 1H), 3.21(m, 2H), 2.94(s, 3H), 1.77(m, 4H). | 535 537 |

-continued
| STRUCTURE | ¹H NMR | MS (M + H)+ |
|---|---|---|
| 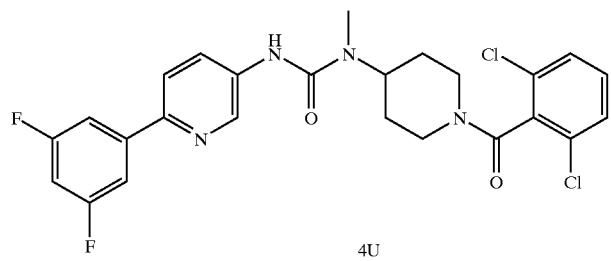<br>4U | (CDCl₃) δ 8.51(m, 1H), 8.10(m, 1H), 7.62 (d, J=8.4Hz, 1H), 7.47(m, 2H), 7.33(m, 2H), 7.25(m, 1H), 6.84(s, 1H), 6.77(m, 1H), 4.92(m, 1H), 4.56(m, 1H), 3.41(m, 1H), 3.20(m, 1H), 2.90(s, 3H), 2.87(m, 1H), 1.83–1.67(m, 4H). | 519 |
| 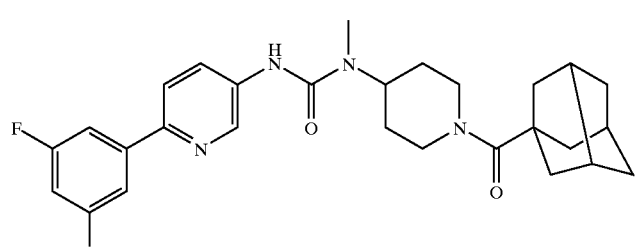<br>4V | (CDCl₃) δ 8.50(d, J=2.4Hz, 1H), 8.13 (m, 1H), 7.62(d, J=8.4Hz, 1H), 7.46(m, 2H), 6.83(s, 1H), 6.78(m, 1H), 4.64(m, 2H), 4.52(m, 1H), 2.89(s, 3H), 2.84(m, 2H), 2.04–1.54(m, 19H). | 509 |
| 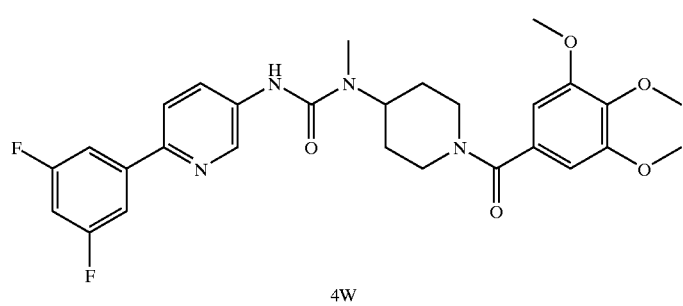<br>4W | (CDCl₃) δ 8.52(m, 1H), 8.15(m, 1H), 7.63 (d, J=8.8Hz, 1H), 7.48(m, 2H), 6.80(m, 1H), 6.69(s, 1H) 6.63(m, 2H), 4.82(m, 1H), 4.56(m, 1H), 3.86(m, 10H), 3.15(m, 1H), 2.94(m, 4H), 1.76(m, 4H). | 541 |
| 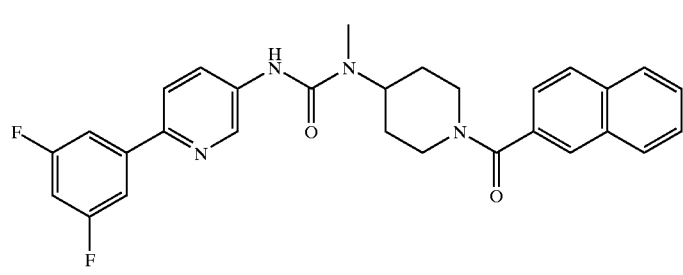<br>4X | (CDCl₃) δ 8.51(m, 2H), 8.15(m, 1H), 7.92 (m, 3H), 7.65(m, 2H), 7.50(m, 4H), 6.80 (m, 1H), 6.51(s, 1H), 4.92(m, 1H), 4.60 (m, 1H), 3.98(m, 1H), 3.21(m, 1H), 2.97 (m, 4H), 1.88–1.50(m, 4H). | 501 |
| 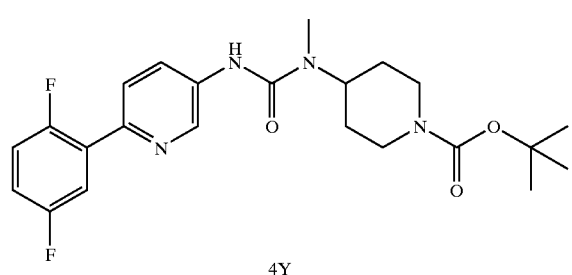<br>4Y | (CDCl₃) δ 8.57(d, J=2.8Hz, 1H), 8.11 (m, 1H), 7.80(m, 1H), 7.74(m, 1H), 7.08 (m, 1H), 7.01(m, 1H), 6.50(s, 1H), 4.44 (m, 1H), 4.22(m, 2H), 2.92(s, 3H), 2.81 (m, 2H), 1.71–1.57(m, 4H), 1.47(s, 9H). | 447 |

-continued

| STRUCTURE | ¹H NMR | MS (M + H)⁺ |
|---|---|---|
| 4Z | (CD₃OD) δ 9.30(d, J=2.4Hz, 1H), 9.09 (s, 1H), 8.97(d, J=5.6Hz, 1H), 8.74(d, J=8.4Hz, 1H), 8.65(m, 1H), 8.19(m, 2H), 7.62(m, 1H), 7.45(m, 2H), 4.80(m, 1H), 4.50(m, 1H), 3.76(m, 1H), 4.46(m, 1H), 3.38(m, 1H), 3.04(s, 4H), 2.00–1.65(m, 4H). | 452 |
| 4AA | (CDCl₃) δ 8.57(m, 1H), 8.10(m, 1H), 7.79 (d, J=7.6Hz, 1H), 7.71(m, 1H), 7.08(m, 1H), 7.01(m, 1H), 6.52(s, 1H), 4.75(m, 1H), 4.56(m, 1H), 4.33(m, 1H), 3.21(m, 1H), 2.91(s, 3H), 2.66(m, 1H), 1.82–1.62 (m, 5H), 0.99(m, 2H), 0.78(m, 2H). | 415 |
| 4BB | (CDCl₃) δ 8.57(d, J=2.8Hz, 1H), 8.09 (m, 1H), 7.78(d, J=8.0Hz, 1H), 7.69(m, 1H), 7.07(m, 1H), 7.01(m, 1H), 6.64(s, 1H), 4.47(m, 1H), 4.53(m, 1H), 3.94(m, 1H), 3.13(t, 1H), 2.91(s, 3H), 2.60(t, 1H), 2.33(t, 2H), 1.78–1.54(m, 6H), 0.96(t, 3H). | 417 |
| 4CC | (CD₃OD) δ 8.29(d, J=2.0Hz, 1H), 8.60 (m, 1H), 8.19(d, J=9.2Hz, 1H), 7.61(m, 1H), 7.45(m, 2H), 4.70(m, 1H), 4.41(m, 1H), 4.18(m, 1H), 3.21(m, 1H), 2.93(s, 4H), 2.69(m, 1H), 1.77(m, 4H), 1.14–1.09 (m, 6H). | 417 |
| 4DD | (CDCl₃) δ 8.57(s, 1H), 8.08(m, 1H), 7.76 (d, J=6.8Hz, 1H), 7.68(m, 1H), 7.10(m, 1H), 7.02(m, 1H), 6.80(s, 1H), 4.75(d, 1H), 4.51(m, 1H), 3.88(d, 1H), 3.16(t, 1H), 2.90(s, 3H), 2.59(t, 1H), 2.11(s, 3H), 1.80–1.56(m, 4H). | 389 |

-continued

| STRUCTURE | ¹H NMR | MS (M + H)⁺ |
|---|---|---|
| 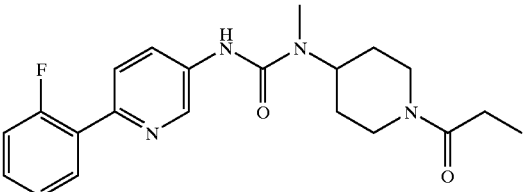 4EE | (CDCl₃) δ 8.56(s, 1H), 8.08(d, J=8.8Hz, 1H), 7.77(d, J=7.2Hz, 1H), 7.68(m, 1H), 7.08(m, 1H), 7.01(m, 1H), 6.72(s, 1H), 4.77(d, 1H), 4.51(m, 1H), 3.94(d, 1H), 3.11(t, 1H), 2.90(s, 3H), 2.60(t, 1H), 2.34(q, 2H), 1.80–1.54(m, 4H), 1.15(t, 3H). | 403 |
| 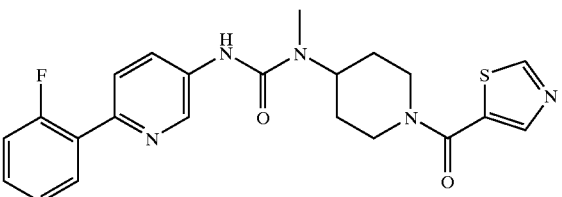 4FF | (CDCl₃) δ 8.89(s, 1H), 8.62(s, 1H), 8.12 (m, 1H), 8.07(s, 1H), 7.80(d, J=6.4Hz, 1H), 7.70(m, 1H), 7.11(m, 1H), 7.01(m, 1H), 6.64(bs, 1H), 4.80–4.20(m, 3H), 3.35–2.80(m, 5H), 1.86–1.69(m, 4H). | 459 |

EXAMPLE 5

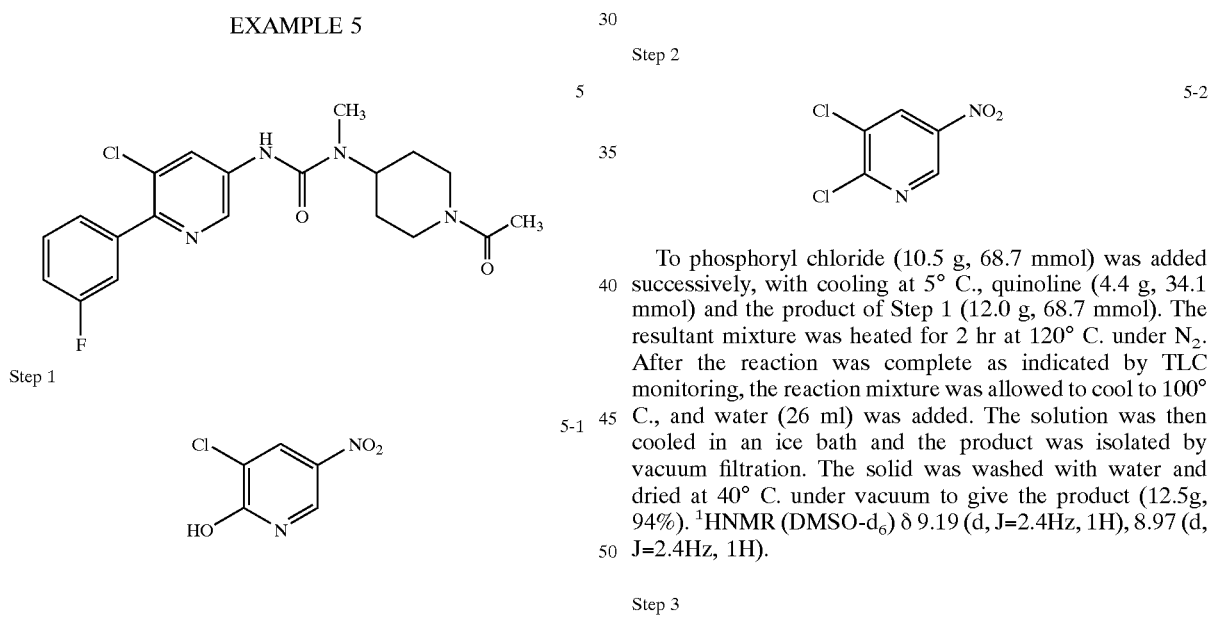

Step 1

A solution of 2-hydroxy-5-nitropyridine (11.2 g, 79.9 mmol) in conc. HCl (57 ml) was warmed to 50° C. and KClO₃ (3.4 g, 27.7 mmol) in water (50 ml) was added dropwise at such a rate that the temperature was kept below 60° C. During the addition the product began to separate. After TLC monitoring indicated complete consumption of starting material the mixture was cooled to 0° C. and the product was isolated by vacuum filtration. The solid was washed with water and dried at 50° C. under vacuum to give the product (12.3g, 88%) as a solid. ¹HNMR (DMSO-d₆) δ 8.68 (d, J=3.2Hz, 1H), 8.40 (d, J=3.2Hz, 1H). MS m/e 175 (M+H)⁺.

Step 2

To phosphoryl chloride (10.5 g, 68.7 mmol) was added successively, with cooling at 5° C., quinoline (4.4 g, 34.1 mmol) and the product of Step 1 (12.0 g, 68.7 mmol). The resultant mixture was heated for 2 hr at 120° C. under N₂. After the reaction was complete as indicated by TLC monitoring, the reaction mixture was allowed to cool to 100° C., and water (26 ml) was added. The solution was then cooled in an ice bath and the product was isolated by vacuum filtration. The solid was washed with water and dried at 40° C. under vacuum to give the product (12.5g, 94%). ¹HNMR (DMSO-d₆) δ 9.19 (d, J=2.4Hz, 1H), 8.97 (d, J=2.4Hz, 1H).

Step 3

A flask charged with 3-fluorophenylboronic acid (1.63 g, 11.65 mmol), the product of Step 2 (1.50 g, 7.77 mmol), ethylene glycol dimethyl ether (18 ml) and potassium phosphate (4.95 g, 23.3 mmol) was purged with N₂. PdCl₂(dppf)

.CH₂Cl₂ (0.26 g, 0.32 mmol) was added. The reaction mixture was heated at 80° C. under N₂ for 2 hr, allowed to cool, and filtered through celite. The filtrate was extracted with EtOAc (60 ml) was then washed with saturated sodium carbonate (40 ml), water (40 ml), brine (30 ml), dried (Na₂SO₄), filtered and concentrated. The residue was subjected to flash chromatography (1:5 CH₂Cl₂/hexane) to give the product (1.96 g, 100%). ¹HNMR (CDCl₃) δ 9.39 (d, J=2.4Hz, 1H), 8.62 (d, J=2.4Hz, 1H), 7.62 (m, 1H), 7.54 (m, 2H), 7.22 (m, 1H). MS m/e 253 (M+H)⁺.

Step 4

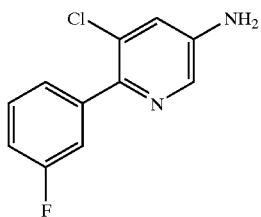

5-4

To an ice-cold solution of the product of Step 3 (2.25 g, 8.9 mmol) and nickel chloride hexahydrate (4.23 g, 17.8 mmol) in MeOH (100 ml) was added sodium borohydride (1.11 g, 29.5 mmol) in portions. The resulting mixture was stirred at 0–5° C. for 30 min., water (5 ml) was added and the whole was concentrated. The residue was treated with EtOAc (100 ml) and filtered through celite. The filtrate was dried (MgSO₄), filtered and concentrated to give the product (2.3 g). ¹HNMR (CDCl₃) δ 7.53 (s, 1H), 6.97 (m, 1H), 6.84 (m, 2H), 6.63 (s, 1H), 6.53 (m, 1H), 3.90 (s, b, 2H).

Step 5

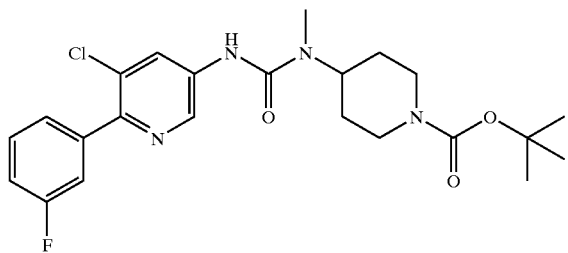

5-5

To a solution of the product of Step 4 (500 mg, 2.25 mmol) in anhydrous pyridine (6 ml) was added phenyl chloroformate (390 mg, 2.49 mmol) dropwise. The reaction mixture was stirred for 16 hr then evaporated in vacuo. The residue was taken up in chloroform (10 ml), and Et₃N (1 ml) and Preparation 1 (722 mg, 3.37 mmol) was added. The mixture was heated at 65° C. for 3 hr. The residue was allowed to cool, diluted with CH₂Cl₂ (50 ml) and washed with sat'd NaHCO₃ (30 ml), water (30 ml), and NaCl (30 ml). The organic layer was dried (MgSO₄), filtered and evaporated. The residue was subjected to flash chromatography (2:98 CH₃OH/CH₂Cl₂) to give the product (530 mg, 51%). ¹H NMR (CDCl₃) δ 8.41 (d, J=2.4 Hz, 1H), 8.28 (d, J=2.4Hz, 1H), 7.50 (m, 1H), 7.42 (m, 2H), 7.10 (m, 1H), 6.61 (s, 1H), 4.41 (m, 1H), 4.22 (m, 2H), 2.92 (s, 3H), 2.80 (m, 2H), 1.70–1.57 (m, 4H), 1.45 (s, 9H).

Step 6

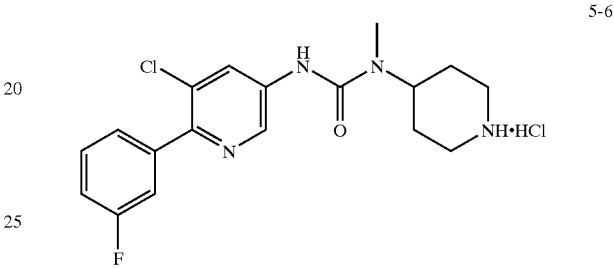

5-6

The product of Step 5 (90 mg, 0.194 mmol) was treated with 4N HCl/1,4-dioxane (4 ml) for 16 hr. The reaction mixture was concentrated and the residue was triturated with Et₂O and dried to give the product (85 mg) as a solid. ¹HNMR (CD₃OD) δ 8.92 (d, J=2.4Hz, 1H), 8.50 (d, J=2.4Hz, 1H), 7.58 (m, 1H), 7.51 (m, 2H), 7.30 (m, 1H), 4.45 (m, 1H), 3.50 (m, 2H), 3.16 (m, 2H), 3.02 (s, 3H), 2.10–1.90 (m, 4H).

Step 7

To a solution of the product of Step 6 (42 mg, 0.096 mmol) and Et₃N (0.2 ml) in CH₂Cl₂ (2 ml) was slowly added acetic anhydride (112 mg, 1.10 mmol). The reaction mixture was stirred at R.T. for 2 hr. The concentrated residue was separated by PTLC (1:20 CH₃OH/CH₂Cl₂) to give the product (31 mg, 80%). ¹HNMR (CDCl₃) δ 8.44 (d, J=2.4Hz, 1H), 8.27 (d, J=2.4Hz, 1H), 7.50 (m, 1H), 7.42 (m, 2H), 7.10 (m, 1H), 6.92 (s, 1H), 4.75 (m, 1H), 4.50(m, 1H), 3.92 (m, 1H), 3.17 (t, 1H), 2.90 (s, 3H), 2.60 (m, 1H), 2.11 (s, 3H), 1.81–1.60 (m, 4H). MS m/e 405 (M+H)⁺.

Use of the appropriate reagents and procedures afforded the following compounds:

| STRUCTURE | ¹H NMR | MS (M + H)⁺ |
|---|---|---|
| 5A | (CDCl₃) δ 8.44(d, J=2.4Hz, 1H), 8.24 (d, J=2.4Hz, 1H), 7.49(m, 1H), 7.43 (m, 2H), 7.10(m, 1H), 6.65(s, 1H), 4.43 (m, 1H), 3.92(m, 2H), 2.93(s, 3H), 2.78 (m, 5H), 1.81(m, 4H). | 441 |

-continued
| STRUCTURE | ¹H NMR | MS (M + H)⁺ |
|---|---|---|
| 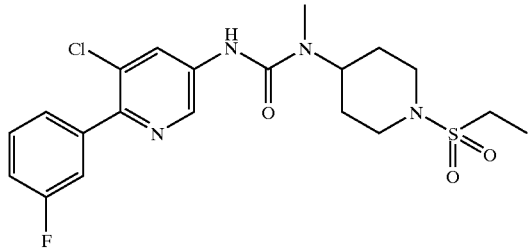<br>5B | (CDCl₃) δ 8.44(d, J=2.4Hz, 1H), 8.25 (d, J=2.4Hz, 1H), 7.50(m, 1H), 7.41 (m, 2H), 7.10(m, 1H), 6.61(s, 1H), 4.44 (m, 1H), 3.93(m, 2H), 2.93(m, 7H), 1.81(m, 4H), 1.36(t, 3H). | 455 |
| 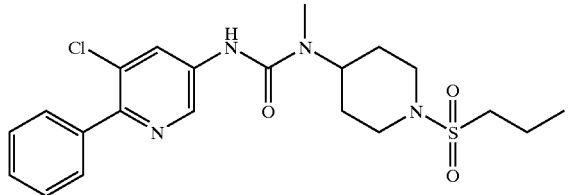<br>5C | (CDCl₃) δ 8.44(d, J=2.0Hz, 1H), 8.24 (d, J=2.4Hz, 1H), 7.50(m, 1H), 7.41 (m, 2H), 7.10(m, 1H), 6.67(s, 1H), 4.44 (m, 1H), 3.93(m, 2H), 2.90(m, 7H), 1.81(m, 6H), 1.06(t, 3H). | 469 |
| 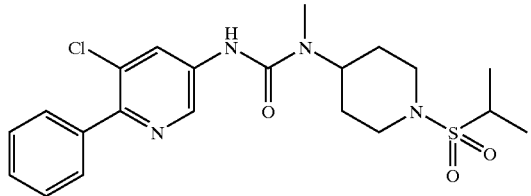<br>5D | (CDCl₃) δ 8.43(d, J=2.4Hz, 1H), 8.26 (d, J=2.4Hz, 1H), 7.51(m, 1H), 7.43 (m, 2H), 7.10(m, 1H), 6.60(s, 1H), 4.46 (m, 1H), 3.96(m, 2H), 3.19(m, 1H), 3.01(m, 2H), 2.93(s, 3H), 1.79(m, 4H), 1.34(d, 6H). | 469 |
| 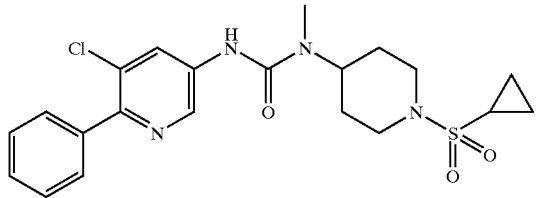<br>5E | (CDCl₃) δ 8.43(d, J=2.4Hz, 1H), 8.26 (d, J=2.4Hz, 1H), 7.51(m, 1H), 7.43 (m, 2H), 7.10(m, 1H), 6.64(s, 1H), 4.43 (m, 1H), 3.92(m, 2H), 2.93(m, 5H), 2.27(m, 1H), 1.81(m, 4H), 1.16(m, 2H), 1.00(m, 2H). | 467 |
| 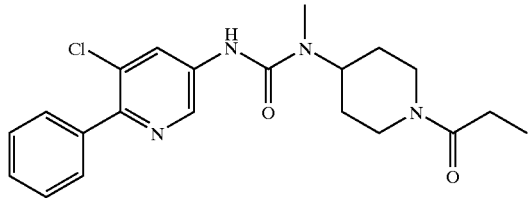<br>5F | (CDCl₃) δ 8.44(d, J=2.0Hz, 1H), 8.26 (d, J=2.4Hz, 1H), 7.48(m, 1H), 7.40 (m, 2H), 7.10(m, 1H), 6.92(s, 1H), 4.76 (m, 1H), 4.50(m, 1H), 3.94(m, 1H), 3.12(t, 1H), 2.90(s, 3H), 2.60(m, 1H), 2.36(q, 2H), 1.80–1.55(m, 4H), 1.15(t, 3H). | 419 |

-continued
| STRUCTURE | ¹H NMR | MS (M + H)⁺ |
|---|---|---|
| 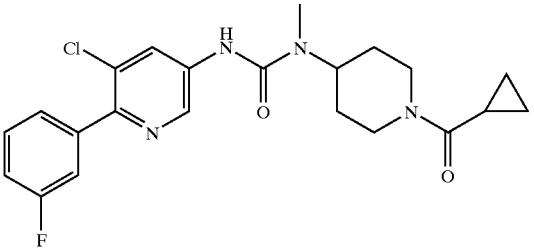<br>5G | (CDCl₃) δ 8.43(d, J=2.4Hz, 1H), 8.26 (d, J=2.4Hz, 1H), 7.50(m, 1H), 7.40 (m, 2H), 7.10(m, 1H), 6.89(s, 1H), 4.76 (m, 1H), 4.51(m, 1H), 3.32(m, 1H), 3.12(m, 1H), 2.90(s, 3H), 2.64(m, 1H), 1.89–1.55(m, 5H), 0.98(m, 2H), 0.77 (m, 2H). | 431 |
| 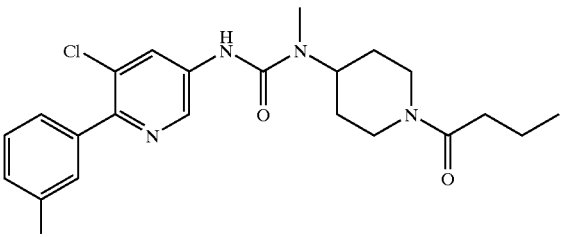<br>5H | (CDCl₃) δ 8.43(d, J=2.4Hz, 1H), 8.27 (d, J=2.4Hz, 1H), 7.50(m, 1H), 7.40 (m, 2H), 7.10(m, 1H), 6.78(s, 1H), 4.79 (m, 1H), 4.50(m, 1H), 3.96(m, 1H), 3.13(t, 1H), 2.91(s, 3H), 2.60(m, 1H), 2.33(q, 2H), 1.81–1.55(m, 6H), 0.97(t, 3H). | 433 |
| 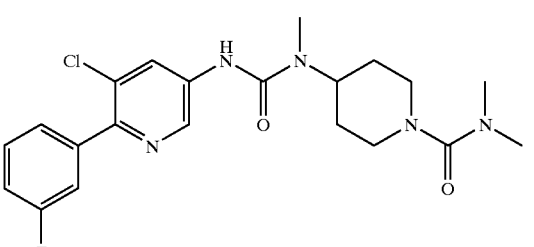<br>5I | (CDCl₃) δ 8.43(d, J=2.4Hz, 1H), 8.25 (d, J=2.4Hz, 1H), 7.48(m, 1H), 7.38 (m, 2H), 7.08(m, 1H), 7.02(s, 1H), 4.39 (m, 1H), 3.75(m, 2H), 2.90–2.80(m, 11H), 1.67(m, 4H) | 434 |
| 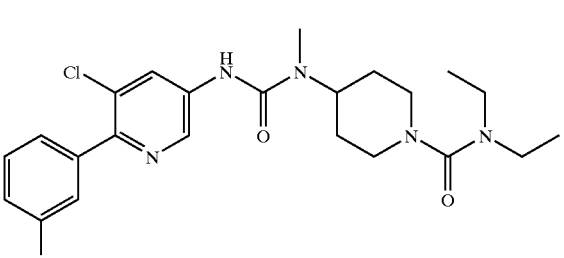<br>5J | (CDCl₃) δ 8.43(d, J=2.4Hz, 1H), 8.30 (d, J=2.4Hz, 1H), 7.50(m, 1H), 7.43 (m, 2H), 7.08(m, 1H), 6.69(s, 1H), 4.41 (m, 1H), 3.75(m, 2H), 3.20(q, 4H), 2.90 (s, 3H), 2.85(m, 2H), 1.69(m, 4H), 1.27 (t, 6H). | 462 |
| 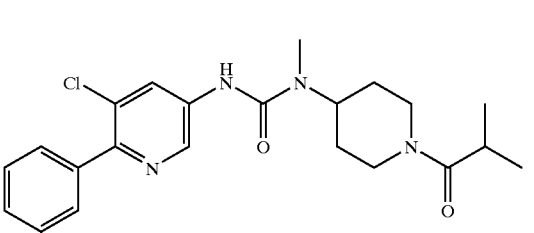<br>5K | (CDCl₃) δ 8.43(d, J=2.0Hz, 1H), 8.27 (d, J=2.4Hz, 1H), 7.49(m, 1H), 7.40 (m, 2H), 7.09(m, 1H), 6.87(s, 1H), 4.80 (m, 1H), 4.51(m, 1H), 4.05(m, 1H), 3.14(m, 1H), 2.90(s, 3H), 2.80(m, 1H), 2.59(m, 1H), 1.82–1.56(m, 4H), 1.13 (m, 6H). | 433 |

| STRUCTURE | ¹H NMR | MS (M + H)⁺ |
|---|---|---|
| 5L | (CDCl₃) δ 8.40(d, J=2.0Hz, 1H), 8.32 (d, J=2.4Hz, 1H), 7.29(m, 2H), 6.85 (m, 1H), 6.49(m, 1H), 4.42(m, 1H), 4.23(m, 2H), 2.93(s, 3H), 2.81(m, 2H), 1.70–1.57(m, 4H), 1.45(m, 9H). | 481 |
| 5M | (CDCl₃) δ 8.44(d, J=2.0Hz, 1H), 8.24 (d, J=2.0Hz, 1H), 7.27(m, 2H), 6.84 (m, 1H), 6.73(s, 1H), 4.41(m, 1H), 3.92 (m, 2H), 2.93(s, 3H), 2.78(m, 5H), 1.81 (m, 4H). | 459 |
| 5N | (CDCl₃) δ 8.43(m, 1H), 8.28(m, 1H), 7.28(m, 2H), 6.84(m, 1H), 6.54(s, 1H), 4.45(m, 1H), 3.94(m, 2H), 2.95(m, 7H), 1.81(m, 4H), 1.36(t, 3H). | 473 |
| 5O | (CDCl₃) δ 8.42(d, J=2.0Hz, 1H), 8.28 (d, J=2.0Hz, 1H), 7.27(m, 2H), 6.84 (m, 1H), 6.52(s, 1H), 4.45(m, 1H), 3.94 (m, 2H), 2.95(s, 3H), 2.88(m, 4H), 1.85 (m, 6H), 1.07(t, 3H). | 487 |
| 5P | (CDCl₃) δ 8.43(d, J=2.4Hz, 1H), 8.27 (d, J=2.4Hz, 1H), 7.27(m, 2H), 6.84 (m, 1H), 6.58(s, 1H), 4.45(m, 1H), 3.94 (m, 2H), 3.19(m, 1H), 3.00(m, 2H), 2.95(s, 3H), 1.75(m, 4H), 1.35(d, 6H). | 487 |

-continued

| STRUCTURE | ¹H NMR | MS (M + H)⁺ |
|---|---|---|
| 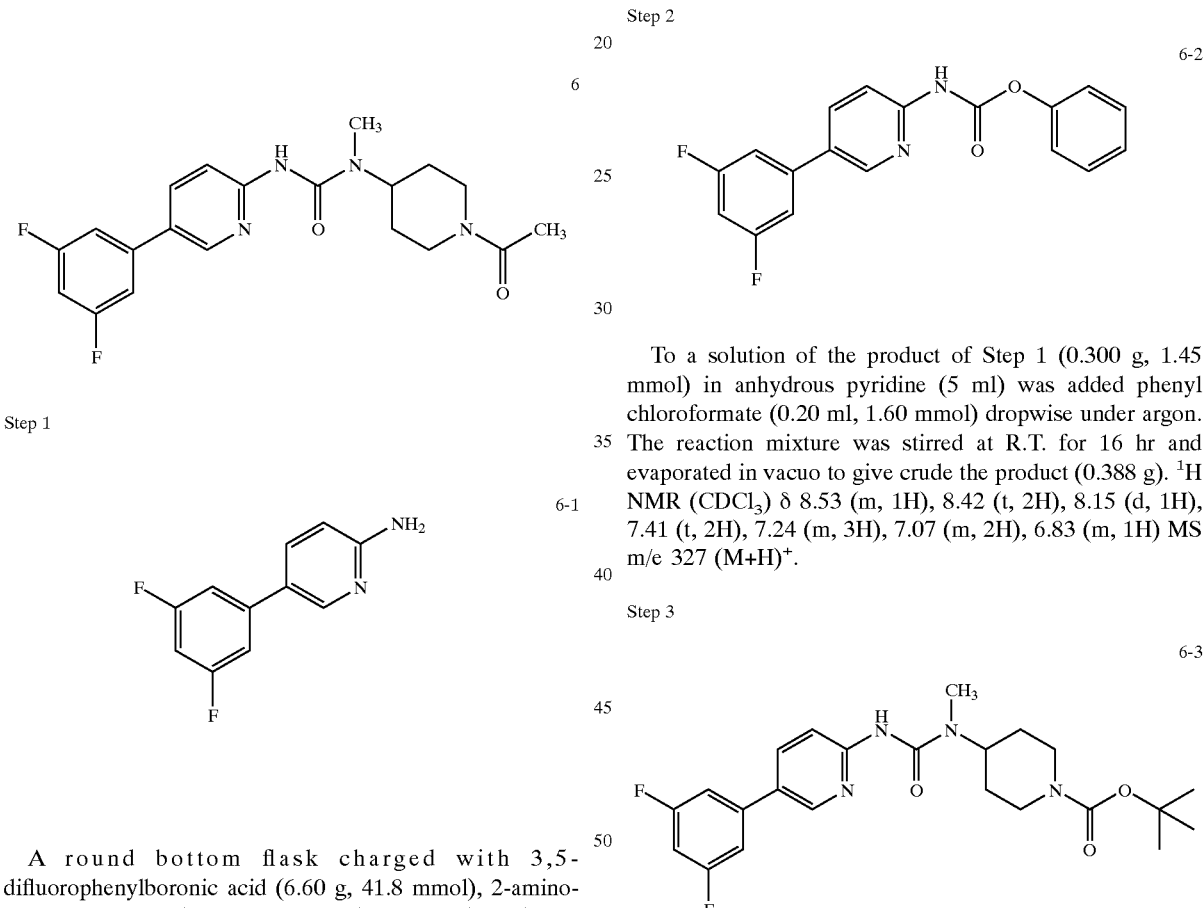 5Q | (CDCl₃) δ 8.44(d, J=2.0Hz, 1H), 8.27 (d, J=2.4Hz, 1H), 7.27(m, 2H), 6.84 (m, 1H), 6.60(s, 1H), 4.41(m, 1H), 3.92 (m, 2H), 2.95(m, 5H), 2.28(m, 1H), 1.81(m, 4H), 1.17(m, 2H), 1.00(m, 2H). | 485 |

EXAMPLE 6

Step 1

A round bottom flask charged with 3,5-difluorophenylboronic acid (6.60 g, 41.8 mmol), 2-amino-5-bromo pyridine (6.00 g, 34.7 mmol), benzene (80 ml), and 2M aq. Na₂CO₃ (40 ml) was purged with N₂ for 5 min. Pd(PPh₃)₄ (1.20 g, 1.04 mmol) was added and the reaction mixture was heated to 100° C. for 16 hr. After cooling, the reaction mixture was poured into cold water (100 ml). The whole was extracted with CH₂Cl₂ (3×150 ml), dried (Na₂SO₄), and filtered. The concentrated residue was subjected to flash column chromatography (1:10 acetone/hexane) to give the product (4.90 g, 69%). ¹H NMR (CDCl₃) δ 8.28 (d, J=2.4Hz, 1H), 7.63 (dd, J=8.8, 2.4Hz, 1H), 7.01 (m, 2H), 6.76 (m, 1H), 6.58 (d, J=8.4Hz, 1H), 4.65 (s, b, 2H). MS m/e 207 (M+H)⁺.

Step 2

To a solution of the product of Step 1 (0.300 g, 1.45 mmol) in anhydrous pyridine (5 ml) was added phenyl chloroformate (0.20 ml, 1.60 mmol) dropwise under argon. The reaction mixture was stirred at R.T. for 16 hr and evaporated in vacuo to give crude the product (0.388 g). ¹H NMR (CDCl₃) δ 8.53 (m, 1H), 8.42 (t, 2H), 8.15 (d, 1H), 7.41 (t, 2H), 7.24 (m, 3H), 7.07 (m, 2H), 6.83 (m, 1H) MS m/e 327 (M+H)⁺.

Step 3

To a solution of the product of Step 2 (0.200 g, 0.613 mmol) in chloroform (10 ml) was added Preparation 1 (HCl salt) (0.230 g, 0.919 mmol) and Et₃N (0.43 ml, 3.06 mmol). The reaction mixture was refluxed for 16 hr, then allowed to cool and concentrated. Subjection of the residue to PTLC (1:2 EtOAc/hexane) gave the product (0.062 g, 23%) as a solid. ¹HNMR (CDCl₃) δ 8.40 (s, 1H), 8.16 (d, 1H), 7.85 (m, 1H), 7.27 (s, 1H), 7.07 (m, 2H), 6.69 (m, 1H), 4.42 (m, 1H), 4.25 (s, b, 2H), 2.92 (s, 3H), 2.82 (m, 2H), 1.67 (m, 4H), 1.47 (s, 9H). MS m/e 447 (M+H)⁺.

Step 4

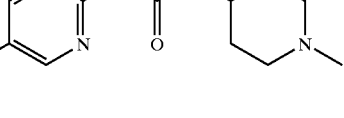

6-4

A mixture of the product of Step 3 (0.205 g, 0.460 mmol) and 4N HCl/1,4-dioxane (5 ml) was stirred at R.T. for 1 hr, then evaporated to give the product (0.137 g, 100%) as a solid. MS m/e 347 (M+H)⁺.

Step 5

To a solution of the product of Step 4 (0.042 g, 0.11 mmol) and iPr₂NEt (0.057 ml, 0.33 mmol) in CH₂Cl₂ (2.0 ml) was slowly added acetyl chloride (7.0 µl, 0.1 mmol). The reaction mixture was stirred at R.T. for 16 hr, then concentrated. Subjection of the residue to PTLC (1:10 MeOH/CH₂Cl₂) gave the product (0.030 g, 78%) as a solid. ¹HNMR (CDCl₃) δ 8.39 (m, 1H), 8.15 (m, 1H), 7.83 (dd, J=8.8, 2.4Hz, 1H), 7.28 (s, 1H), 7.06 (m, 2H), 6.79 (m, 1H), 4.78 (m, 1H), 4.51 (m, 1H), 3.92 (m, 1 H), 3.18 (m, 1H), 2.91 (s, 3H), 2.62 (m, 1H), 2.12 (s, 3H), 1.78 (m, 2H), 1.60 (m, 2H). MS m/e 389 (M+H)⁺.

| STRUCTURE | ¹H NMR | MS (M + H)⁺ |
|---|---|---|
| 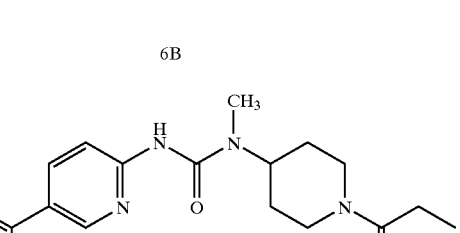<br>6A | ¹H NMR (DMSO-d6) δ 8.44(1H, s), 8.11(1H, m), 7.88(1H, m), 7.55(2H, m), 7.45(2H, m), 7.35 (1H, m), 4.39(1H, m), 3.20(2H, m), 2.97(3H, s), 2.49(3H, s), 2.40(2H, m), 2.13(2H, m), 1.76 (2H, m). | 325 |
| 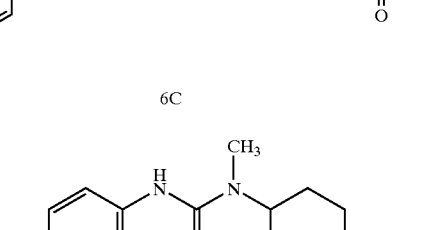<br>6B | (CDCl₃) δ 8.40(d, J=2.0Hz, 1H), 8.14(d, J=8.8Hz, 1H), 7.84(dd, J=8.8, 2.4Hz, 1H), 7.29 (s, 1H), 7.07(m, 2H), 6.80(m, 1H), 4.44(m, 1H), 3.93(m, 2H), 2.96(s, 3H), 2.81(s, 3H), 2.80 (m, 2H), 1.84(m, 4H) | 425 |
| <br>6C | (CDCl₃) δ 8.39(d, J=2.4Hz, 1H), 8.15(d, J=8.8Hz, 1H), 7.83(dd, J=8.8, 2.4Hz, 1H), 7.30 (s, 1H), 7.06(m, 2H), 6.79(m, 1H), 4.79(m, 1H), 4.51(m, 1H), 3.94(d, b, 1H), 3.13(m, 1H), 2.91(s, 3H), 2.61(m, 1H), 2.37 (q, J=7.6Hz, 2H), 1.78(m, 2H), 1.60(m, 2H), 1.16(t, J=7.6Hz, 3H) | 403 |
| 6D | (CDCl₃) δ 8.40(d, J=2.0Hz, 1H), 8.15(d, J=8.8Hz, 1H), 7.83(dd, J=8.8, 2.4Hz, 1H), 7.27 (s, 1H), 7.06(m, 2H), 6.79(m, 1H), 4.82(m, 1H), 4.51(m, 1H), 3.97(d, b, 1H), 3.14(m, 1H), 2.91(s, 3H), 2.61(m, 1H), 2.33 (t, J=6.8Hz, 2H), 1.90–1.50(m, 6H), 0.98(t, J=7.6Hz, 3H) | 417 |

EXAMPLE 7

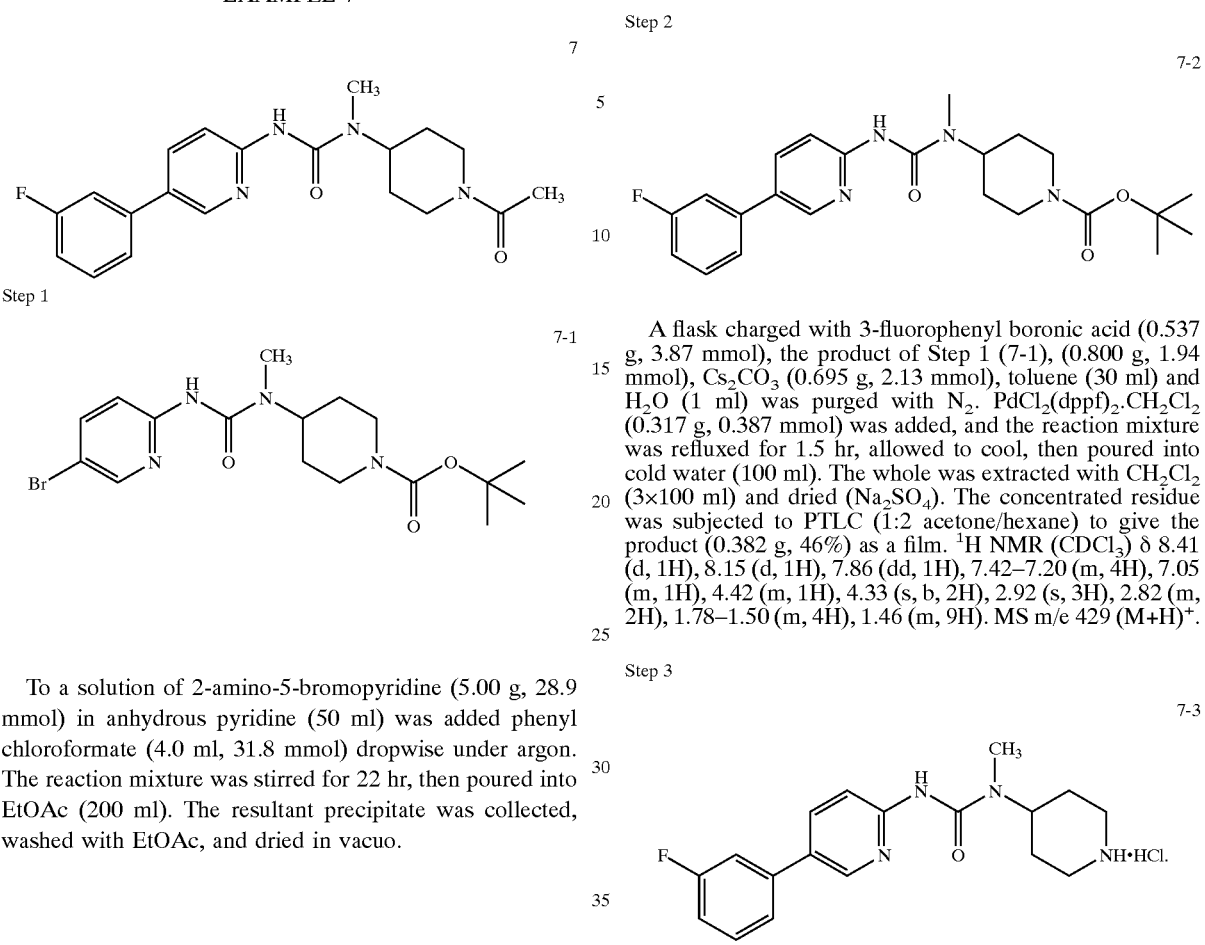

Step 1

To a solution of 2-amino-5-bromopyridine (5.00 g, 28.9 mmol) in anhydrous pyridine (50 ml) was added phenyl chloroformate (4.0 ml, 31.8 mmol) dropwise under argon. The reaction mixture was stirred for 22 hr, then poured into EtOAc (200 ml). The resultant precipitate was collected, washed with EtOAc, and dried in vacuo.

To a solution of the crude product was added Preparation 1 (6.19 g, 28.9 mmol), Et$_3$N (12.0 ml, 86.7 mmol) and CHCl$_3$ (100 ml). The reaction mixture was refluxed for 24 hr, allowed to cool and poured into cold H$_2$O (~200 ml). The whole was extracted with CH$_2$Cl$_2$ (3×200 ml), dried (Na$_2$SO$_4$), filtered and evaporated. The residue was subjected to flash chromatography (1:4 then 1:2 EtOAc/hexane) to give the product as a solid (7.20 g, 60%). $^1$H NMR (CDCl$_3$) δ 8.17 (m, 1H), 7.94 (m, 1H), 7.68 (m, 1H), 7.22 (s, 1H), 4.32 (m, 1H), 4.18 (s, b, 2H), 2.83 (s, 3H), 2.74 (m, 2H), 1.58 (m, 4H), 1.41 (s, 9H). MS m/e 413 (M+H)$^+$.

Step 2

A flask charged with 3-fluorophenyl boronic acid (0.537 g, 3.87 mmol), the product of Step 1 (7-1), (0.800 g, 1.94 mmol), Cs$_2$CO$_3$ (0.695 g, 2.13 mmol), toluene (30 ml) and H$_2$O (1 ml) was purged with N$_2$. PdCl$_2$(dppf)$_2$·CH$_2$Cl$_2$ (0.317 g, 0.387 mmol) was added, and the reaction mixture was refluxed for 1.5 hr, allowed to cool, then poured into cold water (100 ml). The whole was extracted with CH$_2$Cl$_2$ (3×100 ml) and dried (Na$_2$SO$_4$). The concentrated residue was subjected to PTLC (1:2 acetone/hexane) to give the product (0.382 g, 46%) as a film. $^1$H NMR (CDCl$_3$) δ 8.41 (d, 1H), 8.15 (d, 1H), 7.86 (dd, 1H), 7.42–7.20 (m, 4H), 7.05 (m, 1H), 4.42 (m, 1H), 4.33 (s, b, 2H), 2.92 (s, 3H), 2.82 (m, 2H), 1.78–1.50 (m, 4H), 1.46 (m, 9H). MS m/e 429 (M+H)$^+$.

Step 3

Reaction of the product of Step 2 by the method of Example 6, Step 4 gave the product. MS m/e 329 (M+H)$^+$.

Step 4

Using essentially the same procedure as Example 4, reaction of the product of Step 3 with CH$_3$COCl and Et$_3$N gave the product. $^1$H NMR (CDCl$_3$) δ 8.42 (d, 1H), 8.13 (m, 1H), 7.87 (m, 1H), 7.45–7.20 (m, 4H), 7.05 (m, 1H), 4.78 (m, 1H), 4.51 (m, 1H), 3.92 (m, 1H), 3.18 (m, 1H), 2.91 (s, 3H), 2.63 (m, 1H), 2.12 (s, 3H), 1.78 (m, 2H), 1.60 (m, 2H). MS m/e 371 (M+H)$^+$.

Using appropriate procedures, the following Examples were prepared.

| STRUCTURE | $^1$H NMR | MS (M + H)$^+$ |
|---|---|---|
| <br>7A | (CDCl$_3$) δ 8.37(s, 1H), 8.15(d, 1H), 7.83(m, 1H), 7.28(s, 1H), 7.13(m, 2H), 7.01(m, 1H), 4.41 (m, 1H), 4.22(s, b, 2H), 2.91(s, 3H), 2.80(m, 2H), 1.75–1.50(m, 4H), 1.46(s, 9H) | 447 |

| STRUCTURE | ¹H NMR | MS (M + H)⁺ |
|---|---|---|
| 7B | (CDCl₃) δ 8.39(s, 1H), 8.15(d, 1H), 7.85(d, 1H), 7.32(s, b, 1H), 7.14(m, 2H), 7.03(m, 1H), 4.43 (m, 1H), 3.94(d, b, 2H), 2.95(s, 3H), 2.81(s, 3H), 2.78(m, 2H), 1.84(m, 4H) | 425 |
| 7C | (CDCl₃) δ 8.39(s, 1H), 8.14(d, 1H), 7.84(d, 1H), 7.26(s, 1H), 7.14(m, 2H), 7.00(m, 1H), 4.78 (d, b, 1H), 4.51(m, 1H), 3.91(d, b, 1H), 3.18(m, 1H), 2.91(s, 3H), 2.62(m, 1H), 2.12(s, 3H), 1.78(m, 2H), 1.61(m, 2H) | 389 |
| 7D | (CDCl₃) δ 8.39(s, 1H), 8.15(d, 1H), 7.85(m, 1H), 7.27(s, 1H), 7.14(m, 2H), 7.02(m, 1H), 4.81 (d, b, 1H), 4.51(m, 1H), 3.95(d, b, 1H), 3.14(m, 1H), 2.91(s, 3H), 2.62(m, 1H), 2.37(q, 2H), 1.77(m, 2H), 1.61(m, 2H), 1.16 (t, 3H) | 403 |
| 7E | (CDCl₃) δ 8.39(s, 1H), 8.14(dd, 1H), 7.85(m, 1H), 7.26(s, 1H), 7.12(m, 2H), 7.02(m, 1H), 4.81 (m, 1H), 4.51(m, 1H), 3.97(d, b, 1H), 3.14(m, 1H), 2.91(s, 3H), 2.61(m, 1H), 2.33(t, 2H), 1.90–1.50(m, 6H), 0.98(t, 3H) | 417 |
| 7F | (CDCl₃) δ 8.42(d, 1H), 8.13(d, 1H), 7.87(dd, 1H), 7.45–7.20(m, 4H), 7.06(m, 1H), 4.45(m, 1H), 3.93(m, 2H), 3.05(s, 3H), 2.81 (s, 3H), 2.80(m, 2H), 1.83(m, 4H) | 407 |

-continued

| STRUCTURE | ¹H NMR | MS (M + H)⁺ |
|---|---|---|
| 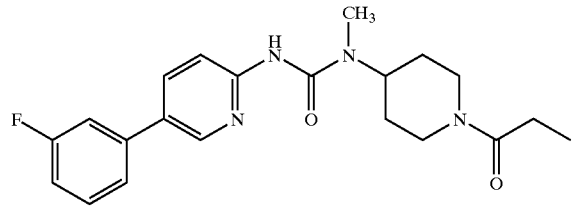<br>7G | (CDCl₃) δ 8.41(d, 1H), 8.13(d, 1H), 7.86(dd, 1H), 7.45–7.20(m, 4H), 7.05(m, 1H), 4.81(m, 1H), 4.52(m, 1H), 3.95(m, 1H), 3.13 (m, 1H), 2.91(s, 3H), 2.62(m, 1H), 2.36(q, 2H), 1.75(m, 2H), 1.58(m, 2H), 1.16(t, 3H) | 385 |

EXAMPLE 8

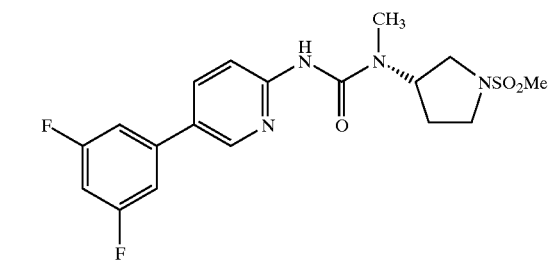

8

Step 1

8-1

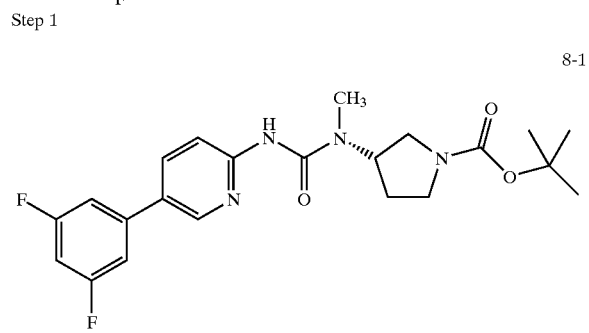

Reaction of 6-2 with Preparation 10 using the procedure of Example 6, Step 3, gave the product. ¹HNMR (CDCl₃) δ 8.38 (d, J=2.0Hz, 1H), 8.13 (d, J=8.8 Hz, 1H), 7.82 (dd, J=8.8, 2.4Hz, 1H), 7.36 (s, 1H), 7.06 (m, 2H), 6.78 (m, 1H), 5.04 (m, 1H), 3.70–3.10 (m, 4H), 2.98 (s, 3H), 2.10 (m, 1H), 1.97 (m, 1H), 1.45 (s, 9H). MS m/e 433 (M+H)⁺.

Step 2

8-2

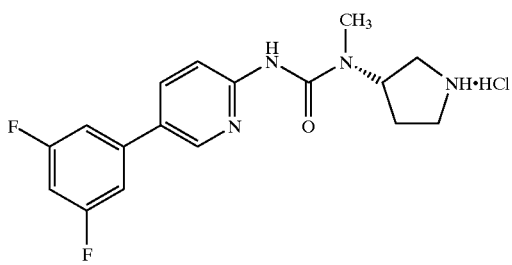

The product of Step 1 was treated with HCl by the procedure of Example 6, Step 4, to give the product. ¹H NMR (CD₃OD) δ 8.63 (m, 2H), 7.85 (d, 1H), 7.42 (m, 2H), 7.13 (m, 1H), 4.82 (m, 1H), 4.80–4.40 (m, 4H), 3.22 (s, 3H), 2.43 (m, 1H), 2.32 (m, 1H). MS m/e 333 (M+H)⁺.

Step 3

Using the procedure of Example 3, Step 3, the product was synthesized in 56% yield as a solid. ¹H NMR (CDCl₃) δ 8.38 (d, 1H), 8.22 (d, 1H), 7.90 (m, 1H), 7.26 (s, 1H), 7.06 (m, 2H), 6.83 (m, 1H), 5.15 (m, 1H), 3.67 (m, 1H), 3.52 (m, 1H), 3.35 (m, 1H), 3.25 (m, 1H), 3.07 (s, 3H), 2.90 (s, 3H), 2.25 (m, 1H), 2.08 (m, 1 H). MS m/e 411 (M+H)⁺.

EXAMPLE 9

9

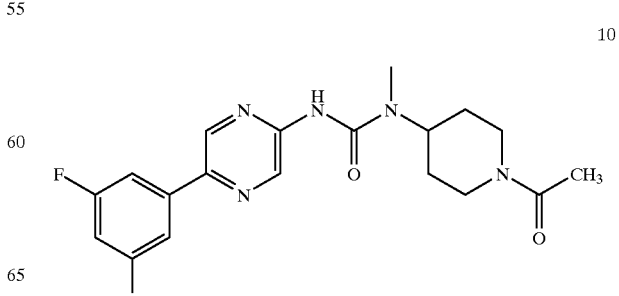

A mixture of Example 6B (0.030 g, 0.071 mmol), CH₂Cl₂ (5 ml) and mCPBA (57–80%, 0.032 g) was stirred at R.T. for 1.5 hr, then poured into H₂O (10 ml). The whole was extracted with CH₂Cl₂ (3×20 ml), dried (Na₂SO₄), filtered and concentrated. Subjection of the residue to PTLC (1:20 CH₃OH/CH₂Cl₂) gave the product (0.0194 mg, 62%) as a solid. ¹H NMR (CDCl₃) δ 9.81 (s, 1H), 8.46 (d, J=2.0Hz, 1H), 8.37 (d, J=9.2Hz, 1H), 7.49 (dd, J=8.8, 2.0Hz, 1H), 7.04 (m, 2H), 6.86 (m, 1H), 4.39 (s, b, 1H), 3.95 (d, b, 2H), 3.02 (s, 3H), 2.83 (m, 5H), 1.88 (m, 4H). MS m/e 441 (M+H)⁺.

EXAMPLE 10

10

Step 1

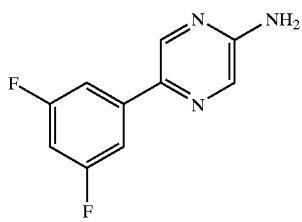
10-1

A flask charged with 2-amino-5-bromopyrazine (4.00 g, 23.0 mmol), 3,5-difluorophenylboronic acid (5.44 g, 34.5 mmol), toluene (150 ml), water (5 ml) and cesium carbonate (8.24 g, 25.3 mmol) was purged with $N_2$. $PdCl_2(dppf)\cdot CH_2Cl_2$ (0.93 g, 1.15 mmol) was added and the mixture was refluxed 2 hr, allowed to cool, then poured into cold water (100 ml). The whole was extracted with $CH_2Cl_2$ (3×200 ml), dried ($Na_2SO_4$), and filtered. The concentrated residue was subjected to flash column chromatography (1:4 then 1:2 acetone/hexane) to give the product (4.42 g, 93%). $^1$HNMR (CDCl$_3$) δ 8.42 (d, J=1.6Hz, 1H), 8.05 (d, J=1.2Hz, 1H), 7.42 (m, 2H), 6.79 (m, 1H), 4.75 (s, 2H). MS m/e 208 (M+H)$^+$.

Step 2

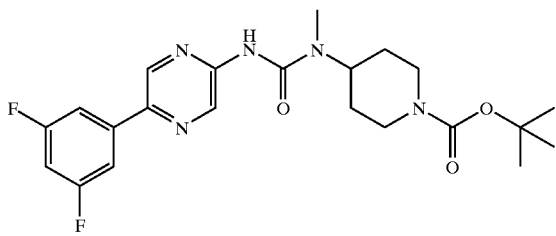
10-2

To a solution of the product of Step 1 (2.00 g, 9.65 mmol) in anhydrous pyridine (40 ml) was added phenyl chloroformate dropwise under argon. The reaction mixture was stirred for 16 hr, then concentrated. To the residue was added chloroform (50 ml), followed by Preparation 1 (3.10 g, 14.5 mmol) and Et$_3$N (4.0 ml, 28.9 mmol). The reaction mixture was refluxed for 4 hr, then allowed to cool and poured into water. The whole was extracted with $CH_2Cl_2$ (3×200 ml) and dried ($Na_2SO_4$), filtered and concentrated. Crystallization of the residue (acetone/hexane) gave the product (2.52 g, 58%). The mother liquor was concentrated and subjected to flash chromatography (1:5 acetone/hexane) to afford additional product (0.943 g, total 80%). $^1$H NMR (CDCl$_3$) δ 9.45 (d, J=1.6Hz, 1H), 8.55 (d, J=1.2Hz, 1H), 7.51 (m, 2H), 7.17 (s, 1H), 6.85 (m, 1H), 4.43 (m, 1H), 4.24 (m, 2H), 2.95 (s, 3H), 2.82 (m, 2H), 1.63 (m, 4H), 1.47 (s, 9H). MS m/e 448 (M+H)$^+$.

Step 3

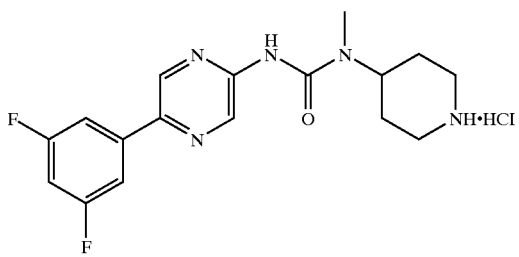
10-3

The product of Step 2 (2.50 g, 5.59 mmol) was treated with 4M HCl/1,4-dioxane (30 ml) by the procedure of Example 6, Step 4 to afford the product. $^1$H NMR (CD$_3$OD) δ 9.19 (s, b, 1H), 8.79 (s, b, 1H), 7.66 (m, 2H), 7.03 (m, 1H), 4.42–3.49 (m, 5H), 3.16 (m, 2H), 3.04 (s, 3H), 2.20–1.95 (m, 4H). MS m/e 348 (M+H)$^+$.

Step 4

To a mixture of the product of Step 3 (2.15 g, 5.59 mmol), and Et$_3$N (3.9 ml, 28.0 mmol) in CH$_2$Cl$_2$ (50 ml) was added acetic anhydride (0.58 ml, 6.15 mmol). The reaction mixture was stirred for 16 hr, then poured into water (100 ml). The whole was extracted with CH$_2$Cl$_2$ (3×200 ml), dried (Na$_2$SO$_4$), filtered, and evaporated. The residue was subjected to flash chromatography (gradient 1:100–5:95 MeOH/CH$_2$Cl$_2$) to give the product (1.71 g, 78%). $^1$H NMR (CDCl$_3$) δ 9.44 (d, J=1.2Hz, 1H), 8.55 (d, J=1.6Hz, 1H), 7.51 (m, 2H), 7.23 (s, 1H), 6.84 (m, 1H), 4.79 (m, 1H), 4.53 (m, 1H), 3.91 (m, 1H), 3.20 (m, 1H), 2.94 (s, 3H), 2.63 (m, 1H), 2.12 (s, 3H), 1.86–1.55 (m, 4H). MS m/e 390 (M+H)$^+$.

Use of the appropriate procedures afforded the following compounds:

| STRUCTURE | $^1$H NMR | MS (M + H)$^+$ |
|---|---|---|
| 10A | (CDCl$_3$) δ 9.44(bs, 1H), 8.55(bs, 1H), 7.52(m, 2H), 7.22(s, 1H), 6.85(m, 1H), 4.79(m, 1H), 4.53 (m, 1H), 3.91(m, 1H), 3.20(m, 1H), 2.94(s, 3H), 2.63(m, 1H), 2.37(m, 2H), 1.86–1.55(m, 4H), 1.16(m, 3H). | 404 |

| STRUCTURE | ¹H NMR | MS (M + H)⁺ |
|---|---|---|
| 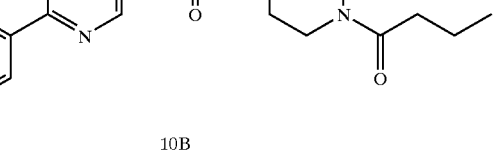<br>10B | (CDCl$_3$) δ 9.45(bs, 1H), 8.56 (bs, 1H), 7.52(m, 2H), 7.19(s, 1H), 6.85(m, 1H), 4.81(m, 1H), 4.53(m, 1H), 3.98(m, 1H), 3.15 (m, 1H), 2.94(s, 3H), 2.62(m, 1H), 2.33(m, 2H), 1.83–1.56(m, 6H), 0.98(m, 3H). | 418 |
| 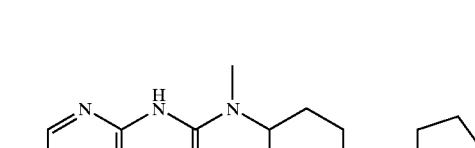<br>10C | (CDCl$_3$) δ 9.45(bs, 1H), 8.56(bs, 1H), 7.52(m, 2H), 7.26(s, 1H), 6.85(t, 1H), 4.82(b, 1H), 4.53 (m, 1H), 4.10(b, 1H), 3.15(t, 1H), 2.93(m, 4H), 2.62(t, 1H), 1.90–1.50(m, 12H). | 444 |
| 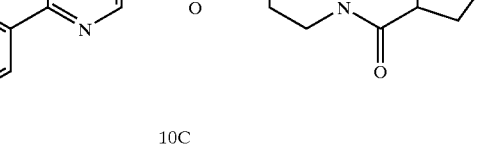<br>10D | (CDCl$_3$) δ 9.45(d, J=1.2Hz, 1H), 8.56(d, J=1.2Hz, 1H), 7.51(m, 2H), 7.21(s, 1H), 6.84 (m, 1H), 4.83(m, 1H), 4.54(m, 1H), 4.05(m, 1H), 3.16(m, 1H), 2.94(s, 3H), 2.84(m, 1H), 2.62 (m, 1H), 1.82(m, 2H), 1.58(m, 2H), 1.14(m, 6H) | 418 |
| 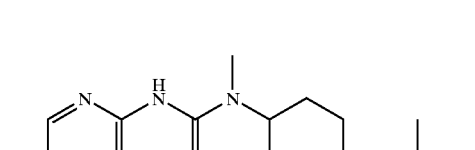<br>10E | (CDCl$_3$) δ 9.45(d, J=1.2Hz, 1H), 8.56(d, J=1.2Hz, 1H), 7.51(m, 2H), 7.22(s, 1H), 6.84 (m, 1H), 4.77(m, 1H), 4.56(m, 1H), 4.38(m, 1H), 3.22(m, 1H), 2.94(s, 3H), 2.67(m, 1H), 1.90–1.55(m, 5H), 1.00(m, 2H), 0.78 (m, 2H) | 416 |
| 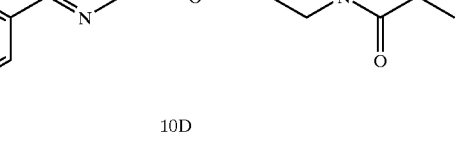<br>10F | (CDCl$_3$) δ 9.43(d, J=1.6Hz, 1H), 8.55(d, J=1.6Hz, 1H), 7.51(m, 2H), 7.28(s, 1H), 6.84 (m, 1H), 4.76(m, 1H), 4.56(m, 1H), 4.11(q, 2H), 4.02(m, 1H), 3.43(s, 3H), 3.17(m, 1H), 2.93 (s, 3H), 2.68(m, 1H), 1.95–1.57 (m, 4H) | 420 |

-continued
| STRUCTURE | ¹H NMR | MS (M + H)⁺ |
|---|---|---|
| 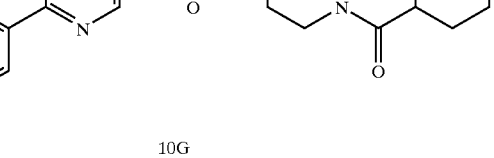<br>10G | (CDCl₃) δ 9.45(d, J=1.6Hz, 1H), 8.55(d, J=1.2Hz, 1H), 7.51(m, 2H), 7.24(s, 1H), 6.84 (m, 1H), 4.82(m, 1H), 4.53(m, 1H), 4.03(m, 1H), 3.15(m, 1H), 2.93(s, 3H), 2.61(m, 1H), 2.49 (m, 1H), 1.95–1.20(m, 14H) | 458 |
| 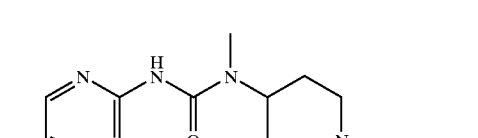<br>10H | (CDCl₃) δ 9.44(d, J=1.6Hz, 1H), 8.55(d, J=1.6Hz, 1H), 7.51(m, 2H), 7.23(s, 1H), 6.84 (m, 1H), 4.82(m, 1H), 4.53(m, 1H), 4.00(m, 1H), 3.15(m, 1H), 2.93(s, 3H), 2.61(m, 1H), 2.23 (m, 2H), 2.14(m, 1H), 1.90–1.50 (m, 4H), 0.98(m, 6H) | 432 |
| 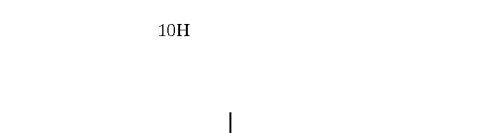<br>10I | (CDCl₃) δ 9.44(s, 1H), 8.55(s, 1H), 7.51(m, 2H), 7.25(s, 1H), 6.84(m, 1H), 4.85(m, 1H), 4.53 (m, 1H), 4.05(m, 1H), 3.17(m, 1H), 2.93(s, 3H), 2.61(m, 1H), 2.28(q, 2H), 1.90–1.50(m, 4H), 1.04(m, 9H) | 446 |
| 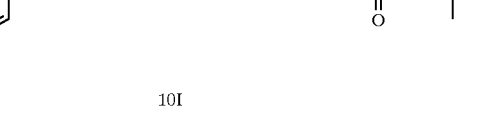<br>10J | (CDCl₃) δ 9.42(d, J=1.6Hz, 1H), 8.53(d, J=1.6Hz, 1H), 7.49(m, 2H), 7.32(s, 1H), 6.83 (m, 1H), 4.82(m, 1H), 4.57(m, 1H), 3.97(m, 1H), 3.18(m, 1H), 2.93(s, 3H), 2.62(m, 1H), 2.30 (m, 2H), 1.85–1.50(m, 4H), 1.03 (m, 1H), 0.57(m, 2H), 0.17(m, 2H) | 430 |
| 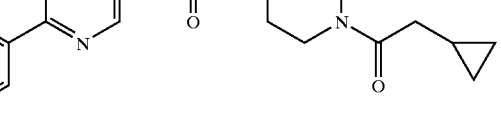<br>10K | (CDCl₃) δ 9.45(s, 1H), 8.55(s, 1H), 7.51(m, 2H), 7.24(s, 1H), 6.83(m, 1H), 4.55(m, 3H), 2.93 (m, 3H), 2.84(m, 2H), 1.90–1.50 (m, 4H), 1.29(s, 9H) | 432 |

-continued

| STRUCTURE | ¹H NMR | MS (M + H)⁺ |
|---|---|---|
| 10L | (CDCl₃) δ 9.44(d, J=1.6Hz, 1H), 8.55(d, J=1.6Hz, 1H), 7.49(m, 2H), 7.45(m, 1H), 7.31 (m, 1H), 7.28(s, 1H), 7.05(m, 1H), 6.84(m, 1H), 4.62(m, 3H), 3.08(m, 2H), 2.97(s, 3H), 1.90–1.60(m, 4H) | 458 |
| 10M | (CDCl₃) δ 9.44(d, J=1.6Hz, 1H), 8.55(d, J=1.6Hz, 1H), 7.52(m, 2H), 7.42(m, 5H), 7.26 (s, 1H), 6.85(m, 1H), 4.90(bs, 1H), 4.78(m, 1H), 3.90(bs, 1H), 3.15(m, b, 1H), 2.97(s, 3H), 2.87(bs, 1H), 2.90–1.50(m, b, 4H) | 452 |
| 10N | (CDCl₃) δ 9.45(d, J=1.6Hz, 1H), 8.55(d, J=1.2Hz, 1H), 7.51(m, 2H), 7.22(s, 1H), 6.85 (m, 1H), 4.82(b, 1H), 4.58(m, 1H), 4.07(b, 1H), 3.17(m, 1H), 2.94(s, 3H), 2.75(m, 1H), 2.61 (m, 1H), 1.90–1.50(m, 5H), 1.38 (m, 3H), 1.12(m, 3H), 0.92(m, 3H) | 446 |
| 10O | (CDCl₃) δ 9.44(d, J=1.2Hz, 1H), 8.55(s, 1H), 7.51(m, 2H), 7.22(s, 1H), 6.85(m, 1H), 4.78 (m, 1H), 4.52(m, 1H), 3.81(m, 1H), 3.27(m, 1H), 3.08(m, 1H), 2.92(s, 3H), 2.65(m, 1H), 2.34 (m, 2H), 2.16(m, 2H), 2.10–1.40 (m, 6H) | 430 |
| 10P | (CDCl₃) δ 9.44(s, 1H), 8.55(s, 1H), 7.51(m, 2H), 7.28(s, 1H), 6.83(m, 1H), 4.92(b, 1H), 4.55 (m, 1H), 4.15(b, 1H), 3.17(m, 1H), 2.92(s, 3H), 2.62(m, 1H), 2.54(m, 1H), 1.90–1.40(m, 8H), 0.87(m, 6H) | 446 |

-continued
| STRUCTURE | ¹H NMR | MS (M + H)⁺ |
|---|---|---|
| 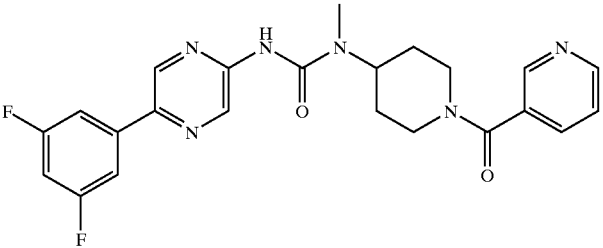<br>10Q | (CDCl₃) δ 9.42(d, J=1.6Hz, 1H), 8.68(bs, 2H), 8.55(d, J=1.6Hz, 1H), 7.76(m, 1H), 7.51 (m, 2H), 7.38(m, 1H), 7.28(s, 1H), 6.83(m, 1H), 4.90(bs, 1H), 4.80(m, 1H), 3.85(bs, 1H), 3.25 (bs, 1H), 2.97(s, 3H), 2.90(bs, 1H), 2.00–1.50(m, b, 4H) | 453 |
| 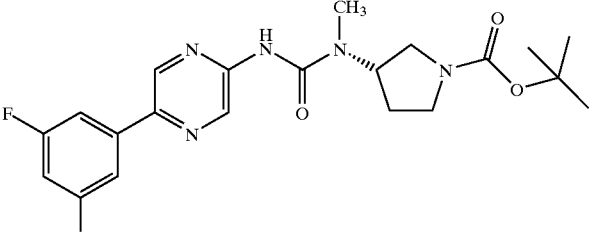<br>10R | ¹HNMR (CDCl₃) δ 9.44(d, 1H), 8.62(bs., 1H), 8.55(d, 1H), 7.51 (m, 2H), 6.84(m, 1H), 5.06(m, 1H), 3.70–3.10(m, 4H), 3.01(s, 3H), 2.12(m, 1H), 1.98(m, 1H), 1.47(s, 9H). | 434 |
| 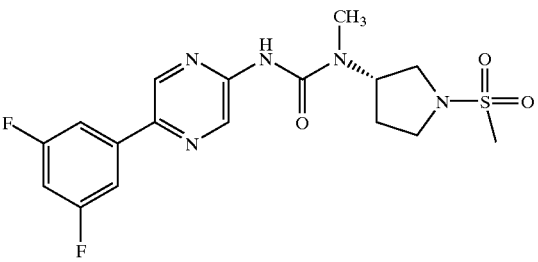<br>10S | (CDCl₃) δ 9.42(s, 1H), 8.58(s, 1H), 7.52(m, 2H), 7.24(s, 1H), 6.85(m, 1H), 5.16(m, 1H), 3.67 (m, 1H), 3.51(m, 1H), 3.37(m, 1H), 3.25(m, 1H), 3.09(s, 3H), 2.89(s, 3H), 2.26(m, 1H), 2.10 (m, 1H) | 412 |
| 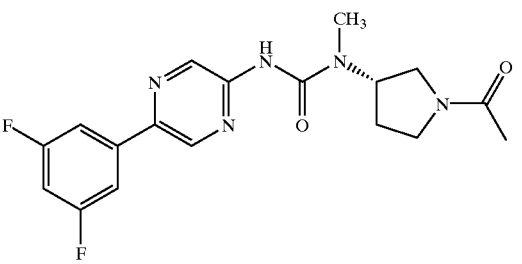<br>10T | (CDCl₃) δ 9.42(s, 1H), 8.56(m, 1H), 7.50(m, 2H), 7.32(d, 1H), 6.84(m, 1H), 5.11(m, 1H), 3.82–3.28(m, 4H), 3.01(d, 3H), 2.32–1.90(m, 5H) | 376 |
| 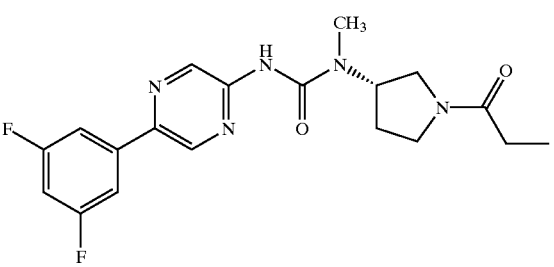<br>10U | (CDCl₃) δ 9.42(s, 1H), 8.56(m, 1H), 7.50(m, 2H), 7.27(d, 1H), 6.84(m, 1H), 5.11(m, 1H), 4.87–3.25(m, 4H), 3.02(d, 3H), 2.40–1.90(m, 4H), 1.15(m, 3H) | 390 |

| STRUCTURE | ¹H NMR | MS (M + H)⁺ |
|---|---|---|
| 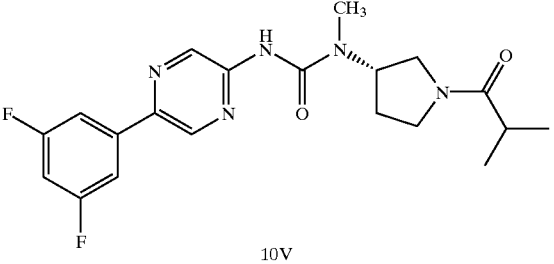<br>10V | (CDCl₃) δ 9.43(s, 1H), 8.57(bs, 1H), 7.51(m, 2H), 2.27(s, 1H), 6.83(m, 1H), 5.09(m, 1H), 3.90–3.30(m, 4H), 3.03(d, 3H), 2.65 (m, 1H), 2.30–1.90(m, 2H), 1.14 (m, 6H) | 404 |
| 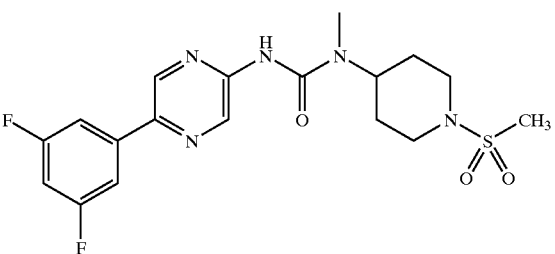<br>10W | (CDCl₃) δ 9.44(s, 1H), 8.56(s, 1H), 7.52(m, 2H), 7.25(s, 1H), 6.85(m, 1H), 4.43(m, 1H), 3.94 (b, 2H), 2.98(s, 3H), 2.81(m, 5H), 1.84(m, 4H) | 426 |
| 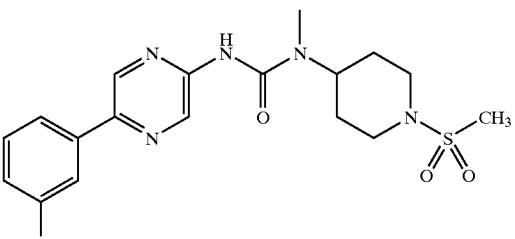<br>10X | (CDCl₃) δ 9.42(s, 1H), 8.58(s, 1H), 7.71(m, 2H), 7.42(m, 1H), 7.19(s, 1H), 7.10(m, 1H), 4.42 (m, 1H), 3.92(m, 2H), 2.97(s, 3H), 2.80(s, 5H), 1.83(m, 4H). | 408 |
| 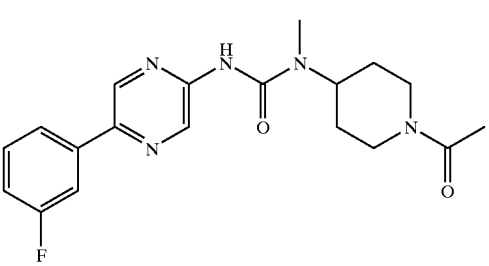<br>10Y | (CDCl₃) δ 9.42(d, J=1.6Hz, 1H), 8.57(s, 1H), 7.72(m, 2H), 7.42(m, 1H), 7.24(s, 1H), 7.08 (m, 1H), 4.79(m, 1H), 4.53(m, 1H), 3.91(m, 1H), 3.19(m, 1H), 2.93(s, 3H), 2.62(m, 1H), 2.12 (s, 3H), 1.90–1.50(m, 4H) | 372 |
| 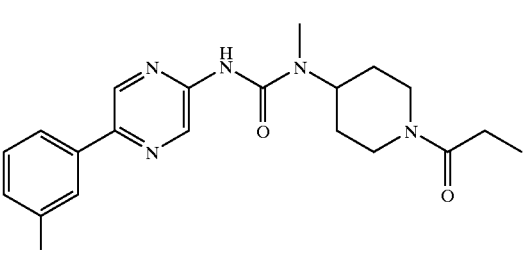<br>10Z | (CDCl₃) δ 9.44(d, J=1.6Hz, 1H), 8.57(d, J=1.6Hz, 1H), 7.71(m, 2H), 7.46(m, 1H), 7.25 (s, 1H), 7.10(m, 1H), 4.90(b, 1H), 4.53(m, 1H), 3.95(b, 1H), 3.14(m, 1H), 2.93(s, 3H), 2.61 (m, 1H), 2.37(q, 2H), 1.90–1.50 (m, 4H), 1.16(t, 3H) | 386 |

-continued

| STRUCTURE | ¹H NMR | MS (M + H)⁺ |
|---|---|---|
| 10AA | (CDCl$_3$) δ 9.44(d, J=1.6Hz, 1H), 8.58(d, J=1.2Hz, 1H), 7.71(m, 2H), 7.43(m, 1H), 7.19 (s, 1H), 7.11(m, 1H), 4.93(b, 1H), 4.58(m, 1H), 4.08(b, 1H), 3.18(m, 1H), 2.94(s, 3H), 2.82 (m, 1H), 2.63(m, 1H), 1.90–1.50 (m, 4H), 1.14(m, 6H) | 400 |
| 10BB | (CDCl$_3$) δ 9.45(s, 1H), 8.59(s, 1H), 7.72(m, 2H), 7.45(m, 1H), 7.20(s, 1H), 7.11(m, 1H), 4.78 (m, 1H), 4.58(m, 1H), 4.37(b, 1H), 3.24(m, 1H), 2.95(s, 3H), 2.88(m, 1H), 1.90–1.50(m, 5H), 0.99(m, 2H), 0.78(m, 2H) | 398 |
| 10CC | (CDCl$_3$) δ 9.48(d, J=1.6Hz, 1H), 8.72(d, J=1.6Hz, 1H), 7.79(m, 1H), 7.21(s, 1H), 7.15 (m, 1H), 7.07(m, 1H), 4.81(b, 1H), 4.57(m, 1H), 3.93(b, 1H), 3.21(t, 1H), 2.94(s, 3H), 2.63(t, 1H), 2.12(s, 3H), 1.90–1.50(m, 4H) | 390 |
| 10DD | (CDCl$_3$) δ 9.47(d, J=1.6Hz, 1H), 8.71(m, 1H), 7.78(m, 1H), 7.27(s, 1H), 7.15(m, 1H), 7.07 (m, 1H), 4.81(b, 1H), 4.57(m, 1H), 3.95(b, 1H), 3.15(t, 1H), 2.93(s, 3H), 2.63(t, 1H), 2.37(q, 2H), 1.90–1.50(m, 4H), 1.16(t, 3H) | 404 |
| 10EE | (CDCl$_3$) δ 9.48(d, J=1.6Hz, 1H), 8.72(m, 1H), 7.78(m, 1H), 7.23(s, 1H), 7.15(m, 1H), 7.07 (m, 1H), 4.82(b, 1H), 4.55(m, 1H), 4.04(b, 1H), 3.17(b, 1H), 2.94(s, 3H), 2.82(m, 1H), 2.62 (b, 1H), 1.90–1.50(m, 4H), 1.15 (m, 6H) | 418 |

| STRUCTURE | ¹H NMR | MS (M + H)⁺ |
|---|---|---|
| 10FF | (CDCl$_3$) δ 9.48(d, J=1.6Hz, 1H), 8.71(m, 1H), 7.78(m, 1H), 7.31(s, 1H), 7.15(m, 1H), 7.07 (m, 1H), 4.78(b, 1H), 4.55(m, 1H), 4.35(b, 1H), 3.15(b, 1H), 2.94(s, 3H), 2.65(b, 1H), 1.90–1.50(m, 5H), 0.98(m, 2H), 0.77 (m, 2H) | 416 |
| 10GG | (CDCl$_3$) δ 9.48(d, J=1.2Hz, 1H), 8.70(m, 1H), 7.78(m, 1H), 7.31(s, 1H), 7.15(m, 1H), 7.07 (m, 1H), 4.81(b, 1H), 4.55(m, 1H), 4.09(b, 1H), 3.15(b, 1H), 2.93(s, 3H), 2.87(m, 1H), 2.63 (b, 1H), 1.90–1.50(m, 12H). | 444 |
| 10HH | (CDCl$_3$) δ 9.43(d, J=1.2Hz, 1H), 8.57(d, J=1.2Hz, 1H), 7.97(d, J=1.6Hz, 1H), 7.83(m, 1H), 7.40(m, 2H), 7.22(s, 1H), 4.78(m, 1H), 4.53(m, 1H), 3.90 (m, 1H), 3.19(m, 1H), 2.93(s, 3H), 2.62(m, 1H), 2.12(s, 3H), 1.79(m, 2H), 1.59(m, 2H) | 388 |
| 10II | (CDCl$_3$) δ 9.43(d, J=1.6Hz, 1H), 8.57(d, J=1.6Hz, 1H), 7.97(m, 1H), 7.85(m, 1H), 7.40 (m, 2H), 7.23(s, 1H), 4.81(m, 1H), 4.55(m, 1H), 3.97(b, 1H), 3.15(b, 1H), 2.93(s, 3H), 2.64 (b, 1H), 2.37(q, 2H), 1.90–1.50 (m, 4H), 1.16(t, 3H) | 402 |
| 10JJ | (CDCl$_3$) δ 9.42(d, J=1.6Hz, 1H), 8.56(d, J=2.0Hz, 1H), 7.95(m, 1H), 7.81(m, 1H), 7.39 (m, 2H), 7.21(s, 1H), 4.81(b, 1H), 4.55(m, 1H), 4.05(b, 1H), 3.17(b, 1H), 2.92(s, 3H), 2.81 (m, 1H), 2.61(b, 1H), 1.78(m, 2H), 1.59(m, 2H), 1.12(m, 6H) | 416 |

-continued
| STRUCTURE | ¹H NMR | MS (M + H)⁺ |
|---|---|---|
| 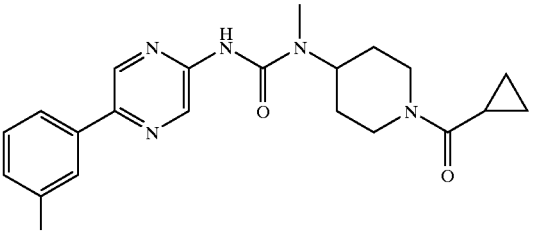<br>10KK | (CDCl₃) δ 9.44(d, J=1.2Hz, 1H), 8.57(d, J=1.2Hz, 1H), 7.97(m, 1H), 7.82(m, 1H), 7.39 (m, 2H), 7.22(s, 1H), 4.78(m, 1H), 4.55(m, 1H), 4.35(m, 1H), 3.23(m, 1H), 2.94(s, 3H), 2.86 (m, 1H), 1.90–1.50(m, 5H), 0.99 (m, 2H), 0.78(m, 2H) | 414 |
| 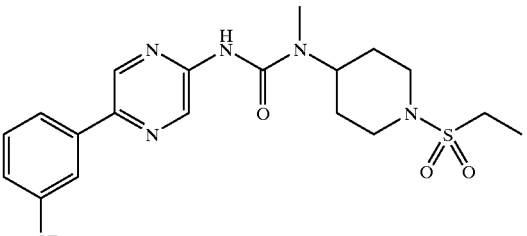<br>10LL | (CDCl₃) δ 9.46(s, 1H), 8.64(s, 1H), 8.24(s, 1H), 8.14(d, 1H), 7.63(m, 2H), 7.20(s, 1H), 4.48 (m, 1H), 3.97(b, 2H), 2.98(m, 7H), 1.81(m, 4H), 1.37(t, 3H) | 458 |
| 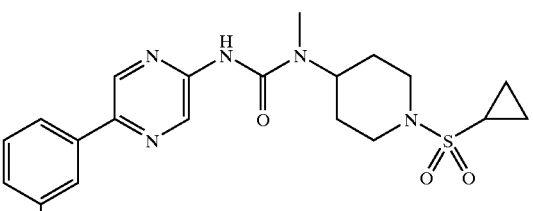<br>10MM | (CDCl₃) δ 9.46(s, 1H), 8.64(s, 1H), 8.24(s, 1H), 8.14(d, 1H), 7.61(m, 2H), 7.21(s, 1H), 4.45 (m, 1H), 3.93(b, 2H), 2.98(m, 5H), 2.28(m, 1H), 1.82(m, 4H), 1.19(m, 2H), 0.99(m, 2H) | 484 |
| 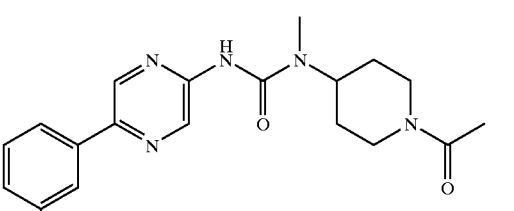<br>10NN | (CDCl₃) δ 9.48(s, 1H), 8.63(s, 1H), 8.24(s, 1H), 8.17(d, 1H), 7.63(m, 2H), 7.24(s, 1H), 4.79 (b, 1H), 4.57(m, 1H), 3.92(b, 1H), 3.12(t, 1H), 2.95(s, 3H), 2.63(t, 1H), 2.13(s, 3H), 1.90 (m, 2H), 1.82(m, 2H) | 422 |
| 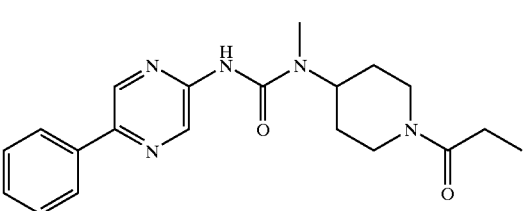<br>10OO | (CDCl₃) δ 9.47(s, 1H), 8.63(s, 1H), 8.24(s, 1H), 8.17(d, 1H), 7.63(m, 2H), 7.21(s, 1H), 4.83 (b, 1H), 4.55(m, 1H), 3.98(b, 1H), 3.18(t, 1H), 2.94(s, 3H), 2.63(t, 1H), 2.38(q, 2H), 1.90–1.50(m, 4H), 1.16(t, 3H) | 436 |

-continued

| STRUCTURE | ¹H NMR | MS (M + H)⁺ |
|---|---|---|
| 10PP | (CDCl₃) δ 9.47(s, 1H), 8.63(s, 1H), 8.24(s, 1H), 8.15(d, 1H), 7.62(m, 2H), 7.22(s, 1H), 4.83 (b, 1H), 4.58(m, 1H), 4.05(b, 1H), 3.19(t, 1H), 2.94(s, 3H), 2.82(m, 1H) 2.63(b, 1H), 1.90–1.50(m, 4H), 1.14(m, 6H) | 450 |
| 10QQ | (CDCl₃) δ 9.48(s, 1H), 8.63(s, 1H), 8.24(s, 1H), 8.15(d, 1H), 7.62(m, 2H), 7.22(s, 1H), 4.79 (b, 1H), 4.58(m, 1H), 4.37(b, 1H), 3.22(b, 1H), 2.95(s, 3H), 2.67(b, 1H), 2.90–1.50(m, 5H), 0.99(m, 2H), 0.78(m, 2H) | 448 |
| 10RR | (CDCl₃) δ 9.46(d, J=1.2Hz, 1H), 8.71(bs, 2H), 8.63(d, J=1.2Hz, 1H), 8.24(s, 1H), 8.15(d, J=8.0Hz, 1H), 7.78(d, J=7.6Hz, 1H), 7.67(d, J=8.4Hz, 1H), 7.60(t, J=8.0Hz, 1H), 7.39(m, b, 1H), 7.29(s, 1H), 4.90(bs, 1H), 4.62(m, 1H), 3.83(bs, 1H), 3.23(bs, 1H), 2.99(s, 3H), 2.90 (bs, 1H), 1.90–1.50(m, 4H) | 485 |

EXAMPLE 11

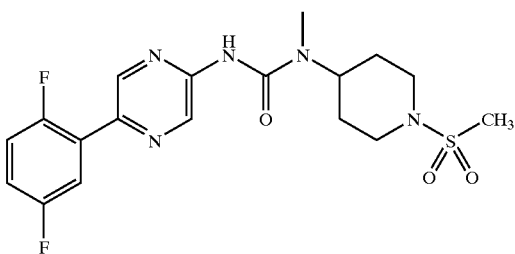

Step 1

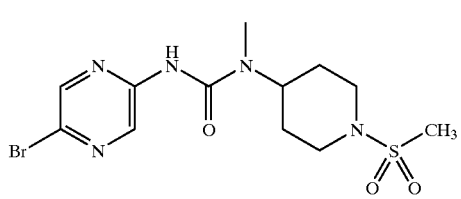

11-1

Reaction of 2-amino-5-bromopyrazine and Preparation 11 by the procedure of Example 10, Step 2 gave the product. ¹HNMR (CDCl₃) δ 9.18 (d, J=1.2Hz, 1H), 8.26 (d, J=1.2Hz, 1H), 7.11 (s, 1H), 4.42 (m, 1H), 3.93 (m, 2H), 2.95 (s, 3H), 2.79 (m, 5H), 1.81 (m, 4H). MS m/e 394 (M+H)⁺.

Step 2

A flask charged with 11-1 (0.090 g, 0.23 mmol), 2,5-difluorophenylboronic acid (0.044 g, 0.28 mmol), toluene (10 ml), water (0.3 ml) and cesium carbonate (0.082 g, 0.25 mmol) was purged with N₂. PdCl₂(dppf)₂CH₂Cl₂ (0.015 g, 0.019 mmol) was added and the reaction mixture was refluxed for 3 hr, allowed to cool, and filtered. The concentrated filtrate was subjected to PTLC (1:1 acetone/hexane) to give the product (0.046 g, 47%). ¹H NMR (CDCl₃) δ 9.47 (d, J=1.6Hz, 1H), 8.72 (m, 1 H), 7.78 (m, 1H), 7.22 (s, 1H), 7.15 (m, 1H), 7.06 (m, 1H), 4.48 (m, 1H), 3.95 (m, 2H), 2.98 (s, 3H), 2.83 (m, 5H), 1.86 (m, 4H). MS m/e 426 (M+H)⁺.

Use of the appropriate boronic acid and essentially the same procedure afforded the following compounds:

| STRUCTURE | ¹H NMR | MS (M + H)⁺ |
|---|---|---|
| 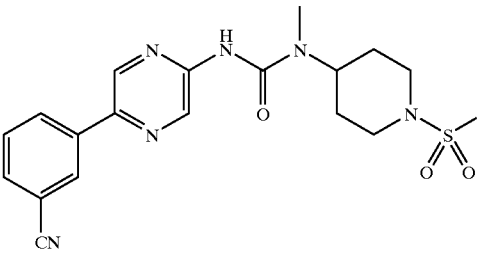<br>11A | (CDCl₃) δ 9.46(s, 1H), 8.62(s, 1H), 8.29(s, 1H), 8.20(m, 1H), 7.69(m, 1H), 7.60(m, 1H), 7.22 (m, 1H), 4.44(m, 1H), 3.95(m, 2H), 2.98(s, 3H), 2.81(m, 5H), 1.83(m, 4H). | 415 |
| 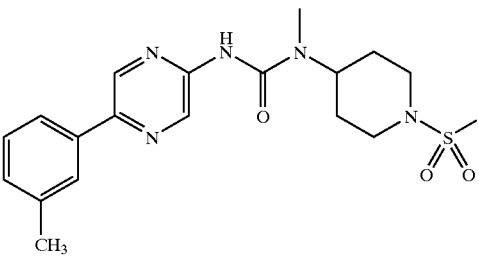<br>11B | (CDCl₃) δ 9.43(s, 1H), 8.59(s, 1H), 7.80(s, 1H), 7.75(d, 1H), 7.37(t, 1H) 7.25(d, 1H), 7.16(s, 1H), 4.50(m, 1H), 3.95(b, 2H), 2.97(s, 3H), 2.82(m, 5H), 2.44 (s, 3H), 1.84(m, 4H) | 404 |
| 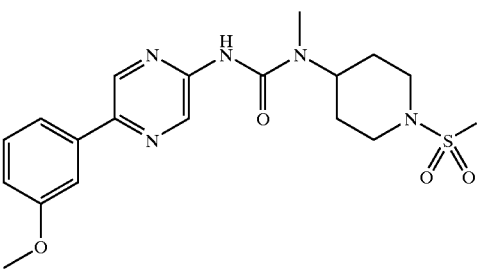<br>11C | (CDCl₃) δ 9.42(d, J=1.6Hz, 1H), 8.59(s, 1H), 7.52(m, 2H), 7.39(t, 1H), 7.16(s, 1H), 6.97 (m, 1H), 4.48(m, 1H), 3.94(b, 2H), 3.89(s, 3H), 2.97(s, 3H), 2.81(m, 5H), 1.84(m, 4H) | 420 |
| 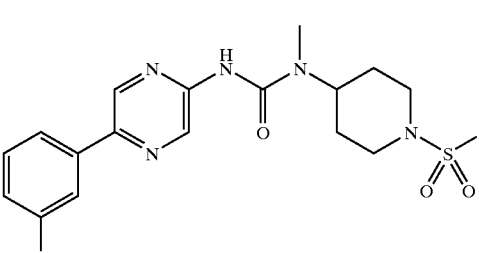<br>11D | (CDCl₃) δ 9.47(s, 1H), 8.64(s, 1H), 8.24(s, 1H), 8.14(d, 1H), 7.63(m, 2H), 7.26(s, 1H), 4.49 (bs, 1H), 3.94(b, 2H), 2.98(s, 3H), 2.81(bs, 5H), 1.85(bs, 4H) | 458 |
| 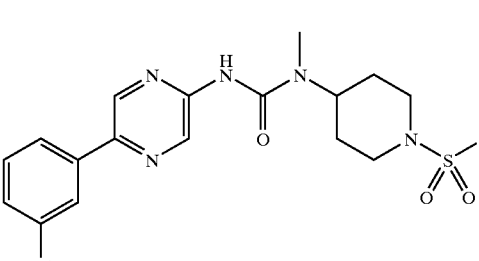<br>11E | (CDCl₃) δ 9.42(s, 1H), 8.60(s, 1H), 7.98(s, 1H), 7.84(m, 1H), 7.40(m, 2H), 7.19(s, 1H), 4.42 (m, 1H), 3.90(m, 2H), 2.97(s, 3H), 2.81(m, 5H), 1.84(m, 4H). | 424 |

EXAMPLE 12

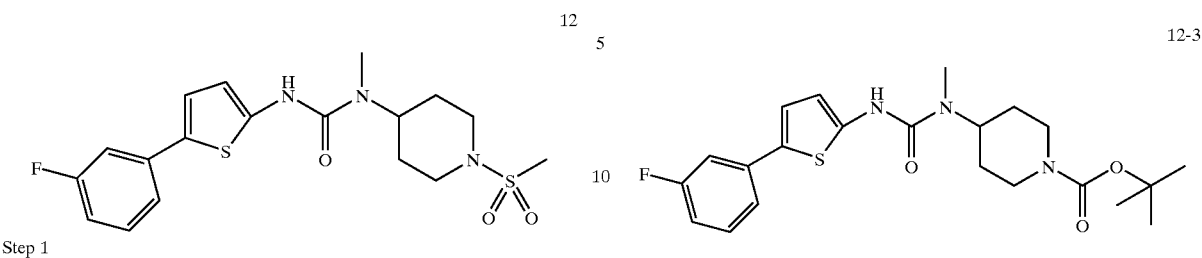

Step 1

Reaction of 3-fluorophenylboronic acid with 2-bromo-5-nitrothiophene by essentially the procedure of Example 1, Step 1 gave the product. ¹H NMR (CDCl₃, 400 MHz) δ 7.91 (1H, m), 7.42 (2H, m), 7.32 (1H, m), 7.25 (1H, m), 7.14 (1H, m).

Step 2

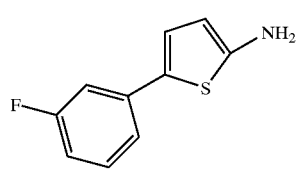

Reaction of the product of Step 1 with NiCl₂·6H₂O and NaBH₄ by essentially the procedure of Example 2, Step 2 gave the product. ¹H NMR (CDCl₃, 400 MHz) δ 7.25 (2H, m), 7.14 (1H, m), 6.48 (1H, d, J=2Hz), 6.85 (1H, m), 6.15 (1H, d, J=2Hz), 3.87 (2H, b).

Step 3

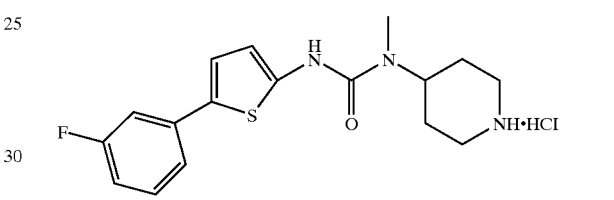

Reaction of the product of Step 2 with N,N'-disuccinimidyl carbonate and Preparation 1 by the procedure of Example 2, Step 3 gave the product. ¹H NMR (CDCl₃, 400 MHz) δ 7.25 (3H, m), 7.06 (1H, m), 7.05 (1H, d, J=4Hz), 6.89 (1H, m), 6.50 (1H, d, J=4Hz), 4.44 (1H, m), 4.22 (2H, m), 2.86 (3H, s), 2.79 (2H, m), 1.60 (4H, m) 1.47 (9H, s). MS m/e 434 (M+H)⁺.

Step 4

Reaction of the product of Step 3 with HCl by essentially the procedure of Example 6, Step 4 gave the product. ¹H NMR (CD₃OD, 400 MHz) δ 7.36–7.24 (4H, m), 6.90 (1H, m), 6.73 (1H, m), 4.37 (1H, m), 3.50 (2H, m), 3.13 (2H, m), 2.96 (3H, s), 2.09–1.91 (4H, m).

Step 5

Reaction of the product of Step 4 with methanesulfonyl chloride by essentially the procedure of Example 3, Step 3 gave the product. ¹H NMR (CDCl₃, 400 MHz) δ 7.45 (1H, s), 7.29 (3H, m), 7.05 (1H, d, J=4Hz), 6.88 (1H, m), 6.54 (1H, d, J=4Hz), 4.40 (1H, m), 3.86 (2H, m), 2.87 (3H, s), 2.74 (3H, s), 2.68 (2H, m), 1.76 (4H, m). MS m/e 412 (M+H)⁺.

Use of the appropriate reagents and procedures afforded the following compounds.

| STRUCTURE | ¹H NMR | MS (M + H)⁺ |
|---|---|---|
| 12A | | 430 |

-continued
| STRUCTURE | ¹H NMR | MS (M + H)⁺ |
|---|---|---|
| 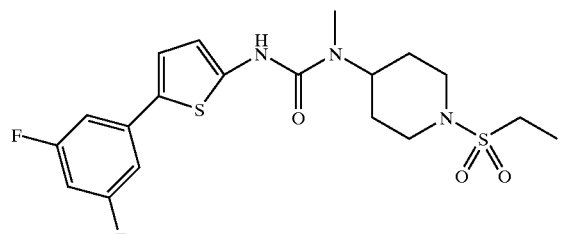 12B | | 444 |
| 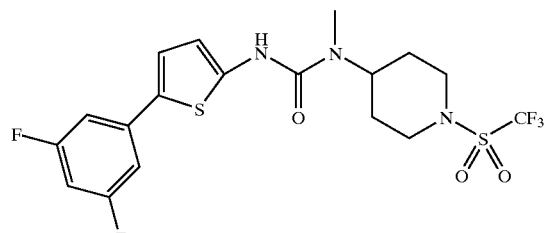 12C | | 484 |
| 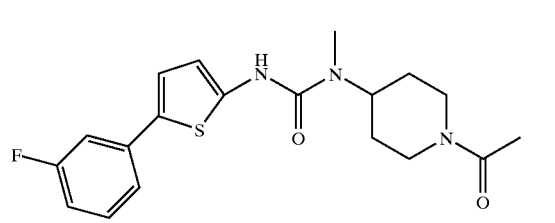 12D | (CDCl₃) δ 7.46(1H, s), 7.28 (3H, m), 7.03(1H, s), 6.86(1H, m), 6.51(1H, s), 4.74(1H, m), 4.53(1H, m), 3.85(1H, m), 3.14 (1H, m), 2.86(3H, s), 2.58(1H, m), 2.10(3H, s), 1.78(2H, m), 1.58(2H, m) | 376 |
| 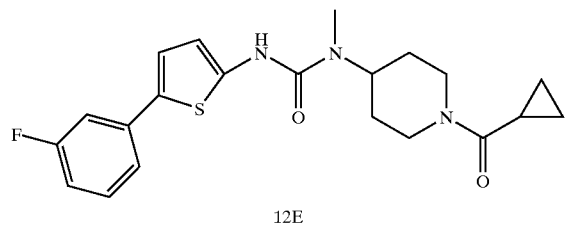 12E | (CDCl₃) δ 7.63(1H, s), 7.29 (3H, m), 7.03(1H, d, J=4Hz), 6.87(1H, m), 6.49(1H, d, J=4Hz), 4.70(1H, m), 4.52(1H, m), 4.30(1H, m), 3.15(1H, m), 2.85 (3H, s), 2.61(1H, m), 1.72(3H, m), 1.58(2H, m), 0.95(2H, m), 0.74(2H, m). | 402 |
| 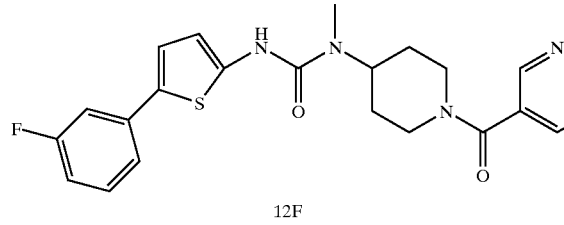 12F | (CDCl₃) δ 8.66(2H, m), 7.75(1H, d, J=7.6Hz), 7.56(1H, s), 7.38 (1H, m), 7.28(3H, m), 7.07(1H, d, J=4Hz), 6.87(1H, m), 6.49 (1H, d, J=4Hz), 4.87(1H, m), 4.57(1H, m), 3.78(1H, m), 3.17 (1H, m), 2.88(3H, s), 2.84(1H, m), 1.81–1.56(4H, m). | 439 |
| 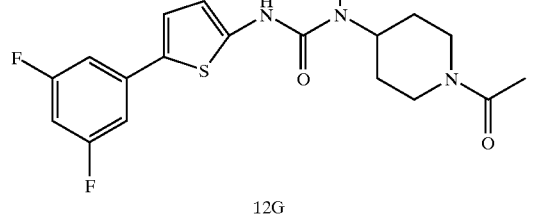 12G | (CDCl₃) δ 7.68(s, 1H), 7.03(m, 3H), 6.61(m, 1H), 6.50(m, 1H), 4.75(m, 1H), 4.50(m, 1H), 3.89 (m, 1H), 3.15(m, 1H), 2.87(s, 3H), 2.59(m, 1H), 2.10(s, 3H), 1.75(m, 2H), 1.58(m, 2H). | 394 |

-continued
| STRUCTURE | ¹H NMR | MS (M + H)⁺ |
|---|---|---|
| 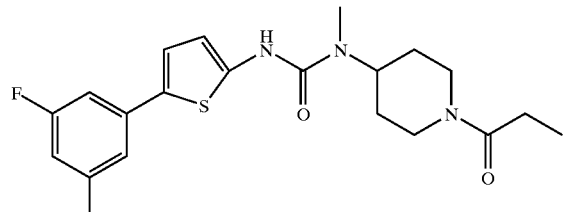<br>12H | (CDCl₃) δ 7.46(s, 1H), 7.04(m, 3H), 6.62(m, 1H), 6.50(m, 1H), 4.77(m, 1H), 4.51(m, 1H), 3.94 (m, 1H), 3.09(m, 1H), 2.87(s, 3H), 2.59(m, 1H), 2.36(q, J= 7.6Hz, 2H), 1.75(m, 2H), 1.57 (m, 2H), 1.15(t, J=7.6Hz, 3H). | 408 |
| 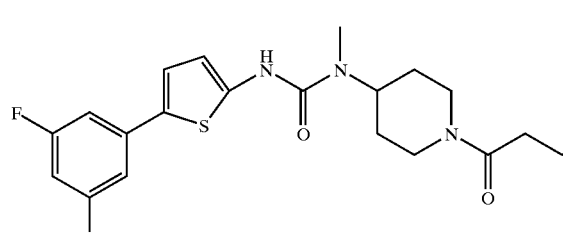<br>12I | (CDCl₃) δ 7.33(s, 1H), 7.03(m, 3H), 6.63(m, 1H), 6.50(m, 1H), 4.78(m, 1H), 4.52(m, 1H), 3.95 (m, 1H), 3.11(m, 1H), 2.87(s, 3H), 2.58(m, 1H), 2.33(m, 2H), 1.4–1.8(m, 6H), 0.97(t, J=7.6Hz, 3H). | 422 |
| 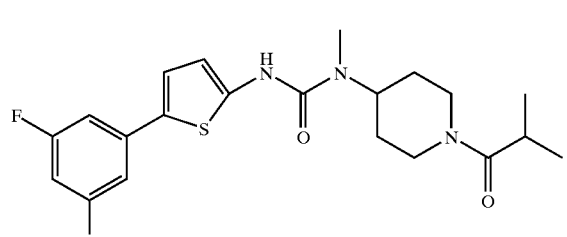<br>12J | (CDCl₃) δ 7.27(s, 1H), 7.04(m, 3H), 6.63(m, 1H), 6.50(m, 1H), 4.79(m, 1H), 4.54(m, 1H), 4.02 (m, 1H), 3.13(m, 1H), 2.88(s, 3H), 2.82(m, 1H), 2.58(m, 1H), 1.75(m, 2H), 1.56(m, 2H), 1.14 (m, 6H). | 422 |
| 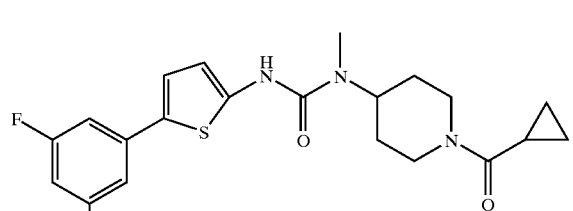<br>12K | (CDCl₃) δ 7.44(b, 1H), 7.05(m, 3H), 6.63(m, 1H), 6.49(m, 1H), 4.74(m, 1H), 4.54(m, 1H), 4.32 (m, 1H), 3.18(m, 1H), 2.87(s, 3H), 2.63(m, 1H), 1.5–1.9(m, 5H), 0.97(m, 2H), 0.78(m, 2H). | 420 |
| 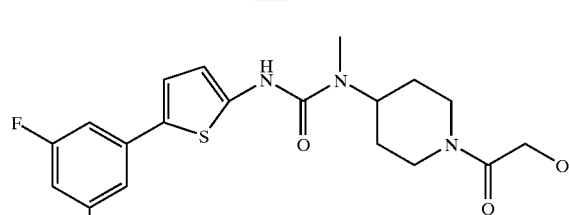<br>12L | (CDCl₃) δ 7.26(s, 1H), 7.04(m, 3H), 6.63(m, 1H), 6.50(m, 1H), 4.73(m, 1H), 4.54(m, 1H), 4.11 (m, 2H), 3.97(m, 1H), 3.43(s, 3H), 3.10(m, 1H), 2.88(s, 3H), 2.64(m, 1H), 1.77(m, 2H), 1.60 (m, 2H). | 424 |
| 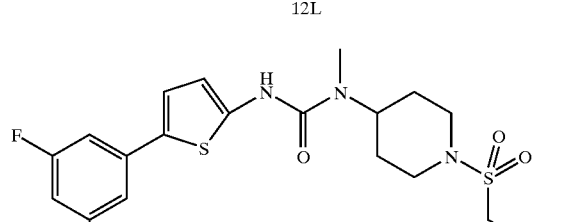<br>12M | (CDCl₃) δ 7.22(m, 1H), 7.04(m, 3H), 6.64(m, 1H), 6.52(m, 1H), 4.45(m, 1H), 3.92(m, 2H), 2.90 (s, 3H), 2.84(m, 4H), 1.80(m, 6H), 1.06(t, J=7.4Hz, 3H). | 458 |

| STRUCTURE | ¹H NMR | MS (M + H)⁺ |
|---|---|---|
| 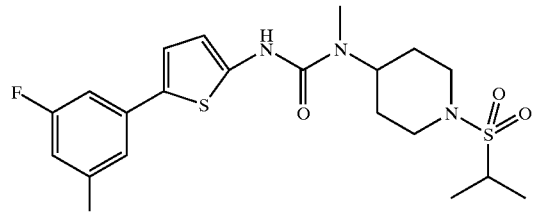<br>12N | (CDCl₃) δ 7.23(m, 1H), 7.04(m, 3H), 6.63(m, 1H), 6.52(m, 1H), 4.47(m, 1H), 3.94(m, 2H), 3.19 (m, 1H), 2.96(m, 2H), 2.90(s, 3H), 1.74(m, 4H), 1.33(d, J= 7.2Hz, 6H). | 458 |

EXAMPLE 13

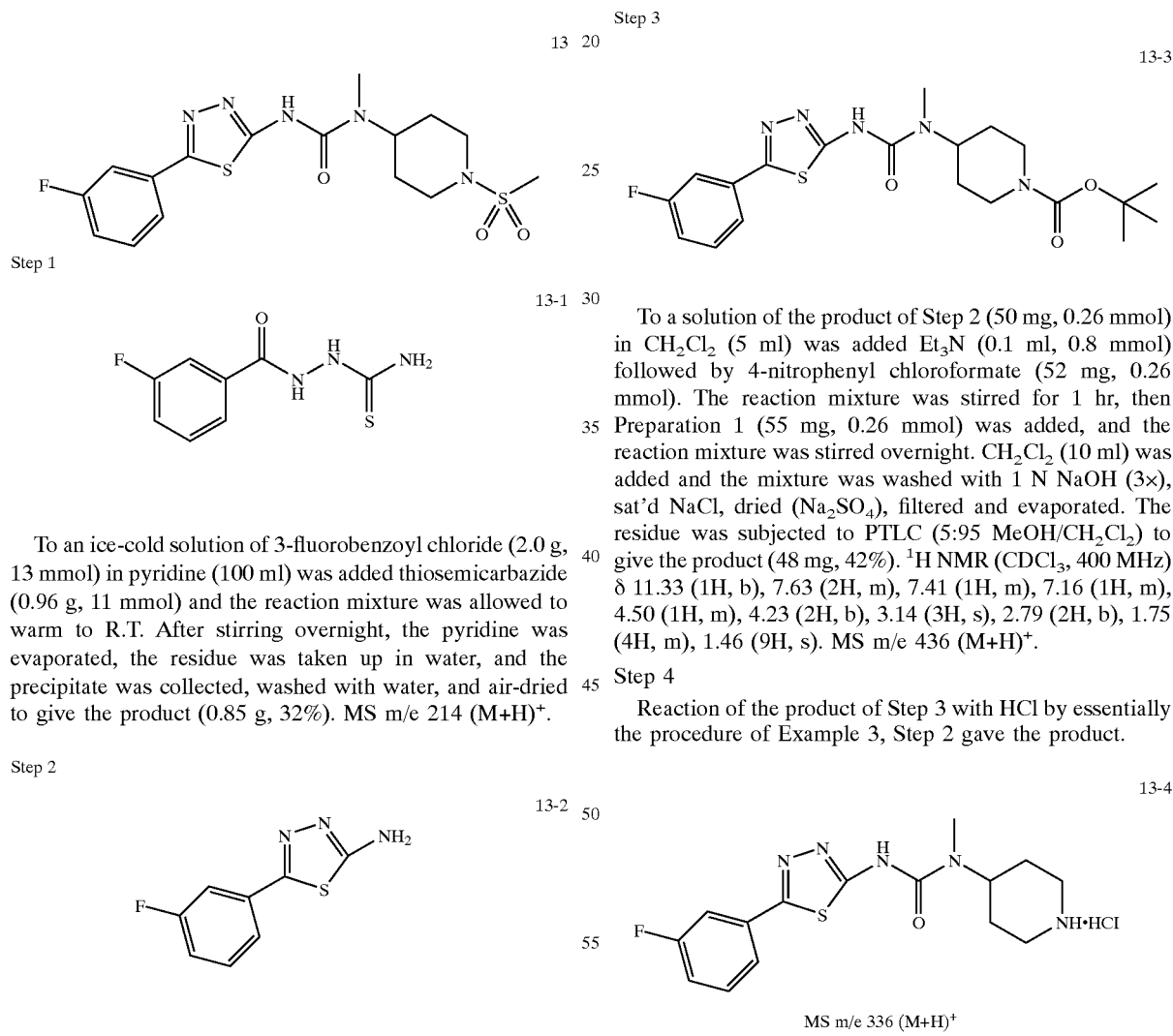

Step 1

To an ice-cold solution of 3-fluorobenzoyl chloride (2.0 g, 13 mmol) in pyridine (100 ml) was added thiosemicarbazide (0.96 g, 11 mmol) and the reaction mixture was allowed to warm to R.T. After stirring overnight, the pyridine was evaporated, the residue was taken up in water, and the precipitate was collected, washed with water, and air-dried to give the product (0.85 g, 32%). MS m/e 214 (M+H)⁺.

Step 2

To a solution of the product of Step 1 (500 mg, 2.34 mmol,) in toluene (10 ml) was added methanesulfonic acid (0.34 g, 3.5 mmol) dropwise. The reaction mixture was refluxed for 4 hr, cooled, and the precipitate was collected, washed with ether, and dried. The solid was then taken up in water, the solution was basified with ammonia to pH 8, and the precipitate was collected, washed with water, and dried to give the product (206 mg, 46%). MS m/e 196 (M+H)⁺.

Step 3

To a solution of the product of Step 2 (50 mg, 0.26 mmol) in CH₂Cl₂ (5 ml) was added Et₃N (0.1 ml, 0.8 mmol) followed by 4-nitrophenyl chloroformate (52 mg, 0.26 mmol). The reaction mixture was stirred for 1 hr, then Preparation 1 (55 mg, 0.26 mmol) was added, and the reaction mixture was stirred overnight. CH₂Cl₂ (10 ml) was added and the mixture was washed with 1 N NaOH (3×), sat'd NaCl, dried (Na₂SO₄), filtered and evaporated. The residue was subjected to PTLC (5:95 MeOH/CH₂Cl₂) to give the product (48 mg, 42%). ¹H NMR (CDCl₃, 400 MHz) δ 11.33 (1H, b), 7.63 (2H, m), 7.41 (1H, m), 7.16 (1H, m), 4.50 (1H, m), 4.23 (2H, b), 3.14 (3H, s), 2.79 (2H, b), 1.75 (4H, m), 1.46 (9H, s). MS m/e 436 (M+H)⁺.

Step 4

Reaction of the product of Step 3 with HCl by essentially the procedure of Example 3, Step 2 gave the product.

MS m/e 336 (M+H)⁺

Step 5

Reaction of the product of Step 4 with methanesulfonyl chloride by essentially the procedure of Example 3, Step 3 gave the product. ¹H NMR (CDCl₃, 400 MHz) δ 7.64 (2H, m), 7.48 (1H, m), 7.17 (1H, m), 4.44 (1H, m), 3.95 (2H, m), 3.06 (3H, s), 2.81 (3H, s), 2.80 (2H, m), 1.90 (4H, m). MS m/e 414 (M+H)⁺.

EXAMPLE 14

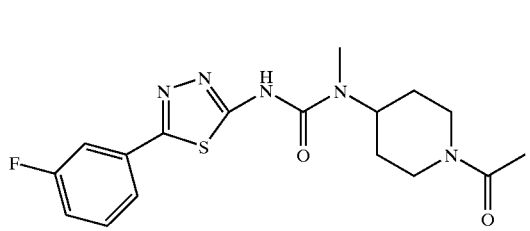

14

Reaction of the product of Example 13, Step 4 (13-4) with acetyl chloride by essentially the procedure of Example 4 gave the product. $^1$H NMR (CDCl$_3$, 400 MHz) δ 11.00 (1H, b), 7.65 (2H, m), 7.50 (1H, m), 7.17 (1H, m), 4.80 (1H, m), 4.55 (1H, m), 3.94 (1H, m), 3.20 (1H, m), 3.09 (3H, s), 2.63 (1H, m), 2.13 (3H, s), 1.70 (4H, m). MS m/e 378 (M+H)$^+$.

EXAMPLE 15

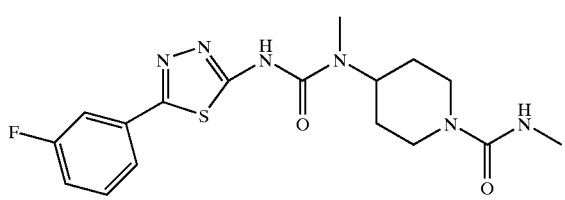

15

To an ice-cold solution of the product of Example 13, Step 4 (13-4) (25 mg, 0.074 mmol) in DMF (5 ml) was added methyl isocyanate (1 drop). The reaction mixture was allowed to warm to R.T., stirred for 3 days, then diluted with CH$_2$Cl$_2$ and washed with water, 1 N NaOH, and sat'd NaCl. The organic layer was dried (Na$_2$SO$_4$), filtered and evaporated. The residue was subjected to PTLC (10:90 MeOH/CH$_2$Cl$_2$) to give the product (9 mg, 31%). $^1$H NMR (CDCl$_3$, 400 MHz) δ 10.80 (1H, b), 7.64 (2H, m), 7.45 (1H, m), 7.19 (1H, m), 4.48 (1H, m), 4.10 (2H, m), 3.10 (3H, s), 2.90 (3H, s), 2.85 (2H, m), 1.78 (4H, m). MS m/e 393 (M+H)$^+$.

EXAMPLE 16

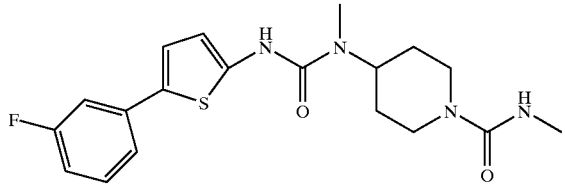

Reaction of 12-4 with methyl isocyanate by essentially the same procedure gave the product. $^1$H NMR (CDCl$_3$, 400 MHz) δ 7.48 (1H, s), 7.28 (3H, m), 7.03 (1H, d, J=4Hz), 6.87 (1H, m), 6.50 (1H, d, J=4Hz), 4.56 (1H, m), 4.44 (1H, m), 4.03 (2H, m), 2.87 (2H, m), 2.86 (3H, s), 2.80 (3H, s), 2.04–1.54 (4H, m). MS m/e 392 (M+H)$^+$.

EXAMPLE 17

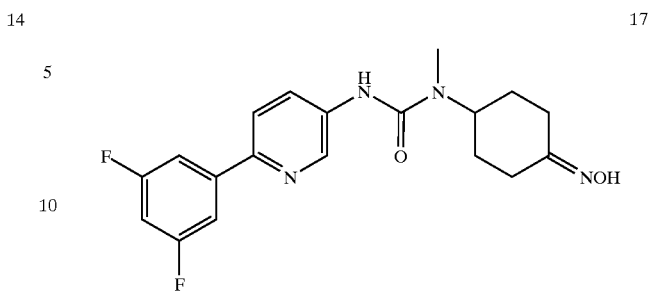

17

Step 1

17-1

To a solution of the product of Example 1, Step 2 (1-2) (250 mg, 1.21 mmol) in toluene (8 ml) was added iPr$_2$NEt (1.1 ml, 6.0 mmol) and triphosgene (145 mg, 0.49 mmol). The reaction mixture was heated to 110° C. for 4 hr, cooled, and Preparation 13 (250 mg, 1.47 mmol) was added. The reaction mixture was stirred for 16 hr, then partitioned between CH$_2$Cl$_2$ (100 ml) and 1 N NaOH (25 ml). The organic layer was washed with sat. NH$_4$Cl (25 ml) and sat'd NaCl (25 ml), dried (MgSO$_4$), filtered and concentrated. The residue was dissolved in THF (20 ml) to which 5N HCl (5 ml) was added. After 3.5 hr, the reaction mixture was cooled in an ice bath, basified to pH 12 and partitioned between CH$_2$Cl$_2$ (100 ml) and water (25 ml). The organic layer was dried (MgSO$_4$), filtered and concentrated. Subjection of the residue to PTLC (3:2 EtOAc/hexane) gave the product (130 mg, 30%). MS m/e 360 (M+H)$^+$.

Step 2

To a solution of the product of Step 1 (60 mg, 0.17 mmol) in EtOH (2.5 ml) was added NaOAc (0.27 g, 3.3 mmol) and hydroxylamine hydrochloride (0.23 g, 3.34 mmol). The reaction mixture was stirred for 16 hr. then partitioned between CH$_2$Cl$_2$ (75 ml) and water (50 ml). The organic layer was dried (MgSO$_4$), filtered and concentrated. The residue was subjected to PTLC (3:97 MeOH/CH$_2$Cl$_2$) to give the product (52 mg, 83%). $^1$H NMR (CD$_3$OD, 400 MHz) δ 8.69 (1H, m), 8.00 (1H, m), 7.80 (1H, m), 7.55 (4H, m), 6.94 (1H, m), 4.40 (1H, m), 3.45 (1H, m), 2.91 (3H, s), 2.50 (1H, m), 2.30 (1H, m), 1.90 (3H, m), 1.70 (2H, m). MS m/e 375 (M+H)$^+$.

EXAMPLE 18

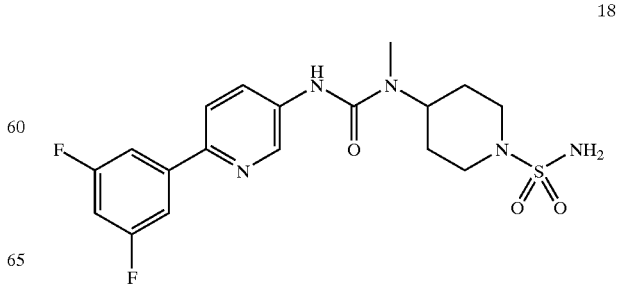

18

Reaction of the amine 1-2, N,N'-disuccinimidyl carbonate, and Preparation 12 by essentially the procedure of Example 2, Step 3 gave the product. $^1$H NMR (DMSO, 400 MHz) δ 8.76 (1H, s), 8.66 (1H, s), 7.96 (2H, m), 7.73 (2H, d), 7.21 (1H, m), 6.77 (2H, s), 4.09 (1H, m), 3.55 (2H, m), 2.85 (3H, s), 2.61 (2H, m), 1.76 (2H, m), 1.64 (2H, m). MS m/e 426 (M+H)$^+$.

EXAMPLE 19

19

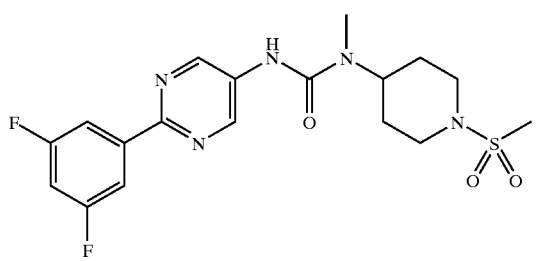

Step 1

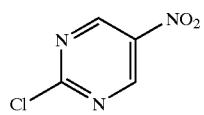

19-1

To a suspension of 2-amino-5-nitropyrimidine (2.70 g, 19.3 mmol) and LiCl (20 g) in 4M HCl (95 ml) at −10° C. was added NaNO$_2$ (2.70 g, 39.1 mmol) in portions. The suspension was stirred at ice-bath temperature for 1 hr, then allowed to warm to R.T. and stirred for 1.5 hr. The reaction mixture was cooled in an ice-bath, CH$_2$Cl$_2$ (50 ml) was added and aqueous layer was brought to pH 9 by addition of sat'd Na$_2$CO$_3$. The whole was filtered and the filtrate was extracted with CH$_2$Cl$_2$. The organic layer was dried (MgSO$_4$), filtered and evaporated to give a solid (1.05 g, 34%). $^1$H NMR (CDCl$_3$, 400 MHz) δ 9.39 (s).

Step 2

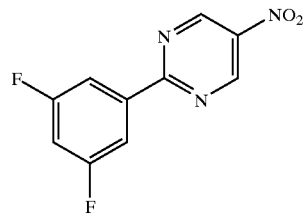

19-2

To an N$_2$-purged mixture of the product of Step 1(230 mg, 1.44 mmol), 3,5-difluorophenylboronic acid (655 mg, 2.08 mmol), CsCO$_3$ (502 mg, 1.54 mmol), H$_2$O (0.05 ml), and toluene (3 ml) was added Pd(dppf)Cl$_2$.CH$_2$Cl$_2$ (82 mg, 0.10 mmol). The reaction mixture was heated at 110° C. for 1.5 hr, then allowed to cool. EtOAc (20 ml) and H$_2$O (20 ml) was added, and the organic layer was dried (MgSO$_4$), filtered and evaporated. Flash chromatography of the residue (1:99 EtOAc/hexanes) gave the product (110 mg, 32%). $^1$H NMR (CDCl$_3$, 400 MHz) δ 9.54 (2H, s), 8.08 (2H, m), 7.03 (1H, m).

Step 3

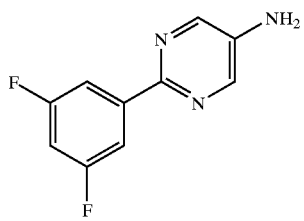

19-3

To an ice-cold suspension of the product of Step 2 (110 mg, 0.46 mmol) and NiCl$_2$.6H$_2$O (240 mg, 1.01 mmol) in MeOH (4 ml) was added NaBH$_4$ (57 mg, 1.51 mmol). The reaction mixture was stirred for 10 min., then H$_2$O (2 ml) was added and the mixture was concentrated. To the residue were added H$_2$O (20 ml) and CH$_2$Cl$_2$ (30 ml), and the whole was filtered. The organic layer of the filtrate was dried (Na$_2$SO$_4$), filtered and evaporated to give a solid (72 mg, 75%). MS (m/e) 208 (M+H)$^+$.

Step 4

Reaction of the product of Step 3 (70 mg, 0.34 mmol) with Preparation 11 (98 mg, 0.51 mmol) by the procedure of Example 2, Step 3 gave the product (90 mg, 62%). $^1$H NMR (CDCl$_3$, 400 MHz) δ 8.91 (2H, s), 7.90 (2H, m), 6.86 (1H, m), 6.64 (1H, s), 4.42 (1H, m), 3.91 (2H, m), 2.95 (3H, s), 2.80 (5H, m), 1.81 (4H, m). MS (m/e) 426 (M+H)$^+$.

Use of the appropriate procedures afforded the following compounds:

| STRUCTURE | $^1$H NMR | MS (M + H)$^+$ |
|---|---|---|
| 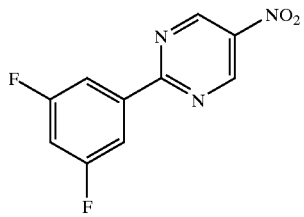<br>19A | (CDCl$_3$) δ 8.92(s, 2H), 7.90(m, 2H), 6.87(m, 1H), 6.52(s, 1H), 4.43(m, 1H), 4.22(m, 2H), 2.95(s, 3H), 2.82(m, 2H), 1.78–1.52(m, 4H), 1.47(s, 9H). | 448 |

-continued
| STRUCTURE | ¹H NMR | MS (M + H)⁺ |
|---|---|---|
| 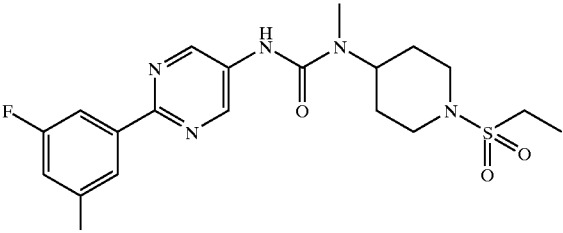<br>19B | (CDCl₃) δ 8.92(s, 2H), 7.90(m, 2H), 6.86(m, 1H), 6.52(s, 1H), 4.46(m, 1H), 3.93(m, 2H), 2.95(m, 7H), 1.81(m, 4H), 1.36(t, 3H). | 440 |
| 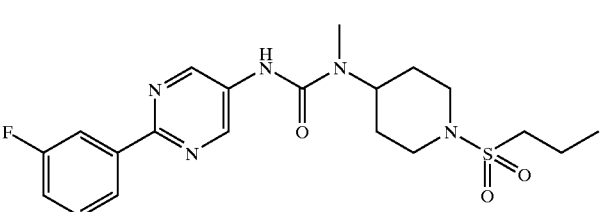<br>19C | (CD₃OD) δ 8.99(s, 2H), 7.91(m, 2H), 7.04(m, 1H), 4.28(m, 1H), 3.86(m, 2H), 2.95(m, 7H), 1.84(m, 6H), 1.07(t, 3H). | 454 |
| 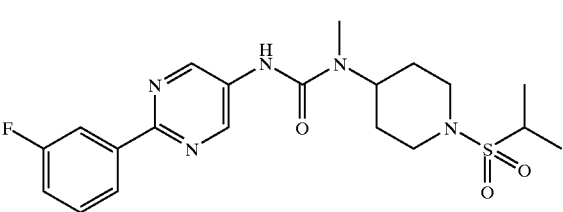<br>19D | (CDCl₃) δ 8.92(s, 2H), 7.90(m, 2H), 6.86(m, 1H), 6.49(s, 1H), 4.48(m, 1H), 3.96(m, 2H), 3.21(m, 1H), 2.95(m, 5H), 1.77(m, 4H), 1.36(m, 6H). | 454 |
| 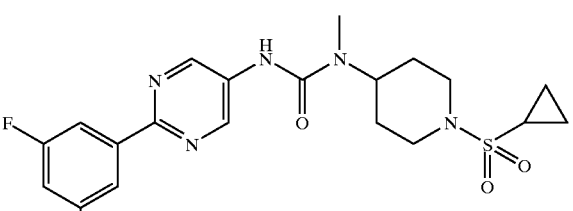<br>19E | (CDCl₃) δ 8.92(s, 2H), 7.91(m, 2H), 6.87(m, 1H), 6.63(s, 1H), 4.44(m, 1H), 3.90(m, 2H), 2.95(m, 5H), 2.28(m, 1H), 1.82(m, 4H), 1.15(m, 2H), 1.00 (m, 2H). | 452 |
| 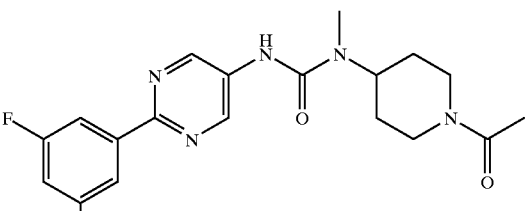<br>19F | (CDCl₃) δ 8.92(s, 2H), 7.90(m, 2H), 6.87(m, 1H), 6.77(s, 1H), 4.78(m, 1H), 4.52(m, 1H), 3.92(m, 1H), 3.18(m, 1H), 2.94(s, 3H), 2.61(m, 1H), 2.11(s, 3H), 1.82–1.57(m, 4H). | 390 |

-continued

| STRUCTURE | ¹H NMR | MS (M + H)⁺ |
|---|---|---|
| 19G | (CDCl₃) δ 8.92(s, 2H), 7.90(m, 2H), 6.87(m, 1H), 6.74(s, 1H), 4.78(m, 1H), 4.52(m, 1H), 3.95(m, 1H), 3.12(m, 1H), 2.93(s, 3H), 2.61(m, 1H), 2.38(m, 2H), 1.82–1.55(m, 4H), 1.35(t, 3H). | 404 |
| 19H | (CDCl₃) δ 8.92(s, 2H), 7.90(m, 2H), 6.87(m, 1H), 6.64(s, 1H), 4.80(m, 1H), 4.55(m, 1H), 4.06(m, 1H), 3.16(m, 1H), 2.93(s, 3H), 2.62(m, 1H), 1.79–1.57(m, 5H), 0.98(m, 2H), 0.78(m, 2H). | 416 |
| 19I | (CDCl₃) δ 8.92(s, 2H), 7.90(m, 2H), 6.87(m, 1H), 6.64(s, 1H), 4.81(m, 1H), 4.53(m, 1H), 4.06(m, 1H), 3.16(m, 1H), 2.94(s, 3H), 2.80(m, 1H), 2.59(s, 1H), 1.79(m, 2H), 1.57(m, 2H), 1.14 (m, 6H). | 418 |
| 19J | (CD₃OD) δ 9.04(s, 2H), 7.90(m, 2H), 7.08(m, 1H), 4.69(m, 1H), 4.40(m, 1H), 4.11(m, 1H), 3.22(m, 1H), 2.95(s, 3H), 2.72(m, 1H), 2.42(t, 2H), 1.78–1.62(m, 6H), 1.00(t, 3H). | 418 |
| 19K | (CDCl₃) δ 8.92(s, 2H), 8.65(s, 2H), 7.91(d, J=6.8Hz, 2H), 7.79(s, J=7.6Hz, 1H), 7.40(m, 1H), 6.87(m, 1H), 6.56(s, 1H), 4.87(m, 1H), 4.60(m, 1H), 3.87(m, 1H), 3.24(m, 1H), 2.98(m, 4H), 1.95–1.48(m, 4H). | 453 |

-continued

| STRUCTURE | ¹H NMR | MS (M + H)⁺ |
| --- | --- | --- |
| 19L | (CDCl₃) δ 8.92(s, 2H), 8.69(m, 1H), 7.90(m, 2H), 7.80(m, 1H), 7.62(d, J= 7.2Hz, 1H), 7.36(m, 1H), 6.87(m, 1H), 6.70(s, 1H), 4.89(m, 1H), 4.60(m, 1H), 4.09(m, 1H), 3.16(m, 1H), 2.96(s, 3H), 2.88(m, 1H), 1.84–1.72(m, 4H). | 453 |
| 19M | (CDCl₃) δ 8.94(s, 2H), 8.90(s, 1H), 8.07(s, 1H), 7.90(m, 2H), 6.87(m, 1H), 6.59(s, 1H), 4.80–4.20(m, 3H), 3.30–2.80(m, 5H), 1.86–1.69(m, 4H). | 459 |

EXAMPLE 20

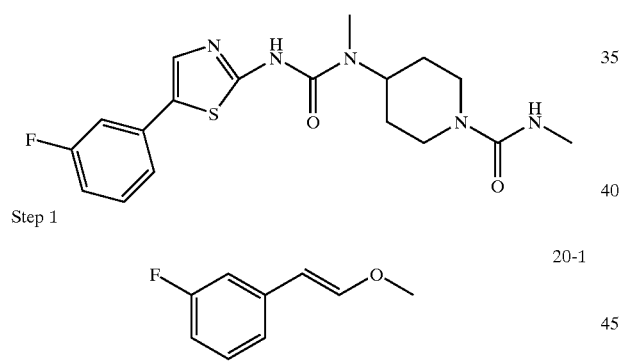

20

Step 1

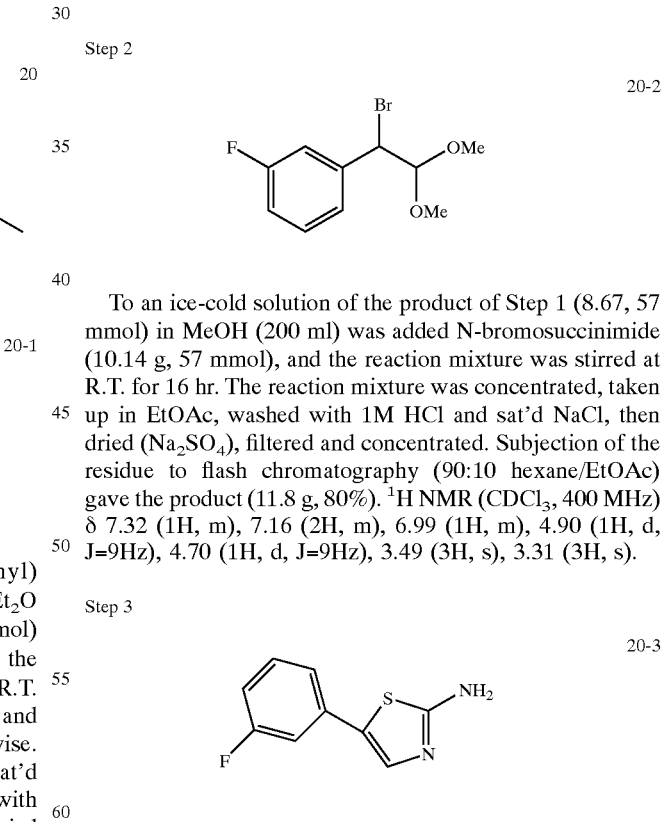

To an ice-cold suspension of (methoxymethyl)triphenylphosphonium chloride (30.4 g, 89 mmol) in Et₂O (250 ml) was added 1.8 M phenyllithium (49.3 ml, 89 mmol) dropwise under N₂. After the addition was complete, the reaction mixture was stirred at 0° C. for 0.25 hr, then at R.T. for 0.5 hr. The reaction mixture was cooled to −10° C. and 3-fluorobenzaldehyde (10 g, 81 mmol) was added dropwise. The reaction mixture was stirred at R.T. overnight, then sat'd NH₄Cl was added. The aqueous layer was extracted with Et₂O (2×), and the combined organic layers were dried (Na₂SO₄), filtered, and concentrated. Flash chromatography (hexane) of the residue afforded the product (8.67 g, 70%) as a mixture of isomers. ¹H NMR (CDCl₃, 400 MHz, major isomer) δ 7.36 (1H, m), 7.32 (1H, m), 7.07 (1H, d, J=17Hz), 6.96 (1H, m), 6.93 (1H, m), 5.77 (1H, d, J=17Hz), 3.70 (3H, s).

Step 2

To an ice-cold solution of the product of Step 1 (8.67, 57 mmol) in MeOH (200 ml) was added N-bromosuccinimide (10.14 g, 57 mmol), and the reaction mixture was stirred at R.T. for 16 hr. The reaction mixture was concentrated, taken up in EtOAc, washed with 1M HCl and sat'd NaCl, then dried (Na₂SO₄), filtered and concentrated. Subjection of the residue to flash chromatography (90:10 hexane/EtOAc) gave the product (11.8 g, 80%). ¹H NMR (CDCl₃, 400 MHz) δ 7.32 (1H, m), 7.16 (2H, m), 6.99 (1H, m), 4.90 (1H, d, J=9Hz), 4.70 (1H, d, J=9Hz), 3.49 (3H, s), 3.31 (3H, s).

Step 3

A mixture of the product of Step 2 (11.5 g, 43.7 mmol), thiourea (6.0 g, 79 mmol) and 48% HBr (0.1 ml) was stirred at 100° C. for 3 hr. The reaction mixture was allowed to cool to R.T., acidified with 6N HCl, and washed with CH₂Cl₂. The aqueous layer was brought to pH 9 by addition of aqueous NH₄OH and the resultant precipitate was collected. Subjection of the dried precipitate to flash chromatography (2:98 then 5:95 MeOH/CH$_2$Cl$_2$) gave the product (1.61 g, 19%). $^1$H NMR (CDCl$_3$, 400 MHz) δ 7.30 (2H, m), 7.18 (1H, m), 7.11 (1H, m), 6.93 (1H, m), 5.07 (2H, b).

Step 4

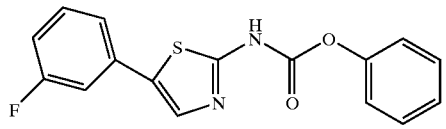

20-4

To a stirred suspension of NaH (103 mg, 2.6 mmol, 60% dispersion) in THF (30 ml) under N$_2$ was added the product of Step 3 (500 mg, 2.6 mmol). After 1 hr, the reaction mixture was cooled in an ice bath, and phenyl chloroformate (0.32 ml, 2.6 mmol) in THF (20 ml) was added dropwise. The reaction mixture was stirred for 16 hr, during which time it attained R.T. The reaction mixture was diluted with EtOAc, washed with sat'd NH$_4$Cl solution, dried (Na$_2$SO$_4$), filtered and concentrated. Subjection of the residue to flash chromatography (CH$_2$Cl$_2$) afforded the product (0.39 g, 48%). $^1$H NMR (CDCl$_3$, 400 MHz) δ 7.65 (1H, s), 7.48 (2H, m), 7.38–7.20 (6H, m), 7.00 (1H, m), 2.9 (1H, b). MS (m/e) 315 (M+H)$^+$.

Step 5

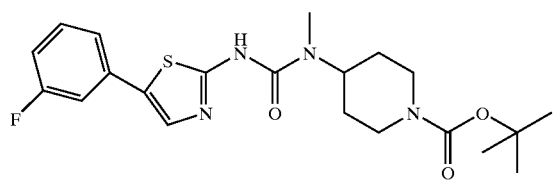

20-5

A mixture of the product of Step 4 (390 mg, 1.24 mmol), Preparation 1 (266 mg, 1.24 mmol) and Et$_3$N (0.5 ml, 3.6 mmol) in THF (25 ml) was refluxed for 3 hr. The reaction mixture was allowed to cool, diluted with EtOAc, washed with sat'd NH$_4$Cl solution, dried (Na$_2$SO$_4$), filtered and concentrated. Subjection of the residue to flash chromatography (2:98 MeOH/CH$_2$Cl$_2$) afforded the product (537 mg, 100%). $^1$H NMR (CDCl$_3$, 400 MHz) δ 9.54 (1H, b), 7.51 (1H, s), 7.29 (3H, m), 6.96 (1H, m), 4.39 (1H, m), 4.21 (2H, b), 2.88 (3H, s), 2.78 (2H, m), 1.63 (4H, m), 1.45 (9H, s). MS (m/e) 435 (M+H)$^+$.

Step 6

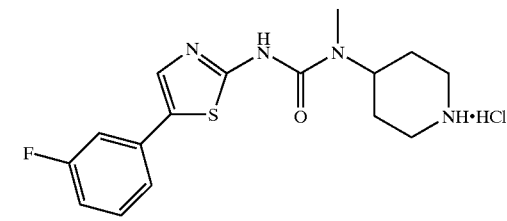

20-6

Reaction of the product of Step 5 with HCl by essentially the procedure of Example 6, Step 4 gave the product. $^1$H NMR (CD$_3$OD, 400 MHz) δ 8.00 (1H, s), 7.58 –7.41 (3H, m), 7.19 (1H, m), 4.42 (1H, m), 3.54 (2H, m), 3.20 (2H, m), 3.07 (3H, s), 2.15 (2H, m), 2.01 (2H, m). MS (m/e) 335 (M+H)$^+$.

Step 7

Reaction of the product of Step 6 (20 mg, 0.05 mmol) with methyl isocyanate (1 drop) by essentially the procedure of Example 15 followed by PTLC (10:90 MeOH/CH$_2$Cl$_2$) gave the product (7 mg, 36%). MS m/e 392 (M+H)$^+$.

EXAMPLE 21

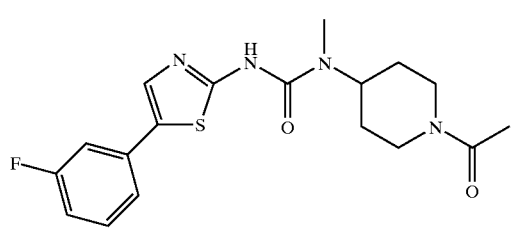

21

Reaction of 20-6 with acetyl chloride essentially the procedure of Example 4 gave the product. MS m/e 377 (M+H)$^+$.

EXAMPLE 22

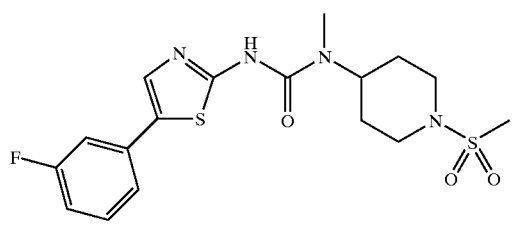

22

Reaction of 20-6 with methanesulfonyl chloride by the procedure of Example 3, Step 3 gave the product. $^1$H NMR (CDCl$_3$, 400 MHz) δ 7.52 (1H, s), 7.34 (1H, m), 7.22 (1H, m), 7.21 (1H, m), 6.97 (1H, m), 4.40 (1H, m), 3.92 (2H, m), 2.91 (3H, s), 2.79 (3H, s), 2.75 (2H, m), 1.83 (4H, m). MS m/e 413 (M+H)$^+$.

EXAMPLE 23

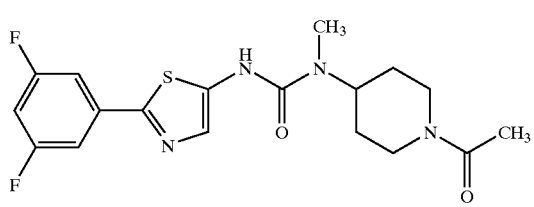

23

Step 1

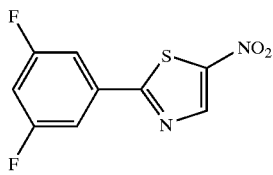

23-1

To a solution of 2-bromo-5-nitrothiazole (0.784 g, 3.75 mmol) and 0.5 M 3,5-difluorophenylzinc bromide in THF (5.0 ml, 12.5 mmol) was added Pd(PPh$_3$)$_4$ (0.173 g, 0.15 mmol) under argon. The reaction mixture was stirred at R.T. for 30 min. then poured into water (25 ml). The whole was extracted with CH$_2$Cl$_2$ (3×50 ml) dried (Na$_2$SO$_4$), filtered, and evaporated. The residue was subjected to PTLC (1:10 EtOAc/hexane) to give the product (0.49 g, 81%). $^1$H NMR (CDCl$_3$) δ 8.59 (s, 1H), 7.52 (m, 2H), 7.01 (m, 1H). MS m/e 243 (M+H)$^+$.

Step 2

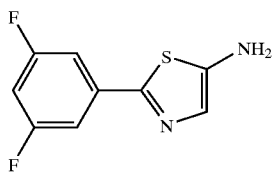

23-2

To a solution of the product of Step 1 (0.300 g, 1.24 mmol) in MeOH (20 ml) was added nickel chloride hexahydrate (0.589 g, 2.48 mmol) and sodium borohydride (0.187 g, 4.95 mmol) at 0° C. The reaction mixture was stirred at R.T. for 10 min. and quenched with water (10 ml). The mixture was filtered via celite. The celite was washed with CH$_2$Cl$_2$ (100 ml). The filtrate was extracted with CH$_2$Cl$_2$ (3×50 ml), and the combined organic layers were dried (Na$_2$SO$_4$), filtered, and evaporated. The residue was subjected to PTLC (1:2 EtOAc/hexane) to give the product (0.060 g, 23%). $^1$H NMR (CDCl$_3$) δ 7.30 (m, 2H), 7.1 (s, 1H), 6.77 (m, 1H), 3.90 (bs, 2H). MS m/e 213 (M+H)$^+$.

Step 3

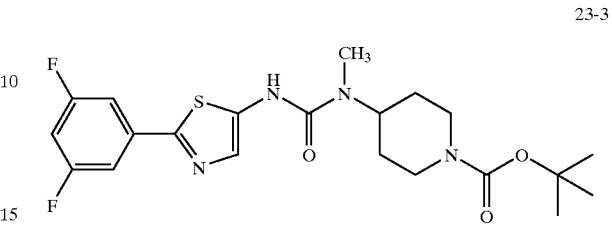

23-3

To a solution of the product of Step 2 (0.080 g, 0.377 mmol) in anhydrous pyridine (3.0 ml) was added phenyl chloroformate (0.071 ml, 0.566 mmol) slowly. The reaction mixture was stirred at R.T. overnight and evaporated. To a solution of the residue in chloroform (5 ml) and was added Preparation 1 (0.122 g, 0.567 mmol) and Et$_3$N (0.16 ml, 1.13 mmol). The reaction mixture was refluxed for 21 hr, allowed to cool and poured into water (25 ml). The whole was extracted with CH$_2$Cl$_2$ (3×50 ml), dried (Na$_2$SO$_4$), filtered and evaporated (1:20 MeOH/CH$_2$Cl$_2$) to give the product (0.087 g, 51%) as a solid. $^1$H NMR (CDCl$_3$) δ 7.78 (s, 1H), 7.43 (s, 1H), 7.36 (m, 2H), 6.78 (m, 1H), 4.4 (bs, 1H), 4.2 (bs, 1H), 3.82 (bs, 1H), 2.89 (s, 3H), 2.78 (m, b, 2H), 1.8–1.5 (m, 4H), 1.45 (s, 9H). MS m/e 453 (M+H)$^+$.

Step 4

Subjection of the product of Step 3 to the procedures of Example 3, Steps 2 and 3 gave the product. $^1$H NMR (CDCl$_3$) δ 8.04 (s, 1H), 7.54 (s, 1H), 7.38 (m, 2H), 6.78 (m, 1H), 4.78 (m, 1H), 4.51 (m, 1H), 3.95 (m, 1H), 3.20 (m, 1H), 2.92 (m, 3H), 2.61 (m, 1H), 2.11 (s, 3H), 1.75 (m, 2H), 1.59 (m, 2H). MS m/e 395 (M+H)$^+$.

Use of the appropriate reagents and procedures afforded the following compounds:

| STRUCTURE | $^1$H NMR | MS (M + H)$^+$ |
|---|---|---|
| 23A | (CDCl$_3$) δ 7.52(s, 1H), 7.40(m, 3H), 6.80(m, 1H), 4.22(m, 1H), 3.93(m, 2H), 2.94(s, 3H), 2.77 (m, 5H), 1.82(m, 4H). | 431 |
| 23B | (CDCl$_3$) δ 7.51(s, 1H), 7.41(m, 3H), 6.80(m, 1H), 4.80(m, 1H), 4.50(m, 1H), 3.95(m, 1H), 3.15 (m, 1H), 2.91(s, 3H), 2.60(m, 1H), 2.32(m, 2H), 1.80–1.50(m, 6H), 0.98(t, 3H). | 423 |

-continued

| STRUCTURE | ¹H NMR | MS (M + H)⁺ |
|---|---|---|
| 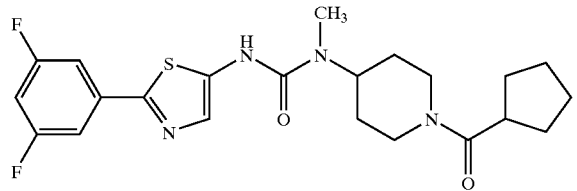<br>23C | (CDCl₃) δ 7.52(s, 1H), 7.46(s, 1H), 7.40(m, 2H), 6.79(m, 1H), 4.80(m, 1H), 4.50(m, 1H), 4.15 (m, 1H), 3.15(m, 1H), 2.89(s, 3H), 2.70(m, 1H), 2.60(m, 1H), 1.9–1.5(m, 12H). | 449 |
| 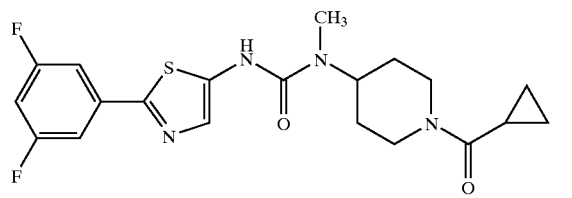<br>23D | (CDCl₃) δ 7.62(s, 1H), 7.47(s, 1H), 7.40(m, 2H), 6.80(m, 1H), 4.78(m, 1H), 4.50(m, 1H), 4.32 (m, 1H), 3.20(m, 1H), 2.91(s, 3H), 2.62(m, 1H), 1.80–1.60(m, 5H), 0.99(m, 2H), 0.80(m, 2H). | 421 |
| 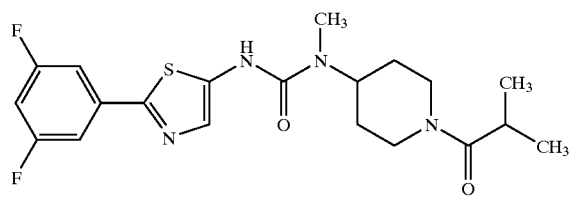<br>23E | (CDCl₃) δ 7.73(s, 1H), 7.46(s, 1H), 7.38(m, 2H), 6.80(m, 1H), 4.80(m, 1H), 4.50(m, 1H), 4.03 (m, 1H), 3.14(m, 1H), 2.91(s, 3H), 2.82(m, 1H), 2.59(m, 1H), 1.95–1.62(m, 2H), 1.57(m, 2H), 1.16(m, 6H). | 423 |
| 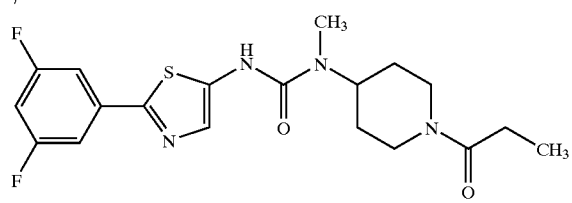<br>23F | (CDCl₃) δ 7.49(s, 1H), 7.45(s, 1H), 7.40(m, 2H), 6.79(m, 1H), 4.80(m, 1H), 4.50(m, 1H), 3.95 (m, 1H), 3.18(m, 1H), 2.91(s, 3H), 2.60(m, 1H), 2.37(q, 2H), 1.80–1.50(m, 4H), 1.16(t, 3H). | 409 |

EXAMPLE 24

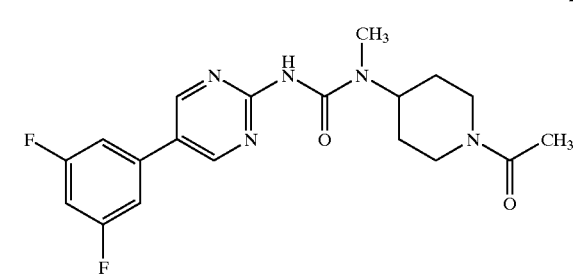

Step 1

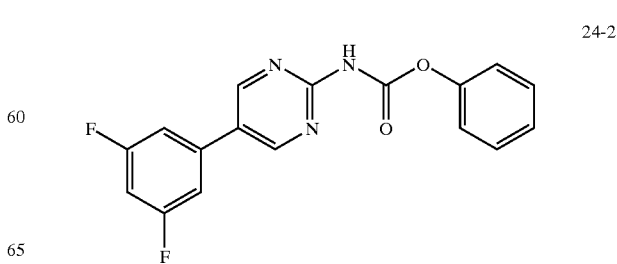

A flask charged with 3,5-difluorophenylboronic acid (4.40 g, 27.9 mmol), 2-amino-5-bromopyrimidine (4.00 g, 23 mmol), toluene (40 ml), water (7 ml) and cesium carbonate (8.20 g, 25.2 mmol) was purged with N₂. PdCl₂ (dppf)₂.CH₂Cl₂ (0.94 g, 1.15 mmol) was added and the reaction mixture was refluxed for 2.5 hr. The reaction mixture was allowed to cool then poured into water (100 ml). The whole was extracted with EtOAc (3×150 ml), dried (Na₂SO₄), filtered and concentrated. Subjection of the residue to flash chromatography (gradient 1:5 to 1:1 acetone/hexane) gave the product (2.30 g, 48%). ¹H NMR (CDCl₃) δ 8.29 (s, 2H), 6.84 (m, 2H), 6.62 (m, 1H), 4.18 (s, 2H). MS m/e 208 (M+H)⁺.

Step 2

To a solution of the product of Step 1 (0.500 g, 2.42 mmol) in anhydrous pyridine (6 ml) was added phenyl chloroformate (0.33 ml, 2.62 mmol) dropwise. The reaction mixture was stirred for 16 hr, then evaporated. The residue was subjected to PTLC (1:30 CH₃OH/CH₂Cl₂) to give the product (0.30 g, 38%). ¹HNMR (CDCl₃) δ 8.84 (m, 3H), 7.42 (m, 2H), 7.26 (m, 3H), 7.06 (m, 2H), 6.89 (m, 1H). MS m/e 328 (M+H)⁺.

Step 4

Subjection of the product of Step 3 to the procedures of Example 10, Steps 3 and 4 gave the product. ¹H NMR (CDCl₃) δ 8.71 (s, 2H), 7.62 (s, b, 1H), 7.02 (m, 2H), 6.84 (m, 1H), 4.78 (m, 1H), 4.43 (m, 1H), 3.90 (m, 1H), 3.18 (m, 1H), 2.92 (s, 3H), 2.60 (m, 1H), 2.09 (s, 3H), 1.82 (m, 2H), 1.60 (m, 2H). MS m/e 390 (M+H)⁺.

Use of the appropriate reagents and procedures afforded the following compounds.

| STRUCTURE | ¹H NMR | MS (M + H)⁺ |
|---|---|---|
| 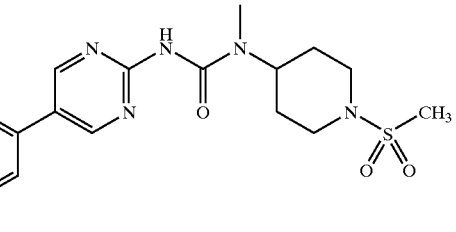<br>24A | (CDCl₃) δ 8.74(s, 2H), 7.42(s, b, 1H), 7.04(m, 2H), 6.83(m, 1H), 4.43(m, 1H), 3.95(m, 2H), 2.97(s, 3H), 2.80(m, 5H), 1.88 (m, 4H). | 426 |
| 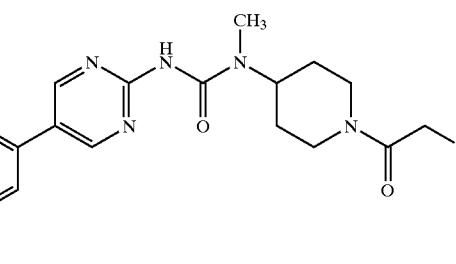<br>24B | (CDCl₃) δ 8.73(s, b, 2H), 7.59 (s, b, 1H), 7.03(m, 2H), 6.83(m, 1H), 4.79(m, 1H), 4.47(m, 1H), 3.94(m, 1H), 3.09(m, 1H), 2.92 (s, 3H), 2.59(m, 1H), 2.35(m, 2H), 1.82(m, 2H), 1.61(m, 2H), 1.15(m, 3H). | 404 |

Step 3

24-3

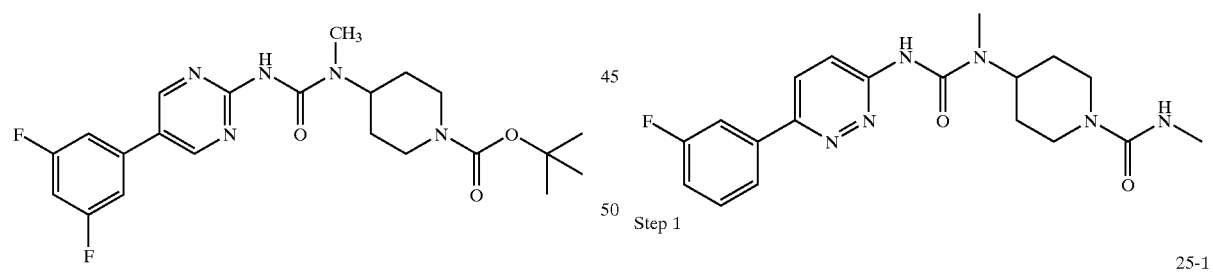

To a solution of the product of Step 2 (0.145 g, 0.44 mmol) in chloroform (5 ml) was added Preparation 1 (0.095 g, 0.44 mmol) and Et₃N (0.19 ml, 1.33 mmol). The reaction mixture was refluxed for 3 hr, allowed to cool and poured into water (15 ml). The whole was extracted with EtOAc (3×), and the combined organic layers were dried (Na₂SO₄), filtered and evaporated. The residue was subjected to PTLC (1:30 CH₃OH/CH₂Cl₂) to give the product (0.205 g, 100%). ¹H NMR (CDCl₃) δ 8.71 (s, 2H), 7.70 (s, b, 1H), 7.01 (m, 2H), 6.83 (m, 1H), 4.36 (m, 1H), 4.21 (m, 2H), 2.92 (s, 3H), 2.78 (m, 2H), 1.74 (m, 2H), 1.63 (m, 2H), 1.45 (s, 9H). MS m/e 448 (M+H)⁺.

EXAMPLE 25

25

Step 1

25-1

A mixture of 3,6-dichloropyridazine (7.5 g) and NH₃ (9 g) in EtOH (100 ml) was heated at 130° C. in stainless steel bomb for 16 hr. After the reaction mixture had cooled to R.T., it was concentrated, and the residue was subjected to Soxhlet extraction (EtOAc). The residue obtained from the EtOAc extract was recrystallized from EtOAc to give the product (3.81 g).

Step 2

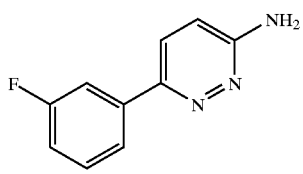

25-2

A suspension of the product of Step 1 (200 mg, 1.54 mmol), 3-fluorophenylboronic acid (260 mg, 1.86 mmol), and 2M $K_2CO_3$ (1.6 ml, 3.2 mmol) in EtOH (3 ml) and toluene (10 ml) was purged with $N_2$. $Pd(PPh_3)_4$ (90 mg, 0.08 mmol) was added, and the mixture was heated at 110° C. for 24 hr. The cooled reaction mixture was concentrated and partitioned between water and EtOAc. The organic layer was washed with water, dried ($Na_2SO_4$), filtered and evaporated. Subjection of the residue to PTLC (7:93 MeOH/$CH_2Cl_2$) gave the product (168 mg, 58%).

Step 3

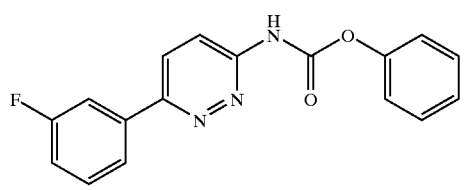

25-3

Reaction of the product of Step 2 by essentially the procedure of Example 20, Step 4 gave the product. $^1$H NMR (CDCl$_3$, 400 MHz) δ 8.75 (1H, b), 8.43 (1H, m), 7.95 (1H, m), 7.82–7.78 (2H, m), 7.52–7.18 (7H, m). MS m/e 310 (M+H)$^+$.

Step 4

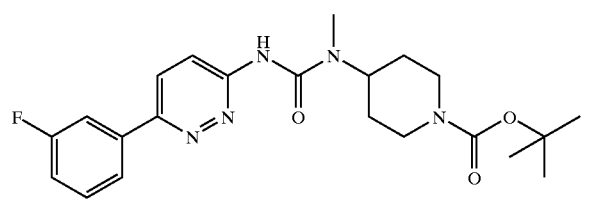

25-4

Reaction of the product of Step 3 with Preparation 1 by essentially the procedure of Example 20, Step 5 gave the product. $^1$H NMR (CDCl$_3$, 400 MHz) δ 8.6 (1H, b), 8.36 (1H, m), 7.80 (1H, m), 7.73 (2H, m), 7.44 (1H, m), 7.12 (1H, m), 4.41 (1H, m), 4.21 (2H, m), 2.99 (3H, s), 2.80 (2H, m), 1.79–1.60 (4H, m), 1.43 (9H, s). MS m/e 430 (M+H)$^+$.

Step 5

Subjection of the product of Step 4 by the procedure of Example 20, Steps 6 and 7 gave the product. $^1$H NMR (CDCl$_3$, 400 MHz) δ 8.40 (1H, m), 8.20 (1H, b), 7.82 (1H, m), 7.50 (2H, m), 7.42 (1H, m), 7.15 (1H, m), 4.54 (1H, m), 4.44 (1H, m), 4.09 (2H, m), 2.98 (3H, s), 2.90 (2H, m), 2.79 (3H, s), 1.75–1.64 (4H, m). MS m/e 387 (M+H)$^+$.

Use of the appropriate procedures afforded the following compounds:

EXAMPLE 26

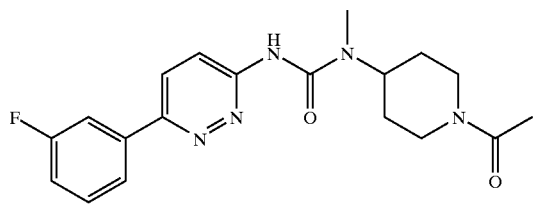

26

$^1$H NMR (CDCl$_3$, 400 MHz) δ 8.6 (1H, b), 8.34 (1H, m), 7.80 (1H, m), 7.73 (2H, m), 7.44 (1H, m), 7.13 (1H, m), 4.76 (1H, m), 4.50 (1H, m), 3.89 (1H, m), 3.15 (1H, m), 2.99 (3H, s), 2.25 (1H, m), 2.09 (3H, s), 1.79 (2H, m), 1.63 (2H, m). MS m/e 372 (M+H)$^+$.

EXAMPLE 27

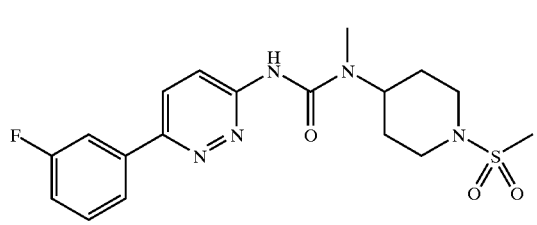

27

$^1$H NMR (CDCl$_3$, 400 MHz) δ 8.47 (1H, m), 7.86 (1H, m), 7.77 (2H, m), 7.47 (1H, m), 7.17 (1H, m), 4.47 (1H, m), 3.97 (2H, m), 3.02 (3H, s), 2.83 (2H, m), 2.82 (3H, s), 1.93–1.50 (4H, m). MS m/e 408 (M+H)$^+$.

What is claimed:
1. A compound of Formula I:

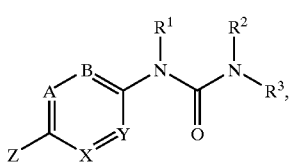

I or a pharmaceutically acceptable salt of said compound, or where applicable, a geometric or optical isomer or racemic mixture thereof, wherein =A-B= is =C(R$^4$)—N= and —X=Y— is —N=C(R$^6$)—, or =A-B= is —N—C(R$^6$)—, and —X=Y— is —C(R$^4$)=N—

Z is

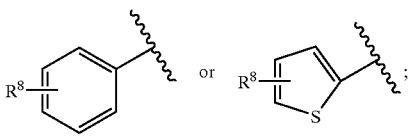

$R^1$ is H or —$(C_1-C_6)$alkyl;

$R^2$ is H, —$(C_1-C_6)$alkyl, —$(C_3-C_7)$cycloalkyl or —$(C_1-C_6)$alkyl$(C_3-C_7)$cycloalkyl;

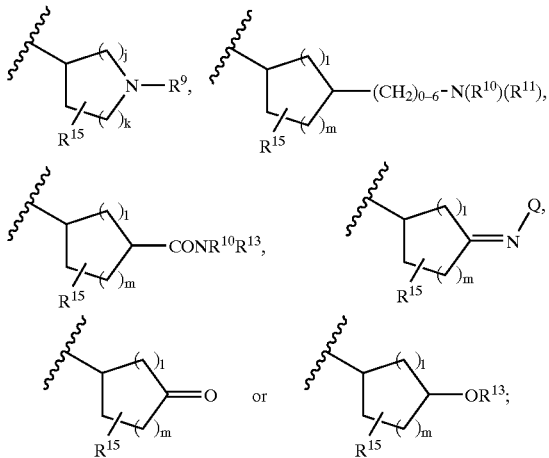

Q is —$OR^{13}$, or —$NR^{13}R^{14}$;

j is 1 or 2;

k is 0, 1 or 2;

l is 0, 1 or 2;

m is 0, 1 or 2;

$R^4$, $R^5$, $R^6$ and $R^7$ may be the same or different, and are independently selected from the group consisting of H, —OH, halogen, polyhaloalkyl, —$(C_1-C_6)$alkyl, —$(C_3-C_7)$cycloalkyl, —$(C_1-C_6)$alkyl$(C_3-C_7)$cycloalkyl, —CN, $NR^{10}R^{11}$, $NR^{13}R^{14}$, —$O(C_1-C_6)$alkyl, —$O(C_3-C_7)$cycloalkyl, —$O(C_1-C_6)$alkyl$(C_3-C_7)$cycloalkyl, —$S(C_1-C_6)$alkyl, —$S(C_3-C_7)$cycolalkyl and —$S(C_1-C_6)$alkyl$(C_3-C_7)$cycloalkyl;

$R^8$ is 1 to 3 substituents, which may be the same or different, and are independently selected from the group consisting of H, halogen, —OH, polyhaloalkyl, polyhaloalkoxy, —CN, —$NO_2$, —$(C_1-C_6)$alkyl, —$(C_3-C_7)$cycloalkyl,—$(C_1-C_6)$alkyl$(C_3-C_7)$cycloalkyl, $NR^{10}R^{11}$, $NR^{13}R^{14}$, —$O(C_1-C_6)$alkyl, —$O(C_3-C_7)$cycloalkyl, —$O(C_1-C_6)$alkyl$(C_3-C_7)$cycloalkyl and —$CONR^{13}R^{14}$;

$R^9$ is —$SO_2(C_1-C_6)$alkyl, —$SO_2(C_3-C_7)$cycloalkyl, —$SO_2(C_1-C_6)$alkyl $(C_3-C_7)$cycloalkyl,—$SO_2(C_1-C_6)$polyhaloalkyl, —$SO_2$[hydroxy$(C_2-C_6)$alkyl], —$SO_2$[amino$(C_2-C_6)$alkyl], —$SO_2$[alkoxy$(C_2-C_6)$alkyl], —$SO_2$[alkylamino$(C_2-C_6)$alkyl], —$SO_2$[dialkylamino$(C_2-C_6)$alkyl], —$SO_2$(aryl), —$SO_2$(heteroaryl), —$SO_2$[aryl$(C_1-C_6)$ alkyl], —$SO_2NR^{13}R^{14}$, —$CO(C_1-C_6)$alkyl, —$CO(C_3-C_7)$cycloalkyl, —$CO(C_1-C_6)$alkyl $(C_3-C_7)$cycloalkyl, $CO(C_1-C_6)$polyhaloalkyl, —C(O)aryl, —C(O)heteroaryl, —$CONR^{13}R^{14}$, —C(S)$NR^{13}R^{14}$, aryl, heteroaryl, —$(CH_2)CONR^{13}R^{14}$, —C(=NCN)alkylthio, —C(=NCN)$NR^{13}R^{14}$, —$(C_1-C_6)$alkyl, —$(C_3-C_7)$cycloalkyl, —$(C_1-C_6)$alkyl$(C_3-C_7)$cycloalkyl, —$(C_1-C_6)$alkylaryl, —$(C_1-C_6)$alkylheteroaryl or —$COOR^{12}$;

$R^{10}$ is H or alkyl;

$R^{11}$ is H, —$(C_1-C_6)$alkyl, —$(C_3-C_7)$cycloalkyl, —$(C_1-C_6)$alkyl$(C_3-C_7)$cycloalkyl, aryl, heteroaryl, —$SO_2(C_1-C_6)$alkyl, —$SO_2(C_3-C_7)$cycloalkyl, —$SO_2$ $(C_1-C_6)$alkyl$(C_3-C_7)$cycloalkyl, —$SO_2(C_1-C_6)$polyhaloalkyl, —$SO_2$(aryl), —$SO_2$(heteroaryl), —$CO(C_1-C_6)$alkyl, —$CO(C_3-C_7)$cycloalkyl, —$CO(C_1-C_6)$alkyl$(C_3-C_7)$cycloalkyl, —C(O)aryl, —C(O)heteroaryl, —$CONR^{13}R^{14}$ or —$COOR^{12}$;

$R^{12}$ is $(C_1-C_6)$alkyl, $(C_3-C_7)$cycloalkyl, $(C_1-C_6)$alkyl$(C_3-C_7)$cycloalkyl, —$(C_1-C_6)$alkylaryl, —$(C_1-C_6)$alkylheteroaryl, aryl or heteroaryl;

$R^{13}$ and $R^{14}$ may be the same or different and are independently H, —$(C_1-C_6)$alkyl, —$(C_3-C_7)$cycloalkyl, —$(C_1-C_6)$alkyl$(C_3-C_7)$cycloalkyl, —$(C_1-C_6)$alkylaryl, aryl or heteroaryl; and, $R^{15}$ is one or two substituents, which may be the same or different, and are independently H, —$(C_1-C_6)$alkyl, —$(C_3-C_7)$cycloalkyl, —$(C_1-C_6)$alkyl$(C_3-C_7)$cycloalkyl, aryl, heteroaryl, —CN, —$CONR^{13}R^{14}$, —$COOR^{13}$, —OH, —$O(C_1-C_6)$alkyl, —$O(C_3-C_7)$cycloalkyl, —$O(C_1-C_6)$alkyl$(C_3-C_7)$cycloalkyl, —$NR^{10}R^{11}$, —$NR^{13}R^{14}$, or a —$(C_1-C_6)$alkyl group substituted by an aryl, heteroaryl, hydroxy, alkoxy, —$NR^{10}R^{11}$, —$NR^{13}R^{14}$, —$CONR^{13}R^{14}$, or —$COOR^{13}$ group, provided that a chemically stable compound results from substitution by $R^{15}$.

2. A compound as defined in claim 1 wherein the heterocyclic group attached to Z is

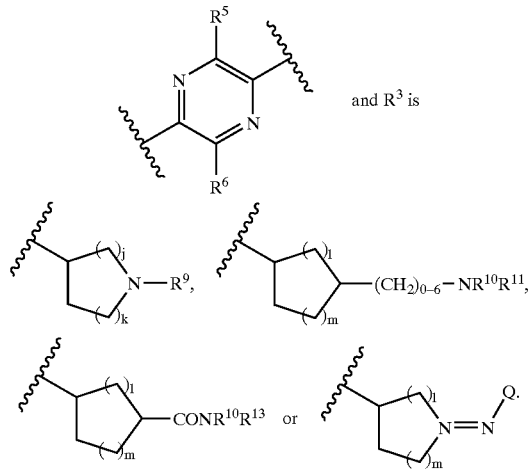

and $R^3$ is

3. A compound as defined in claim 2 wherein $R^1$ is hydrogen, $R^2$ is hydrogen or $(C_1-C_6)$alkyl, $R^5$ and $R^6$ are hydrogen or halogen, $R^6$ is 1 to 3 substituents, which may be the same or different, and are independently selected from the group consisting of H, halogen, —$O(C_1-C_6)$alkyl, —OH, polyhaloalkyl and polyhaloalkoxy, $R^9$ is —$SO_2(C_1-C_6)$alkyl, —$SO_2(C_3-C_7)$cycloalkyl, —$SO_2(C_1-C_6)$alkyl $(C_3-C_7)$cycloalkyl, —$SO_2$aryl, —$SO_2$heteroaryl, —$SO_2NR^{13}R^{14}$, —$CO(C_1-C_6)$alkyl, —$CO(C_3-C_7)$cycloalkyl, —$CO(C_1-C_6)$alkyl$(C_3-C_7)$cycloalkyl, —C(O)aryl, —C(O)heteroaryl, aryl, heteroaryl, $R^{10}$ is H or —$(C_1-C_6)$alkyl, $R^{11}$ is —$SO_2(C_1-C_6)$alkyl, Q is —$OR^{13}$ or —$NR^{13}R^{14}$;

$R^{13}$ and $R^{14}$ may be the same or different, and are independently H or —$(C_1-C_6)$alkyl;

the sum of j and k is 2 or 3; and, the sum of l and m is 2 or 3.

4. A compound as defined in claim 3 wherein $R^3$ is

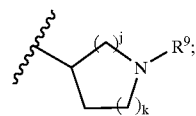

$R^9$ is —$SO_2(C_1-C_6)$alkyl, —$SO_2(C_3-C_7)$cycloalkyl, —$SO_2$aryl, —$SO_2$heteroaryl, —$CO(C_1-C_6)$alkyl, —$CO(C_3-C_7)$cycloalkyl, —$CO(C_1-C_6)$alkyl$(C_3-C_7)$cycloalkyl, —C(O)aryl, —C(O)heteroaryl, aryl, or heteroaryl, and the sum of j and k is 2 or 3.

5. The compound as defined in claim 1 of the formula:

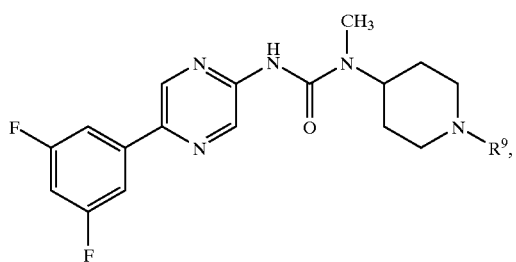

or a pharmaceutically acceptable salt of said compound or where applicable, a geometric or optical isomer or racemic mixture thereof, wherein $R^9$ is as shown in the table below:

| | $R^9$ |
|---|---|
| 0 | 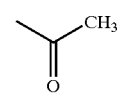 |
| 0A | 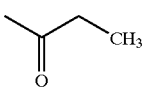 |
| 0B | 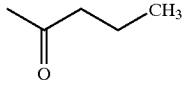 |
| 0C | 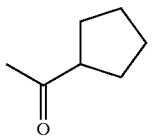 |
| 0D | 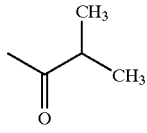 |

-continued

| | $R^9$ |
|---|---|
| 0E | 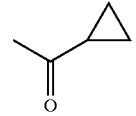 |
| 0F | 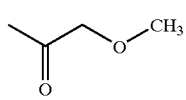 |
| 0G | 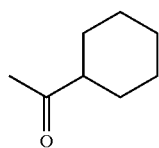 |
| 0H | 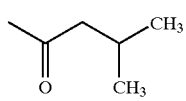 |
| 0I | 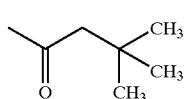 |
| 0J | 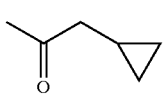 |
| 0K | 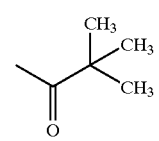 |
| 0L | 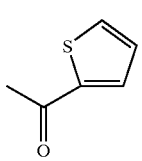 |
| 0M | 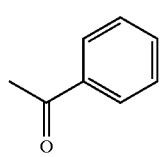 |
| 0N | 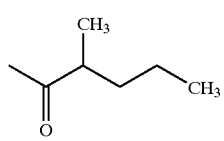 |
| 0O | 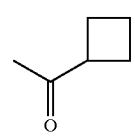 |

-continued

| | R⁹ |
|---|---|
| 0P | 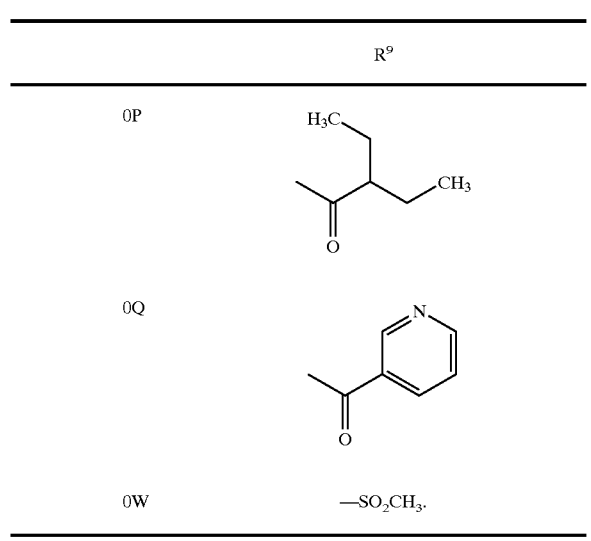 |
| 0Q | |
| 0W | —SO₂CH₃. |

6. The compound as defined in claim 1 of the formula:

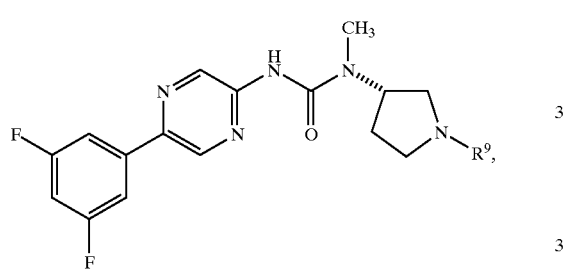

or a pharmaceutically acceptable salt of said compound, or where applicable, a geometric or optical isomer or racemic mixture thereof, wherein R⁹ is as shown in the table below:

| | R⁹ |
|---|---|
| 0S | —SO₂CH₃ |
| 0T | 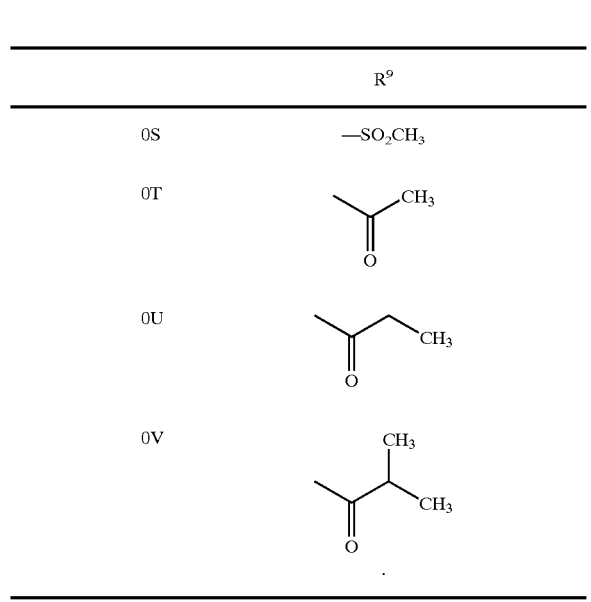 |
| 0U | |
| 0V | |

7. The compound as defined in claim 1 of the formula:

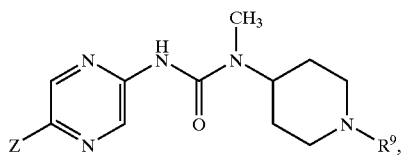

or a pharmaceutically acceptable salt of said compound, or where applicable, a geometric or optical isomer or racemic mixture thereof, wherein Z and R⁹ are as shown in the table below:

| | Z | R⁹ |
|---|---|---|
| 0X | | —SO₂CH₃ |
| 0Y | 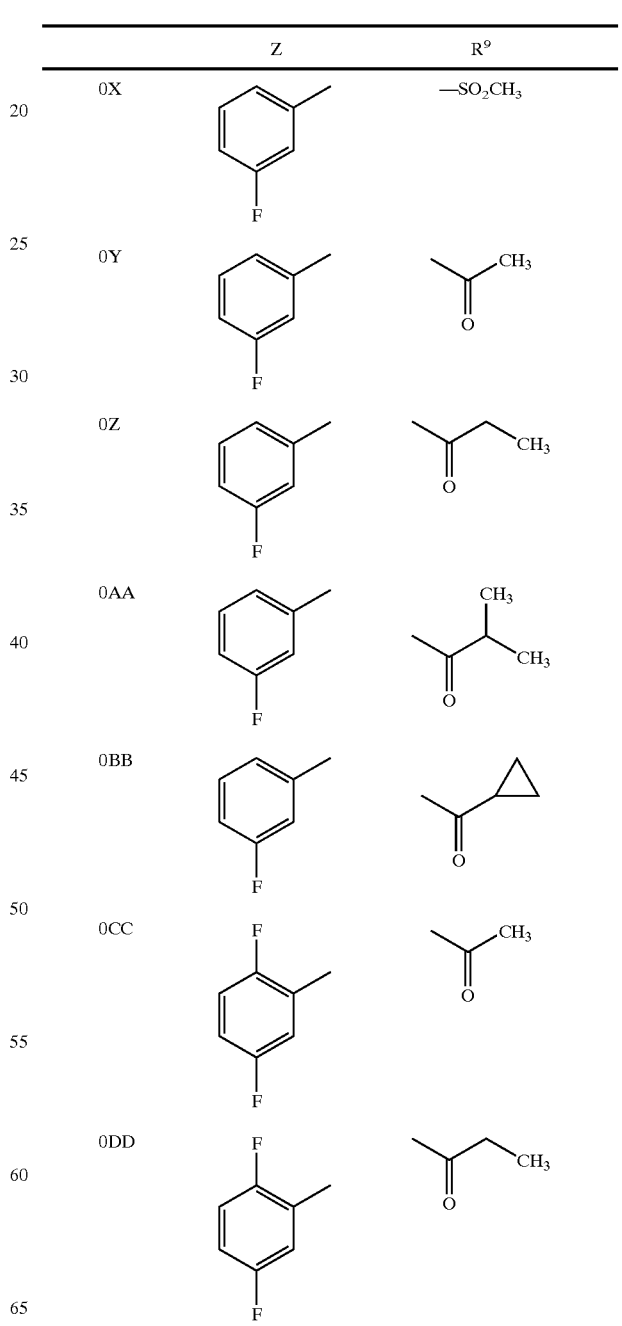 | |
| 0Z | | |
| 0AA | | |
| 0BB | | |
| 0CC | | |
| 0DD | | |

| | Z | R⁹ |
|---|---|---|
| 0EE | 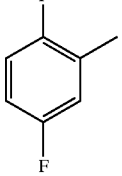 | 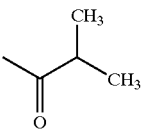 |
| 0FF | 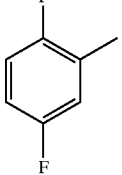 | 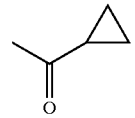 |
| 0GG | 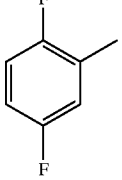 | 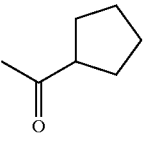 |
| 0HH | 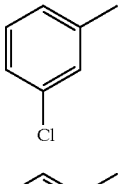 | 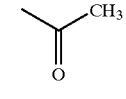 |
| 0II | 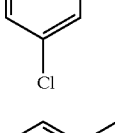 |  |
| 0JJ | 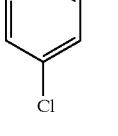 | 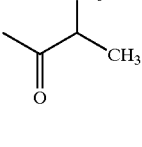 |
| 0KK | 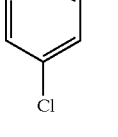 | 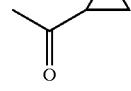 |
| 0LL | 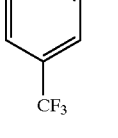 | 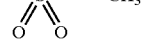 |
| 0MM | 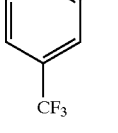 | 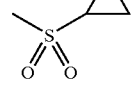 |
| 0NN | 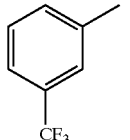 | 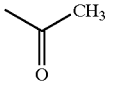 |
| 0OO | 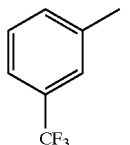 | 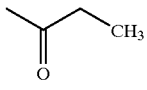 |
| 0PP | 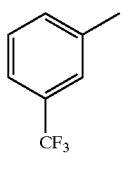 | 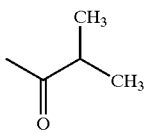 |
| 0QQ | 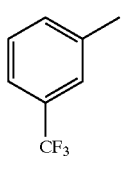 | 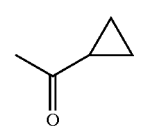 |
| 0RR | 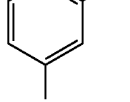 | 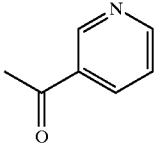 |
| 1 | 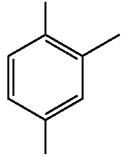 | —SO$_2$CH$_3$ |
| 1A |  | —SO$_2$CH$_3$ |
| 1B |  | —SO$_2$CH$_3$ |
| 1C |  | —SO$_2$CH$_3$ |

-continued

| | Z | R⁹ |
|---|---|---|
| 1D | 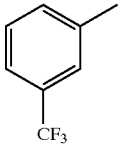 | —SO$_2$CH$_3$ |
| 1E | 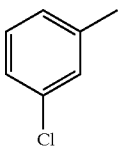 | —SO$_2$CH$_3$. |

8. A pharmaceutical composition which comprises an effective amount of a compound as defined in claim 1 and a pharmaceutically acceptable carrier therefor.

9. A method of treating eating disorders, obesity and disorders related to obesity comprising administering to a mammal in need of such treatment a therapeutically effective amount of a compound of claim 1 or a pharmaceutically acceptable salt of said compound.

10. The method of claim 9 wherein said eating disorder is hyperphagia.

11. A method of treating disorders associated with obesity comprising administering to a mammal in need of such treatment a therapeutically effective amount of a compound of claim 1 or a pharmaceutically acceptable salt of said compound.

12. The method of claim 11 wherein said disorders associated with obesity are type II diabetes, insulin resistance, hyperlipidemia and hypertension.

13. A pharmaceutical composition which comprises a therapeutically effective amount of a composition comprising:

a first compound, said first compound being a compound of claim 1, or a pharmaceutically acceptable salt of said compound;

a second compound, said second compound being a $\beta_3$ agonist, a thryomimetic agent, an eating behavior modifying agent or an NPY antagonist; and a pharmaceutically acceptable carrier therefor.

14. A method of treating an eating disorder which comprises administering to a mammal in need of such treatment an amount of a first compound, said first compound being a compound of claim 1, or a pharmaceutically acceptable salt of said compound;

a second compound, said second compound being a $\beta_3$ agonist, a thryomimetic agent, an eating behavior modifying agent or an NPY antagonist;

wherein the amounts of the first and second compounds result in a therapeutic effect.

15. A pharmaceutical composition which comprises a therapeutically effective amount of a composition comprising a first compound, said first compound being a compound of claim 1, or a pharmaceutically acceptable salt of said compound;

a second compound, said second compound being an aldose reductase inhibitor, a glycogen phosphorylase inhibitor, a sorbitol dehydrogenase inhibitor, insulin, metformin, acarbose, a thiazolidinedione such as troglitazone or rezulin; a glitazone such as rosaglitazone or pioglitazone; a sulfonylurea, glipazide, glyburide, or chlorpropamide; and a pharmaceutically acceptable carrier therefor.

16. A process for making a pharmaceutical composition comprising combining a compound of claim 1 and a pharmaceutically acceptable carrier.

* * * * *

UNITED STATES PATENT AND TRADEMARK OFFICE
CERTIFICATE OF CORRECTION

PATENT NO. : 6,982,267 B2  Page 1 of 1
APPLICATION NO. : 10/026651
DATED : December 18, 2001
INVENTOR(S) : Andrew Stamford et al.

It is certified that error appears in the above-identified patent and that said Letters Patent is hereby corrected as shown below:

In the Claims:

Claim 2, col. 122, line 58:   Please correct "$R^6$ is" to -- $R^8$ is --

Claim 2, col. 122, line 63:   Please correct (by removing extra space)
"-$SO_2(C_1$-$C_6)$alkyl $(C_3$-$C_7)$cycloalkyl,"
to
-- -$SO_2(C_1$-$C_6)$alkyl$(C_3$-$C_7)$cycloalkyl, --

Signed and Sealed this

Twentieth Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 6,982,267 B2  
APPLICATION NO. : 10/026651  
DATED : January 3, 2006  
INVENTOR(S) : Andrew Stamford et al.

It is certified that error appears in the above-identified patent and that said Letters Patent is hereby corrected as shown below:

In the Claims:

Claim 2, col. 122, line 58: Please correct "$R^6$ is" to -- $R^8$ is --

Claim 2, col. 122, line 63: Please correct (by removing extra space) "-$SO_2(C_1$-$C_6)$alkyl $(C_3$-$C_7)$cycloalkyl,"  
to  
-- -$SO_2(C_1$-$C_6)$alkyl$(C_3$-$C_7)$cycloalkyl, --

This certificate supersedes the Certificate of Correction issued May 20, 2008.

Signed and Sealed this

Seventeenth Day of June, 2008

JON W. DUDAS  
*Director of the United States Patent and Trademark Office*